United States Patent
Zhu et al.

(10) Patent No.: US 11,191,845 B2
(45) Date of Patent: Dec. 7, 2021

(54) CD38 ANTIBODY DRUG CONJUGATE

(71) Applicant: Sorrento Therapeutics, Inc., San Diego, CA (US)

(72) Inventors: Tong Zhu, San Diego, CA (US); Alisher Khasanov, San Diego, CA (US); Gang Chen, San Diego, CA (US); Katherine Fells, San Diego, CA (US); Heyue Zhou, San Diego, CA (US); John Dixon Gray, San Diego, CA (US)

(73) Assignee: Sorrento Therapeutics, Inc., San Diego, CA (US)

( * ) Notice: Subject to any disclaimer, the term of this patent is extended or adjusted under 35 U.S.C. 154(b) by 640 days.

(21) Appl. No.: 16/013,828

(22) Filed: Jun. 20, 2018

(65) Prior Publication Data

US 2018/0360985 A1    Dec. 20, 2018

Related U.S. Application Data

(60) Provisional application No. 62/553,438, filed on Sep. 1, 2017, provisional application No. 62/522,516, filed on Jun. 20, 2017.

(51) Int. Cl.

| | |
|---|---|
| *A61K 47/68* | (2017.01) |
| *C07K 16/40* | (2006.01) |
| *A61P 35/00* | (2006.01) |
| *A61K 38/07* | (2006.01) |
| *A61K 38/08* | (2019.01) |
| *A61K 31/704* | (2006.01) |
| *C07K 16/28* | (2006.01) |
| *A61K 39/00* | (2006.01) |

(52) U.S. Cl.
CPC ........ *A61K 47/6871* (2017.08); *A61K 31/704* (2013.01); *A61K 38/07* (2013.01); *A61K 38/08* (2013.01); *A61K 47/6803* (2017.08); *A61K 47/6809* (2017.08); *A61K 47/6817* (2017.08); *A61K 47/6849* (2017.08); *A61P 35/00* (2018.01); *C07K 16/2896* (2013.01); *C07K 16/40* (2013.01); *A61K 2039/505* (2013.01); *C07K 2317/53* (2013.01)

(58) Field of Classification Search
CPC .. A61K 47/6801–6833; A61K 47/6871; A61K 47/6849; A61K 47/6817; A61K 47/6809; C07K 2317/53; C07K 16/2896; C07K 16/40; C07K 16/30
See application file for complete search history.

(56) References Cited

U.S. PATENT DOCUMENTS

| | | | |
|---|---|---|---|
| 2008/0305044 A1* | 12/2008 | McDonagh | C07K 16/2878 424/9.1 |
| 2016/0237161 A1 | 8/2016 | De Weers et al. | |
| 2016/0297888 A1* | 10/2016 | Zhou | A61K 39/39558 |

FOREIGN PATENT DOCUMENTS

| | | | | |
|---|---|---|---|---|
| EP | 1914242 A1 | | 4/2008 | |
| WO | WO-2012092616 A1 * | | 7/2012 | ............... A61P 35/00 |
| WO | WO-2013173391 A1 * | | 11/2013 | ............ C07D 207/08 |
| WO | WO-2014011521 A1 * | | 1/2014 | ............... A61K 45/06 |
| WO | WO-2016123412 A1 * | | 8/2016 | ......... C07K 5/06052 |

OTHER PUBLICATIONS

Goldmacherand Kovtun (Therapeutic Delivery, 2011, vol. 2, pp. 397-416) (Year: 2011).*
Blanco-Canosa et al (Journal of the American Chemical Society, 2015, vol. 137, pp. 7197-7209) (Year: 2015).*
International Search Report and Written Opinion relating to International Application No. PCT/IB18/054564, completed Oct. 12, 2018, dated Oct. 24, 2018.

* cited by examiner

*Primary Examiner* — Karen A. Canella
(74) *Attorney, Agent, or Firm* — McNeill Baur PLLC

(57) ABSTRACT

There is disclosed an antibody drug conjugate (ADC) having an IgG antibody that binds to a CD38 target conjugated at a Cys site in the hinge region of an IgG antibody. There is further disclosed a method for treating multiple myeloma comprising providing an effective amount of a CD38 ADC.

16 Claims, 8 Drawing Sheets

Specification includes a Sequence Listing.

* P<0.05, one-way ANOVA compared to Vehicle control group.

CD38 ANTIBODY DRUG CONJUGATE

CROSS REFERENCE TO RELATED APPLICATION

The present patent application claims priority from U.S. provisional patent application 62/522,516 filed 20 Jun. 2017 and U.S. provisional patent application 62/553,438 filed 1 Sep. 2017.

TECHNICAL FIELD

The present disclosure provides an antibody drug conjugate (ADC) having an IgG antibody that binds to a CD38 target conjugated at a Cys site in the hinge region of an IgG antibody. The present disclosure further provides a method for treating a multiple myeloma comprising providing an effective amount of a CD38 ADC.

BACKGROUND

CD38 is a 45 kD type II transmembrane glycoprotein with a long C-terminal extracellular domain and a short N-terminal cytoplasmic domain. The CD38 protein is a bifunctional ectoenzyme that can catalyze the conversion of $NAD^+$ into cyclic ADP-ribose (cADPR) and also hydrolyze cADPR into ADP-ribose. During ontogeny, CD38 appears on $CD34^+$ committed stem cells and lineage-committed progenitors of lymphoid, erythroid and myeloid cells. CD38 expression persists mostly in the lymphoid lineage with varying expression levels at different stages of T and B cell development.

CD38 is upregulated in many hematopoeitic malignancies and in cell lines derived from various hematopoietic malignancies, including non-Hodgkin's lymphoma (NHL), Burkitt's lymphoma (BL), multiple myeloma B chronic lymphocytic leukemia (B-CLL), B and T acute lymphocytic leukemia (ALL), T cell lymphoma (TCL), acute myeloid leukemia (AML), hairy cell leukemia (HCL), Hodgkin's Lymphoma (HL), and chronic myeloid leukemia (CML). On the other hand, most primitive pluripotent stem cells of the hematopoietic system are $CD38^-$. CD38 expression in hematopoietic malignancies and its correlation with disease progression makes CD38 an attractive target for anti-CD38 antibody therapy.

CD38 has been reported to be involved in $Ca^{2+}$ mobilization (Morra et al., 1998, FASEB J., 12: 581-592; Zilber et al., 2000, Proc. Natl. Acad. Sci. USA, 97: 2840-2845) and in the signal transduction through tyrosine phosphorylation of numerous signaling molecules, including phospholipase C-γ, ZAP-70, syk, and c-cbl, in lymphoid and myeloid cells or cell lines (Funaro et al., 1993, Eur. J. Immunol., 23: 2407-2411; Mona et al., 1998, FASEB J., 12: 581-592; Funaro et al., 1990, J. Immunol, 145: 2390-2396; Zubiaur et al., 1997, J Immunol, 159: 193-205; Deaglio et al., 2003, Blood 102: 2146-2155; Todisco et al., 2000, Blood, 95: 535-542; Konopleva et al., 1998, J. Immunol., 161: 4702-4708; Zilber et al., 2000, Proc. Natl. Acad. USA, 97: 2840-2845; Kitanaka et al., 1997, J. Immunol., 159: 184-192; Kitanaka et al., 1999, J. Immunol., 162: 1952-1958; Malone et al., 2001, Int. Immunol., 13: 397-409). CD38 was proposed to be an important signaling molecule in the maturation and activation of lymphoid and myeloid cells during their normal development.

Evidence for the function of CD38 comes from $CD38^{-/-}$ knockout mice, which have a defect in their innate immunity and a reduced T-cell dependent humoral response due to a defect in dendritic cell migration (Partida-Sanchez et al., 2004, Immunity, 20: 279-291; Partida-Sanchez et al., 2001, Nat. Med., 7: 1209-1216). Nevertheless, it is not clear if the CD38 function in mice is identical to that in humans since the CD38 expression pattern during hematopoiesis differs greatly between human and mouse: a) unlike immature progenitor stem cells in humans, similar progenitor stem cells in mice express a high level of CD38 (Randall et al., 1996, Blood, 87:4057-4067; Dagher et al., 1998, Biol. Blood Marrow Transplant, 4:69-74), b) while during the human B cell development, high levels of CD38 expression are found in germinal center B cells and plasma cells (Uckun, 1990, Blood, 76:19.08-1923; Kumagai et al, 1995, J. Exp. Med., 181:1101-1110), in the mouse, the CD38 expression levels in the corresponding cells are low (Oliver et al., 1997, J. Immunol., 158: 108-1115; Ridderstad and Tarlinton 1998, J. Immunol., 160:4688-4695).

Several anti-human CD38 antibodies with different proliferative properties on various tumor cells and cell lines have been described in the literature. For example, a chimeric OKT10 antibody with mouse Fab and human IgG1 Fc mediates antibody-dependent cell-mediated cytotoxicity (ADCC) very efficiently against lymphoma cells in the presence of peripheral blood mononuclear effector cells from either MM patients or normal individuals (Stevenson et al., 1991, Blood, 77:1071-1079). A CDR-grafted humanized version of the anti-CD38 antibody. AT13/5 has been shown to have potent ADCC activity against CD38-positive cell lines. Human monoclonal anti-CD38 antibodies have been shown to mediate the in vitro killing of CD38-positive cell lines by ADCC and/or complement-dependent cytotoxicity (CDC), and to delay the tumor growth in SCID mice bearing MM cell line RPMI-8226 (WO2005/103083 A2). On the other hand, several anti-CD38 antibodies, IB4. SUN-4B7, and OKT10, but not 1B6, AT1, or AT2, induced the proliferation of peripheral blood mononuclear cells (PBMC) from normal individuals (Ausiello et al. 2000, Tissue Antigens, 56:539-547).

Some of the antibodies of the prior art have been shown to be able to trigger apoptosis ire $CD38^+$ B cells. However, they can only do so in the presence of stroma cells or stroma-derived cytokines. An agonistic anti-CD38 antibody (IB4) has been reported to prevent apoptosis of human germinal center (GC) B cells (Zupo et al. 1994, Eur. J. Immunol., 24:1218-1222), and to induce proliferation of KG-1 and HL-60 AML cells (Konopleva et al. 1998, J. Immunol., 161:4702-4708), but induces apoptosis in Jurkat T lymphoblastic cells (Morra et at 1998, FASEB J., 12:581-592). Another anti-CD38 antibody T16 induced apoptosis of immature lymphoid cells and leukemic lymphoblast cells from an ALL patient (Kumagai et al. 1995, J. Exp. Med., 181:1101-1110), and of leukemic myeloblast cells from AML patients (Todisco et al, 2000, Blood, 95:535-542), but T16 induced apoptosis only in the presence of stroma cells or stroma-derived cytokines (IL-7, IL-3, stem cell factor).

Therefore, we believe that antibody drug conjugates (ADCs), targeted with anti-CD38 antibodies, offer the promise and potential of delivering potent anti-tumor activity with the advantage of reduced side effects.

SUMMARY

The present disclosure provides and antibody drug conjugate (ADC) having an IgG antibody that binds to a CD38 target conjugated at Cys sites in the hinge region of an IgG antibody. The present disclosure further provides a method for treating multiple myeloma comprising providing an effective amount of a CD38 ADC.

More specifically, the present disclosure provides an anti-CD38 ADC composition comprising:

(a) an anti-CD38 IgG antibody C38A2 (SEQ ID NOs. 1/2 for heavy/light chain variable regions herein) or C38D8 (SEQ ID NOs. 3/4 for heavy/light chain variable regions herein);

(b) a drug or toxin moiety that is a is a tubulin inhibitor or a doxorubicin analog; and (c) a conjugation linker moiety wherein the conjugation linker moiety binds to single Cys residue in a hinge region of an IgG antibody, and wherein a heavy chain hinge region of an IgG antibody may be mutated such that the heavy chain hinge region contains only one Cys residue.

Preferably, the drug or toxin moiety is selected from the group consisting of D1, D2, D3, D4, D5, and combinations thereof, wherein the structures of D1, D2, D3, D4 and D5 are:

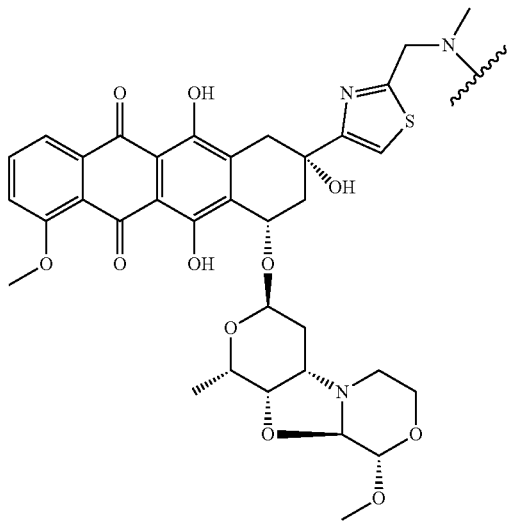

D1

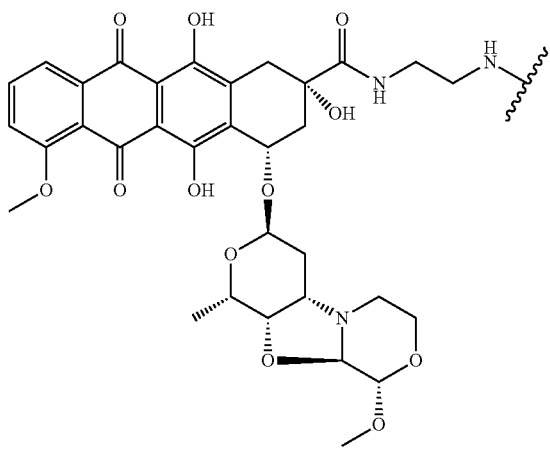

D2

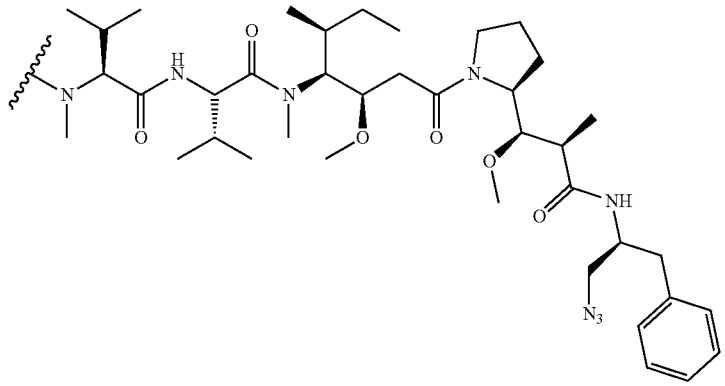

D3

D4
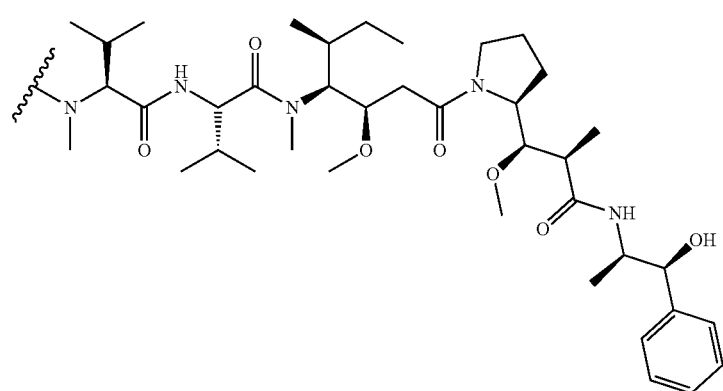
D5
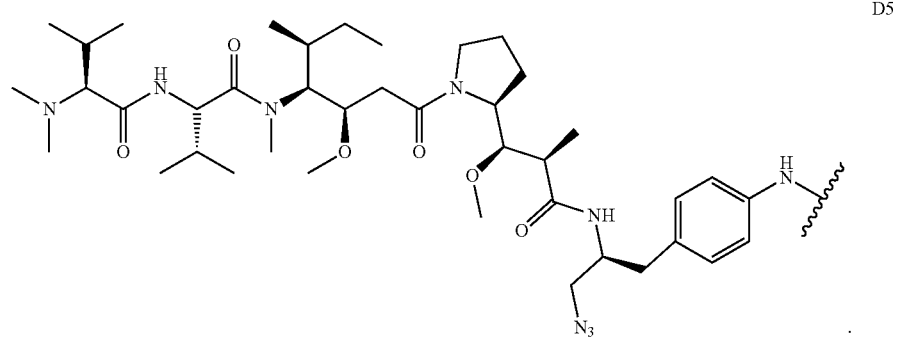
In some embodiments, the conjugation linker moiety comprises a linker moiety and a conjugation moiety. In some embodiments, the conjugation linker moiety comprises one or more of the structures:
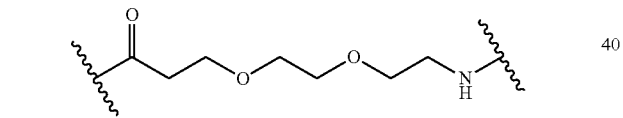
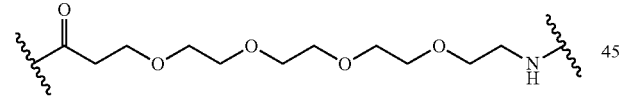
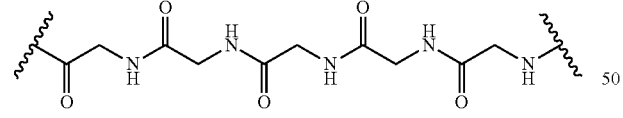
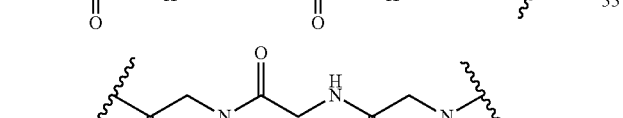
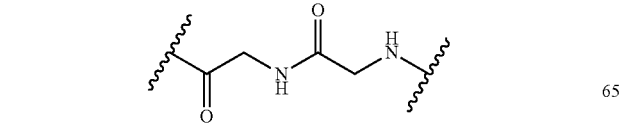
-continued
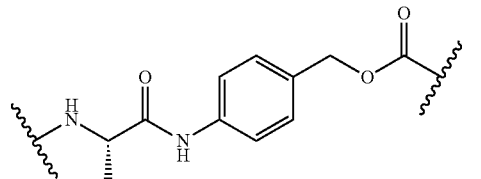
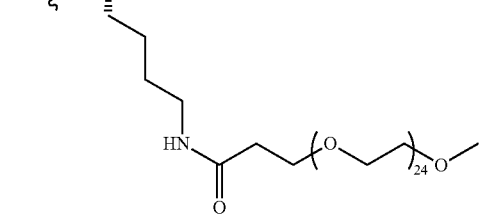
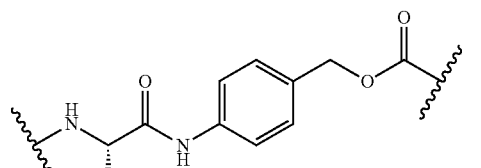
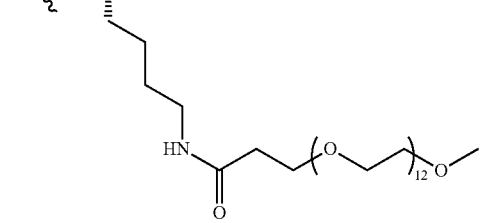

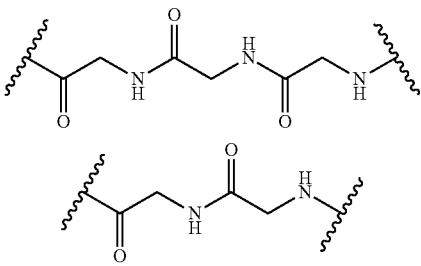

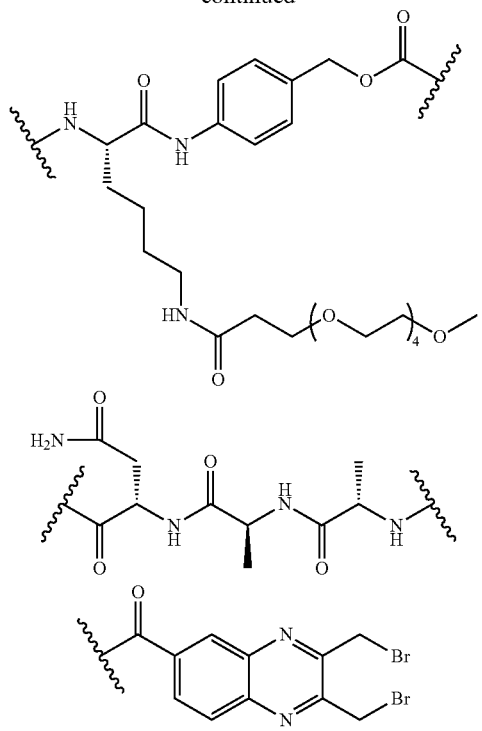

wherein the wavy line indicates a point of attachment to the drug or toxin moiety and to the conjugation moiety. In some embodiments, the conjugation moiety is

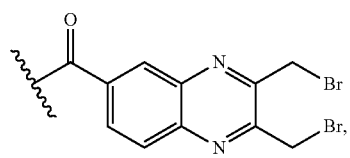 [SMILES: *C(=O)c1ccc2nc(CBr)c(CBr)nc2c1]

wherein the wavy line indicates the point of attachment to the conjugation linker moiety.

Preferably, the conjugation linker moiety is selected from the group consisting of:

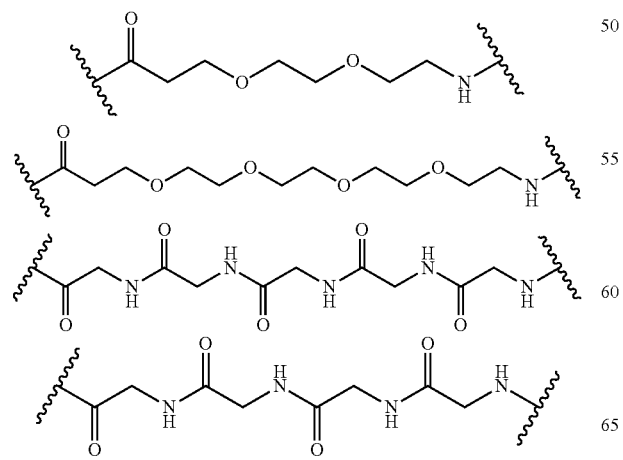

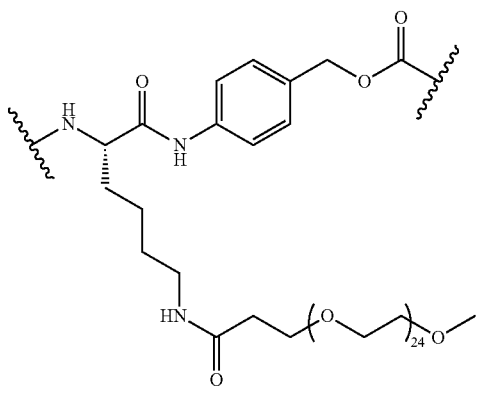

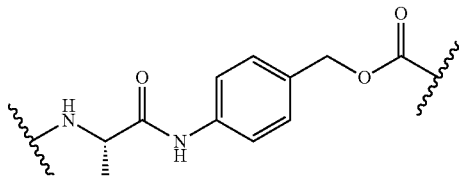

wherein the wavy line indicates a point of attachment.

Preferably, the conjugation moiety is

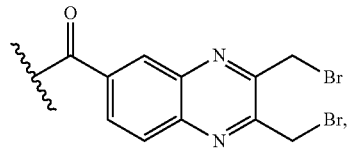 [SMILES: *C(=O)c1ccc2nc(CBr)c(CBr)nc2c1]

wherein the wavy line indicates the point of attachment.

In another aspect is provided an antibody drug conjugate (ADC) composition comprising an IgG antibody that binds to CD38, a linker moiety conjugated to one Cys residue in a hinge region of an IgG antibody mutated to have only one Cys residue, and a toxin moiety conjugated to the linker moiety.

In another aspect is provided an anti-CD38 ADC composition comprising:
(a) an anti-CD38 IgG antibody C38A2-SV (SEQ ID NOs. 1/3 for heavy/light chain variable regions herein) or C38A2 (SEQ ID NOs. 1/2 for heavy/light chain variable regions herein);
(b) a drug or toxin moiety that is a is a tubulin inhibitor or a doxorubicin analog; and
(c) a conjugation linker moiety, wherein the conjugation linker comprises a linker and a conjugation moiety which covalently binds to a single Cys residue in a hinge region of an IgG antibody, and wherein a heavy chain hinge region of an IgG antibody may be mutated such that the heavy chain hinge region contains only one Cys residue.

In some embodiments, the drug or toxin moiety is selected from the group consisting of D1, D2, D3, D4, D5, and combinations thereof, wherein the structures of D1, D2, D3, D4 and D5 are:

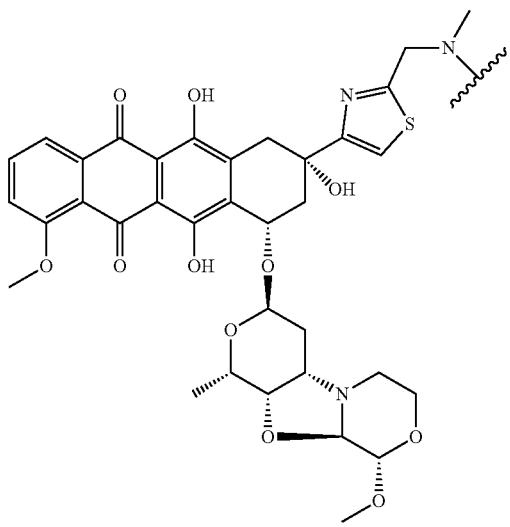

D1

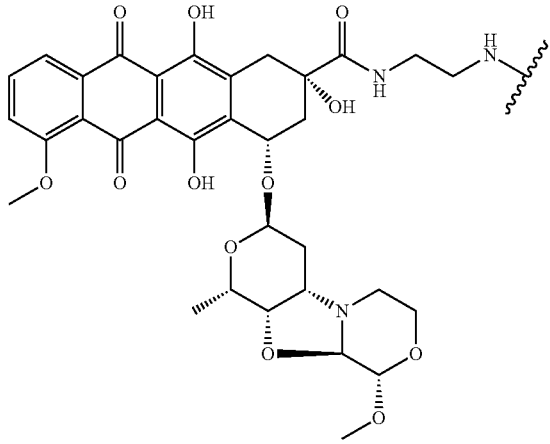

D2

D3
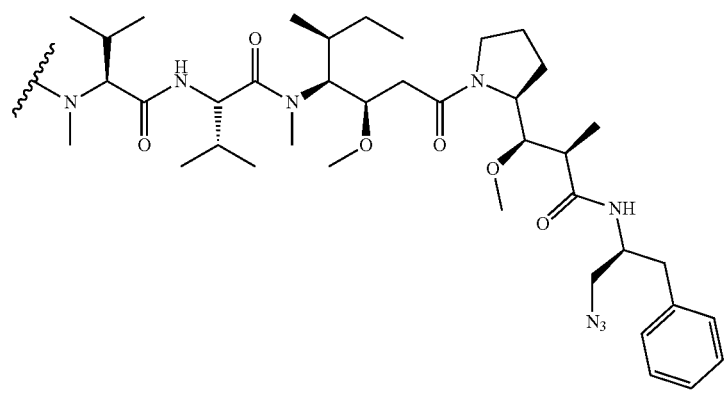
D4
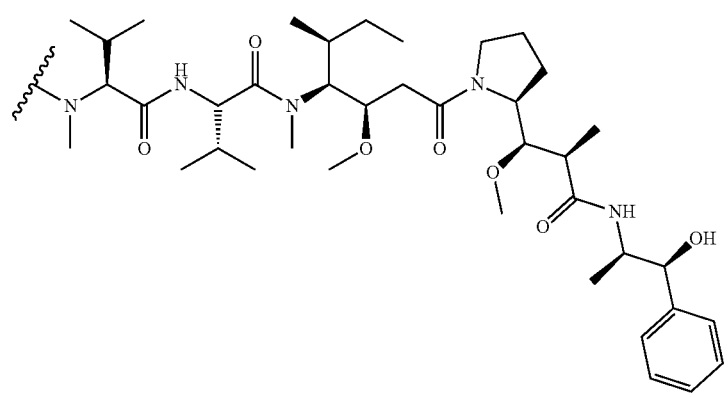
D5
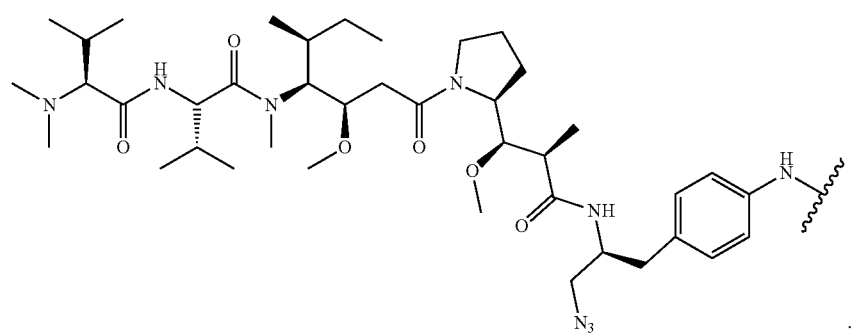

In some embodiments, the linker is selected from the group consisting of:

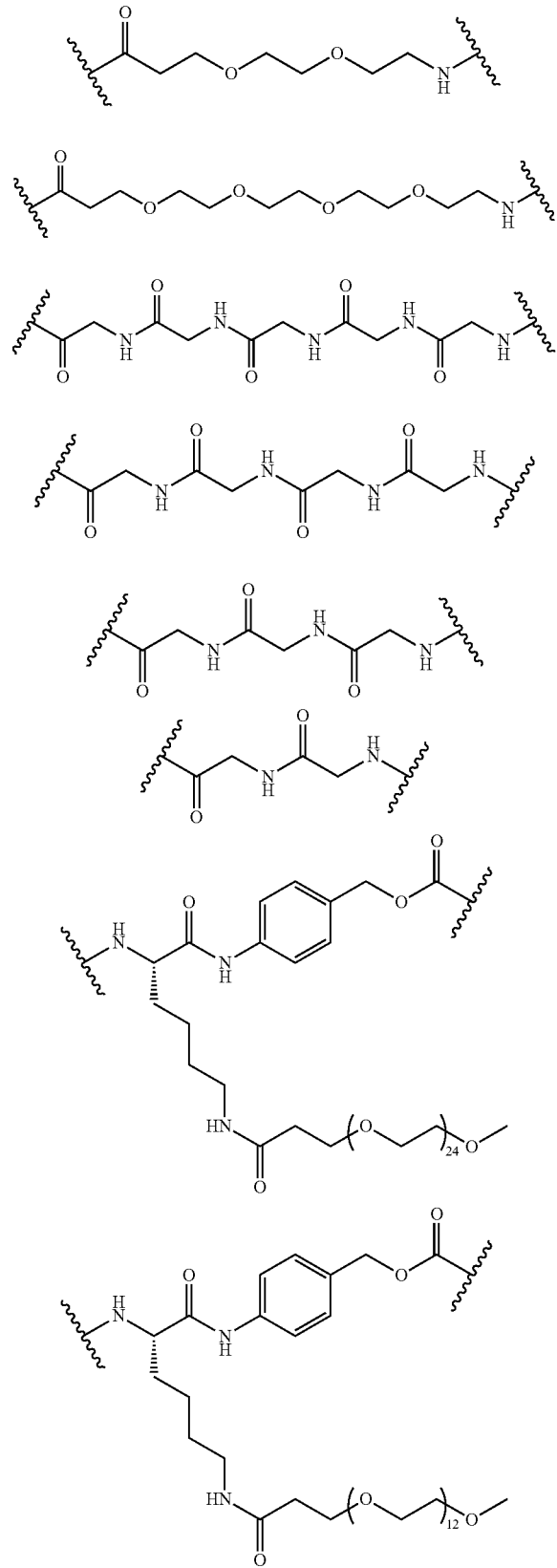

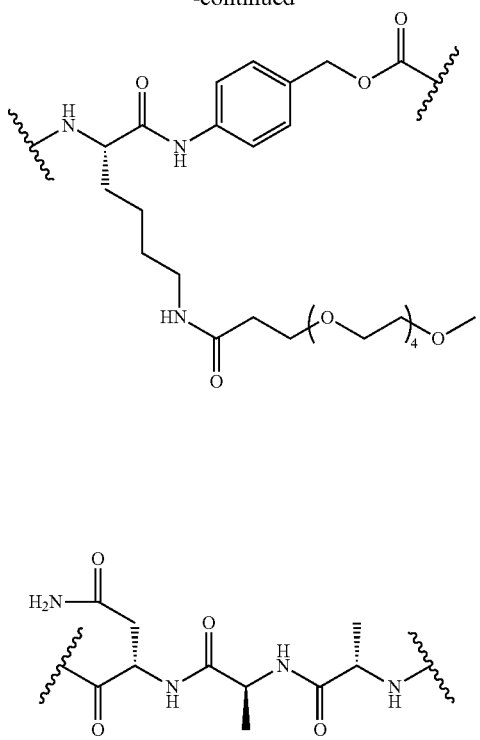

wherein the wavy line indicates a point of attachment to the conjugation moiety and the drug or toxin moiety.

In some embodiments, the conjugation moiety is

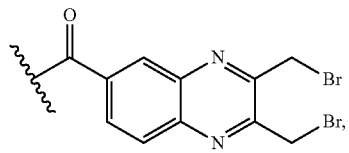 [SMILES: *C(=O)c1ccc2nc(CBr)c(CBr)nc2c1]

wherein the wavy line indicates the point of attachment to the linker.

The present disclosure further provides a method for treating multiple myeloma, comprising administering an effective amount of an anti-CD38 ADC composition comprising:

(a) an anti-CD38 IgG antibody C38A2 (SEQ ID NOs. 1/2 for heavy/light chain variable regions herein) or C38D8 (SEQ ID NOs. 3/4 for heavy/light chain variable regions herein);

(b) a drug or toxin moiety that is a is a tubulin inhibitor or a doxorubicin analog; and (c) a conjugation linker moiety wherein the conjugation linker moiety binds to single Cys residue in a hinge region of an IgG antibody, and wherein a heavy chain hinge region of an IgG antibody may be mutated such that the heavy chain hinge region contains only one Cys residue.

Preferably, the drug or toxin moiety is selected from the group consisting of D1, D2, D3, D4, D5, and combinations thereof, wherein the structures are:
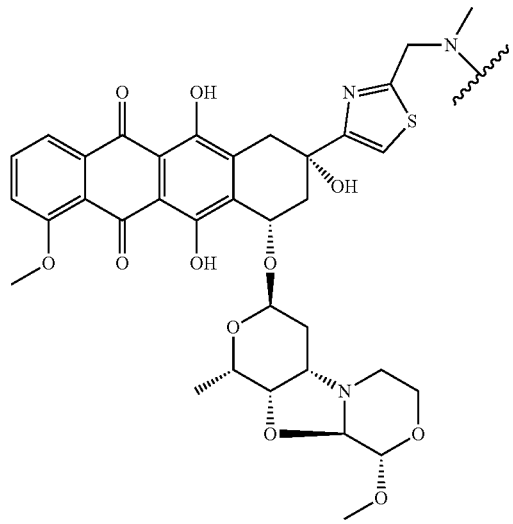
D1
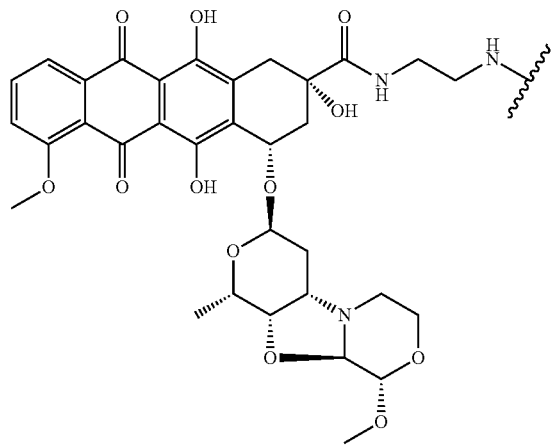
D2
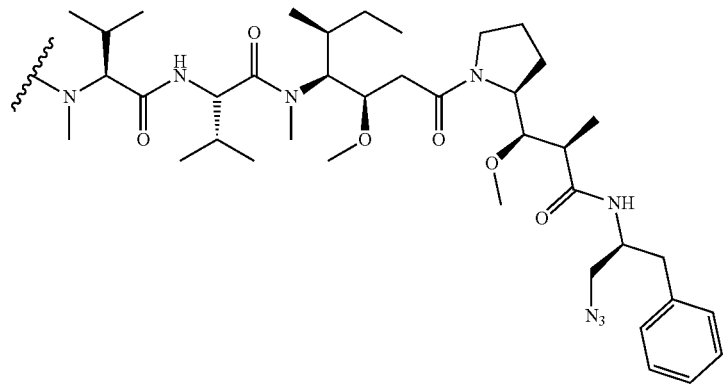
D3

D4
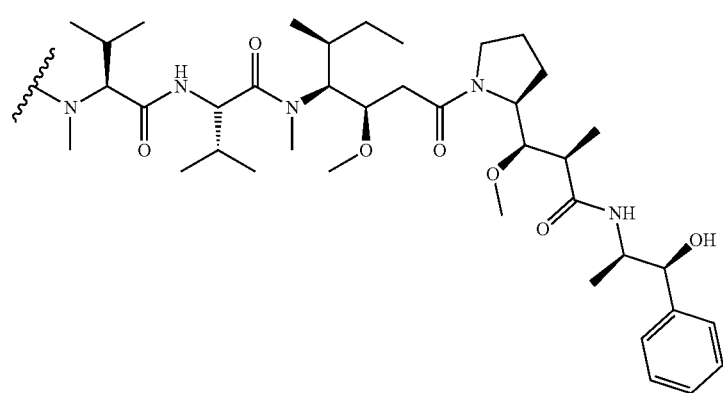
D5
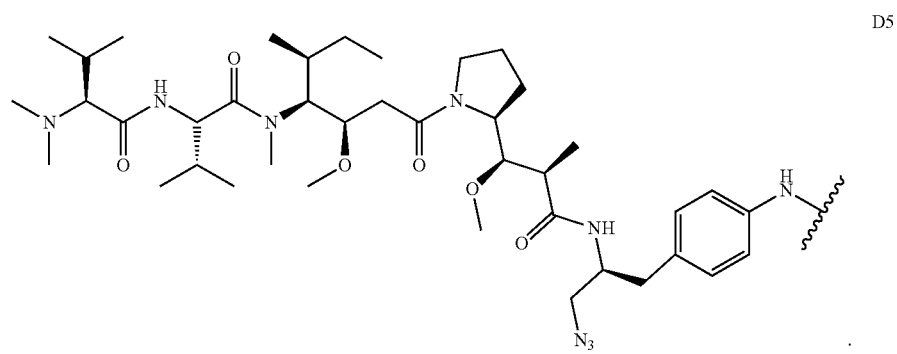
In some embodiments, the conjugation linker moiety comprises a linker moiety and a conjugation moiety. In some embodiments, the conjugation linker moiety comprises one or more of the structures:
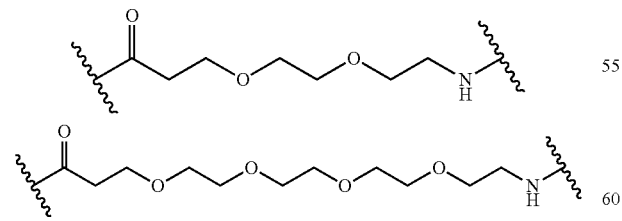
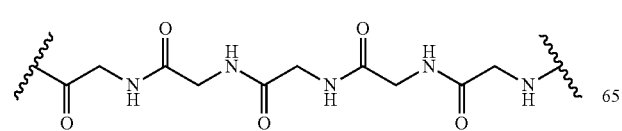
-continued
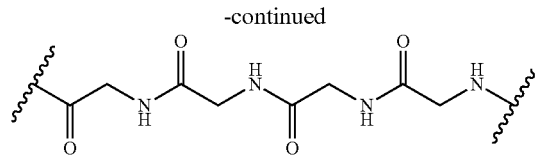
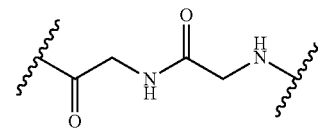

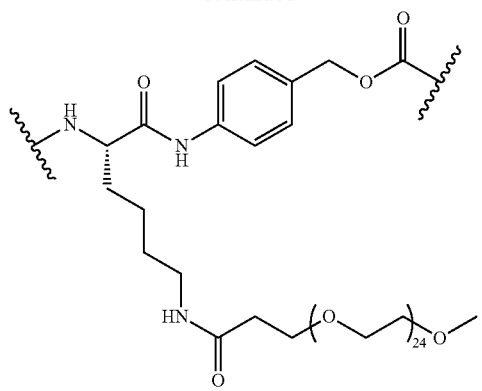
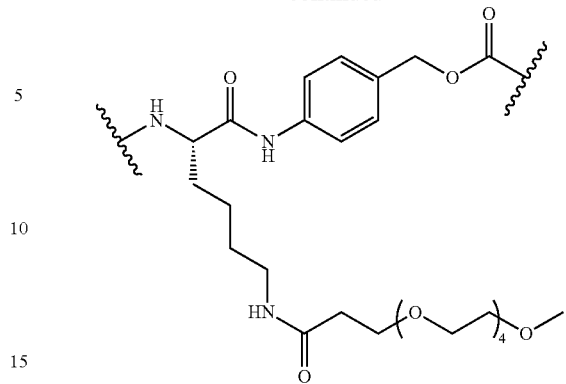
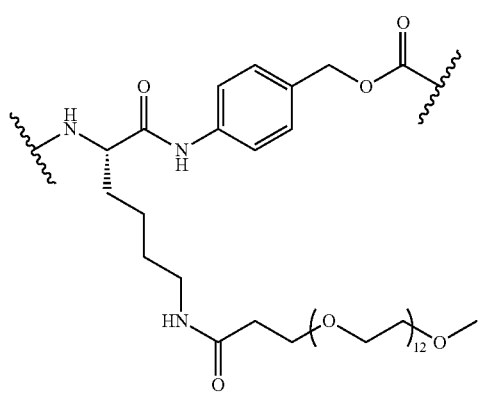
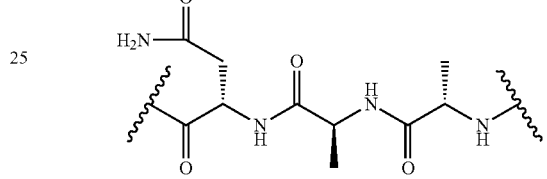
wherein the wavy line indicates a point of attachment to the drug or toxin moiety and to the conjugation moiety. In some embodiments, the conjugation moiety is
D1
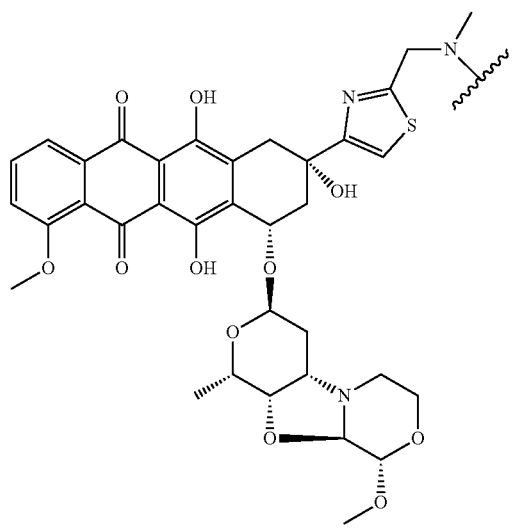

D2
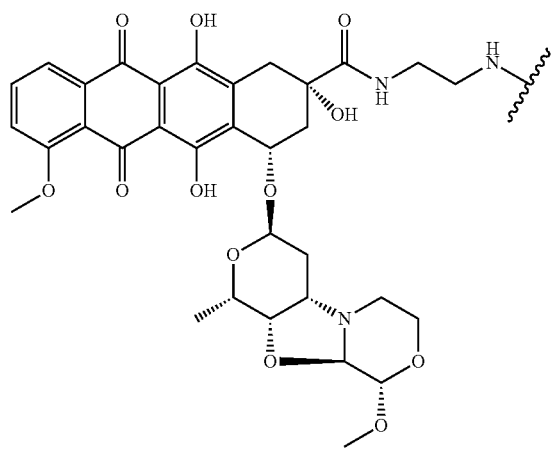
D3
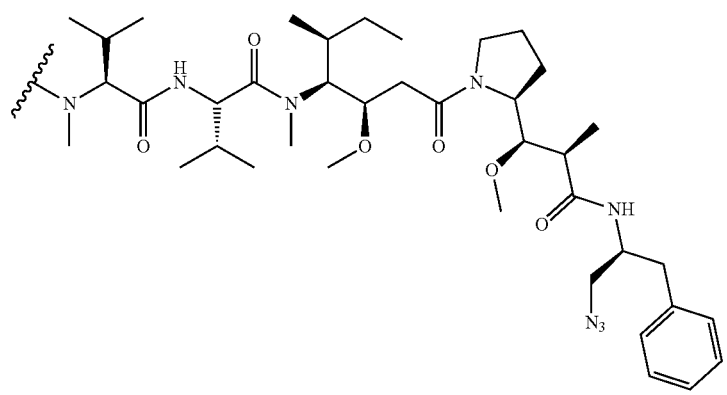
D4
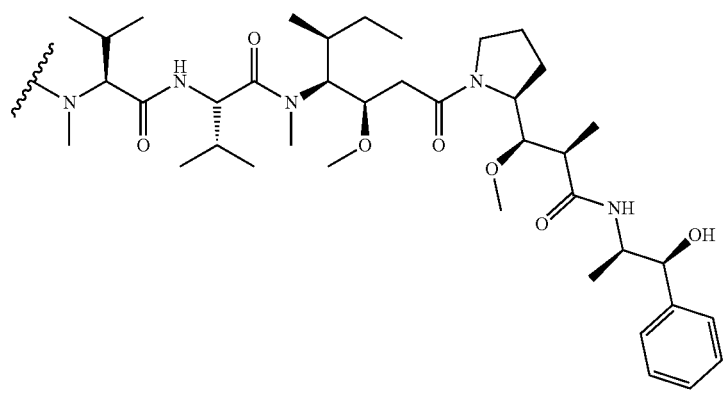
D5
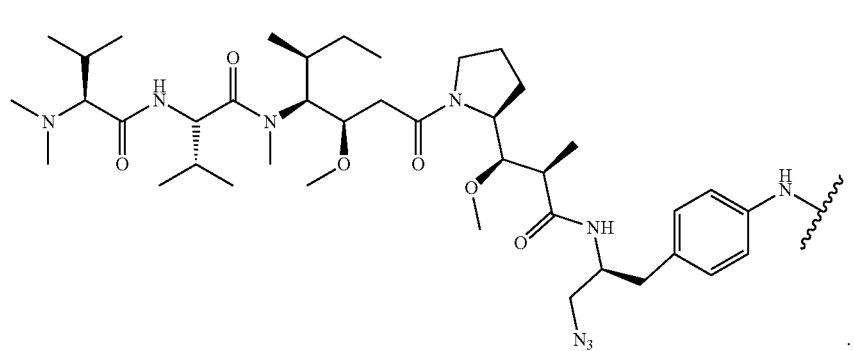

wherein the wavy line indicates the point of attachment to the conjugation linker moiety. Preferably, the linker moiety of the conjugation linker moiety is selected from the group consisting of:

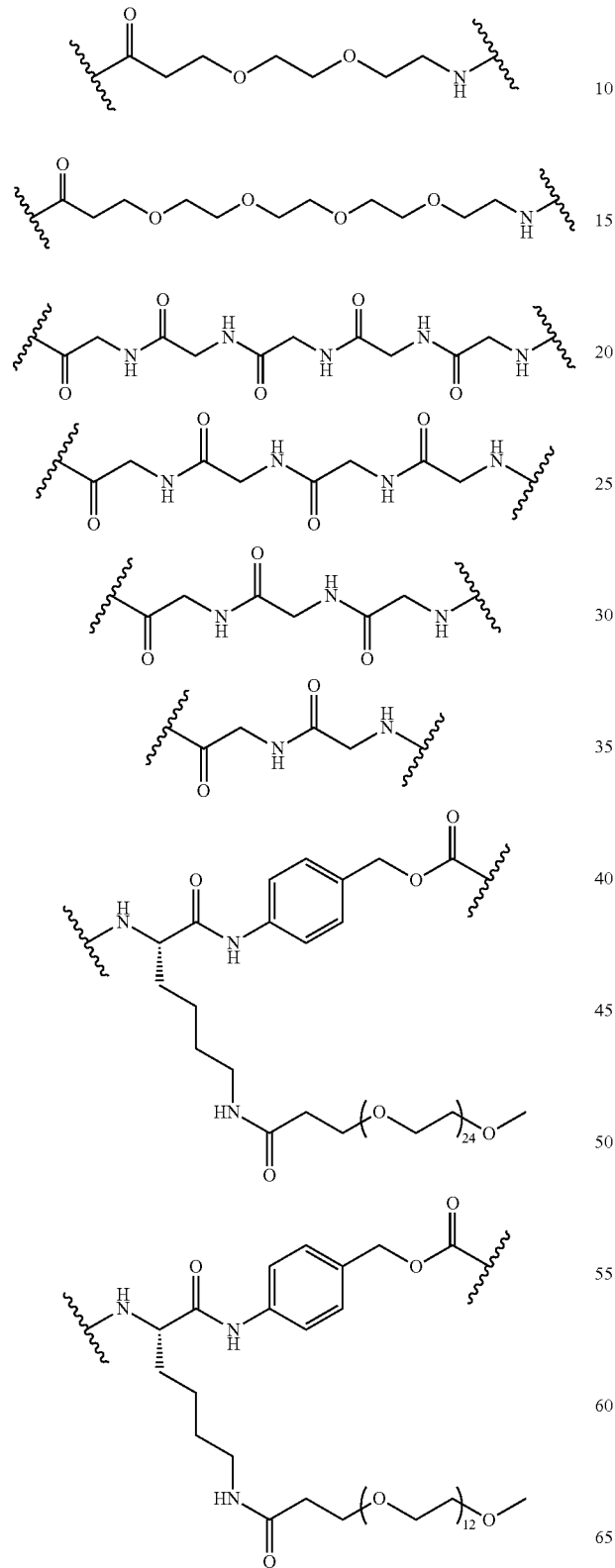

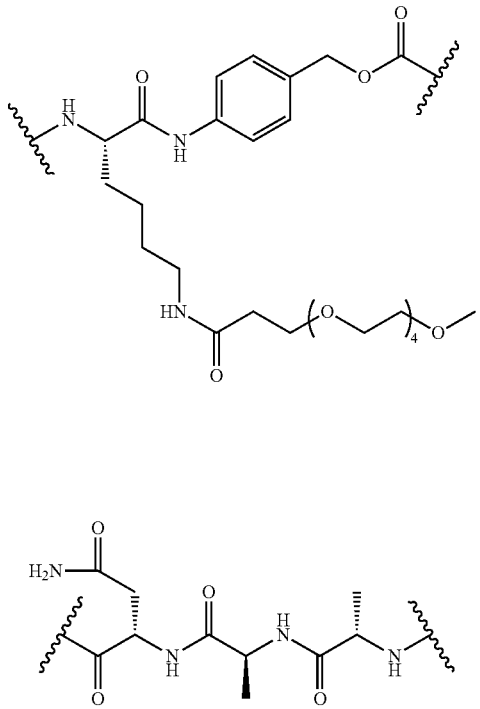

wherein the wavy line indicates a point of attachment.

Preferably, the conjugation moiety is

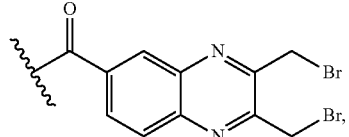

wherein the wavy line indicates the point of attachment.

In another aspect is provided a method for treating multiple myeloma comprising providing a therapeutically effective amount of an anti-CD38 ADC composition comprising:

(a) an anti-CD38 IgG antibody C38A2-SV (SEQ ID NOs. 1/3 for heavy/light chain variable regions herein) or C38A2 wild type (SEQ ID NOs. 1/2 for heavy/light chain variable regions herein);

(b) a drug or toxin moiety that is a is a tubulin inhibitor or a doxorubicin analog; and (c) a conjugation linker moiety, wherein the conjugation linker comprises a linker and a conjugation moiety which covalently binds to a single Cys residue in a hinge region of an IgG antibody, and wherein a heavy chain hinge region of an IgG antibody may be mutated such that the heavy chain hinge region contains only one Cys residue.

In some embodiments, the drug or toxin moiety is selected from the group consisting of D1, D2, D3, D4, D5, and combinations thereof, wherein the structures are:

D1
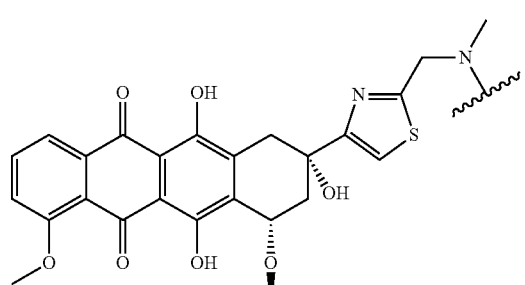
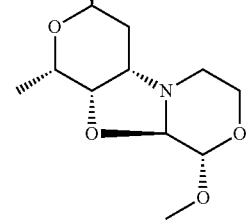
D2
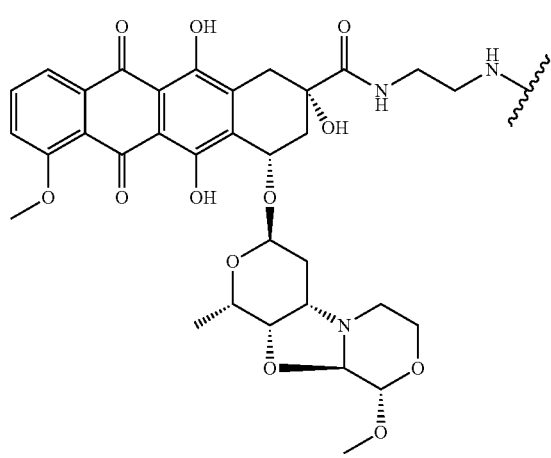
D3
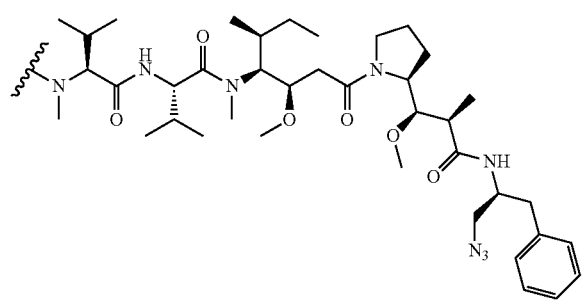
D4
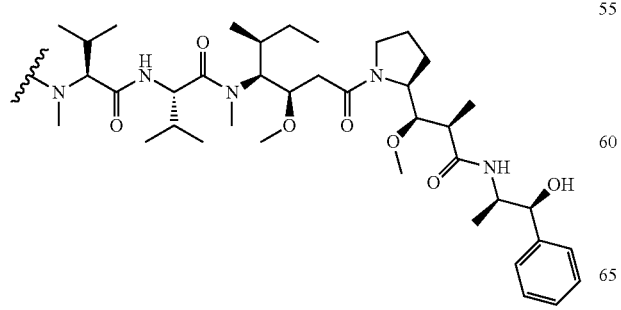
D5
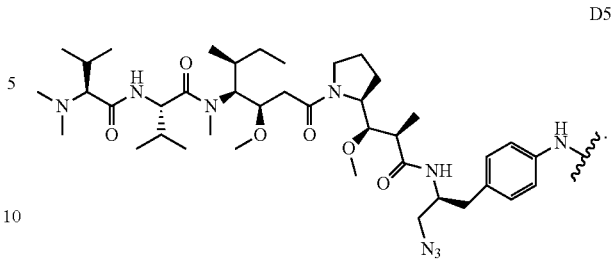
In some embodiments, the linker is selected from the group consisting of:
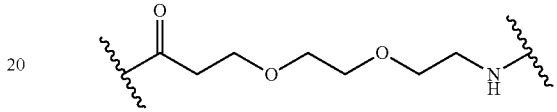
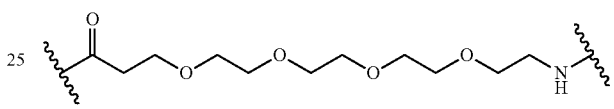
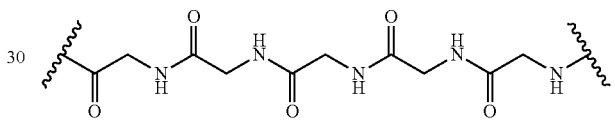
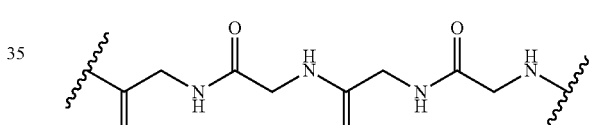
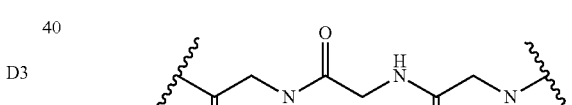
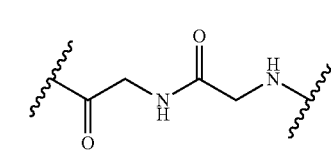
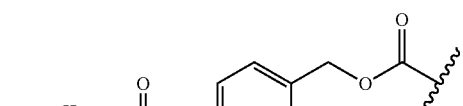
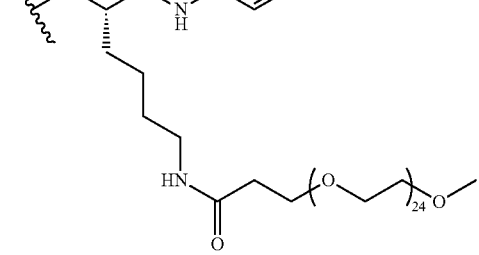

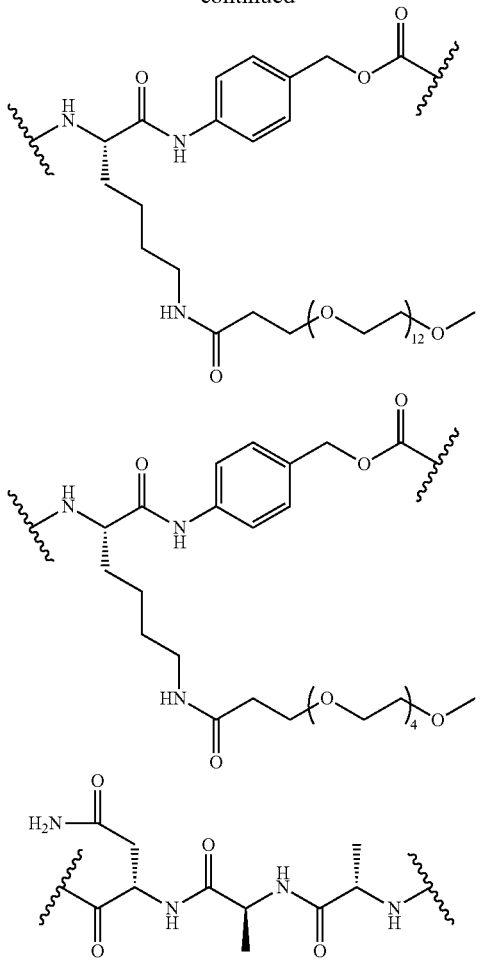

wherein the wavy line indicates a point of attachment to the conjugation moiety and the drug or toxin moiety.

In some embodiments, the conjugation moiety is

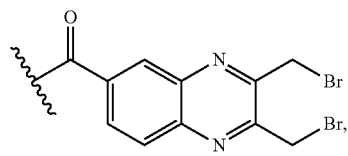 [SMILES: *C(=O)c1ccc2nc(CBr)c(CBr)nc2c1]

wherein the wavy line indicates the point of attachment to the linker.

Preferably, the antibody moiety is a variant of the CD38A2 wild type antibody disclosed and claimed in U.S. Ser. No. 15/094,384, filed 8 Apr. 2016, the disclosure of which is incorporated by reference herein. The CD38A2 wild type variable region sequence is disclosed herein as heavy chain SREQ ID NO. 1 and light chain SEQ ID NO. 2. More specifically, the variant sequence alters the second and third amino acids from the N terminus of the light chain variable region. Preferably, the antibody moiety comprises CD38A2-SV (SV variant) having heavy chain SEQ ID NO. 1 and light chain SEQ ID NO. 3. The

DETAILED DESCRIPTION

Figure 1A:
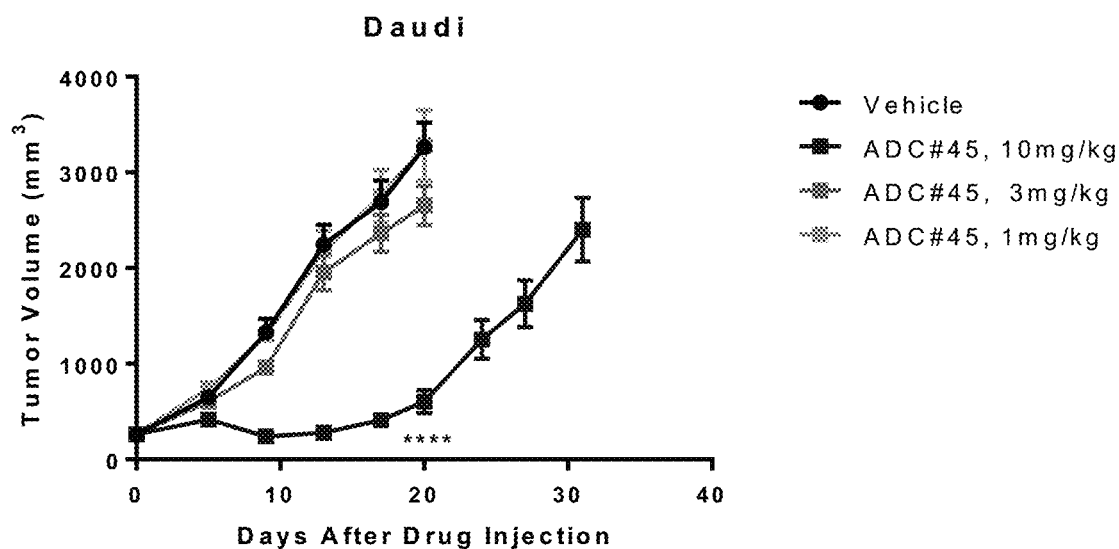
FIG. 1A shows an in vivo study of anti-CD38 ADCs on Burkitt lymphoma model. In the study, 10 million of Daudi cells were injected s.c. to Nu Nu mice. ADC #45 was iv injected to tumor bearing mice after the average tumor volume reached 200 mm$^3$.

The present disclosure provides antibody drug conjugates containing a novel human anti-CD38 antibody (A2) (described in United States Patent application 2016/0297888 Ser. No. 15/094,384 filed 8 Apr. 2016, the disclosure of which is incorporated by reference herein) with toxin moieties described herein including a tubulin inhibitor or a DNA damaging agent, such as doxorubicin analogs. The ADC conjugates retained binding affinity and showed potent cell killing in a variety of CD38 positive cell lines and in vivo.

The present disclosure provides an antibody drug conjugate (ADC) composition comprising an IgG antibody that binds to CD38, a conjugation linker moiety that binds to single Cys residue in the hinge region of an IgG antibody, wherein the hinge region may be mutated such that the heavy chain hinge region contains only one Cys residue and not two, and a toxin moiety selected from the group consisting of derivatives of anthracyclines and Dolastatins. Preferably, the toxin moiety is a tubulin inhibitor or a doxorubicin analog. Preferably, the antibody is an IgG antibody called human C38A2 (heavy/light SEQ ID NOs 3/4 in US patent application 2016/0297888 or SEQ ID NOs. 1/2 for heavy/light chain variable regions herein) family or is a C38D8 (heavy/light SEQ ID NOs 21/22 in US patent application 2016/0297888 or SEQ ID NOs. 3/4 for heavy/light chain variable regions herein). Preferably, the conjugated toxin with linker structure is selected from the group consisting of:

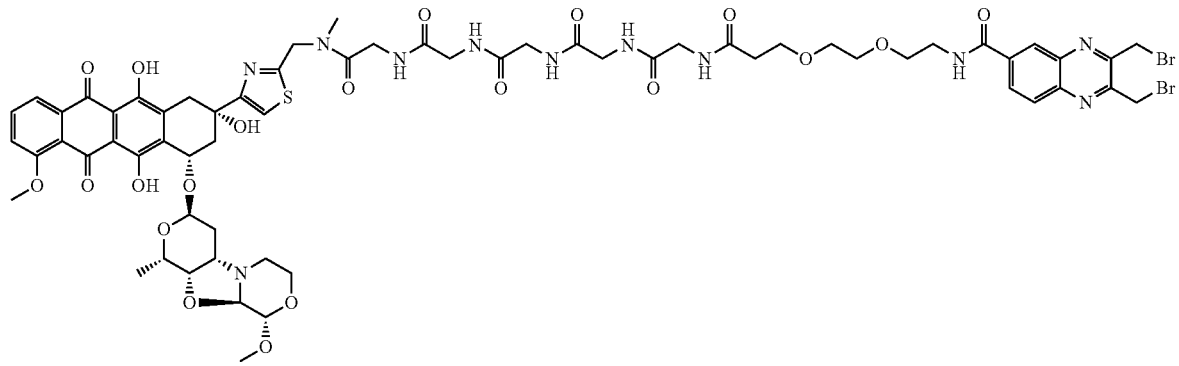

18

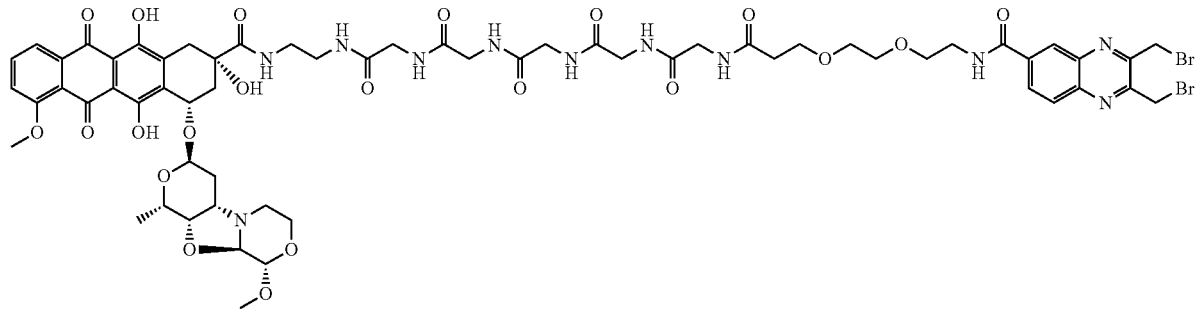

22

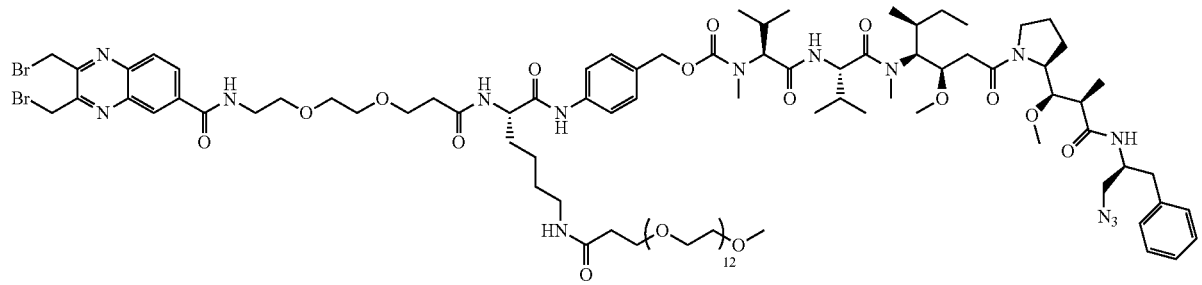

27

31

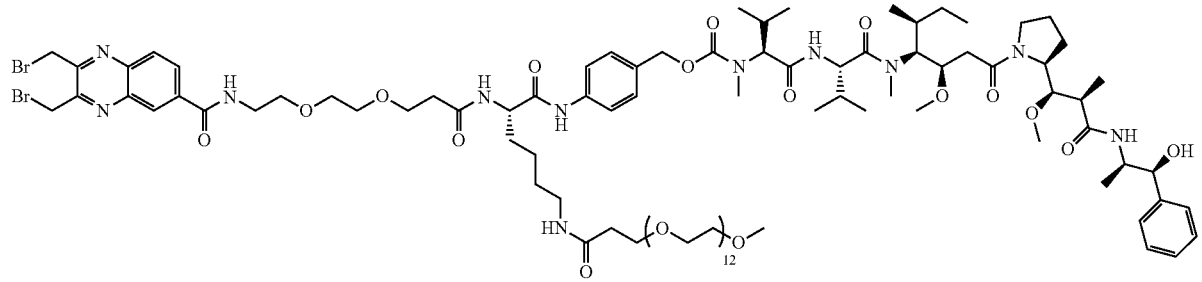

34

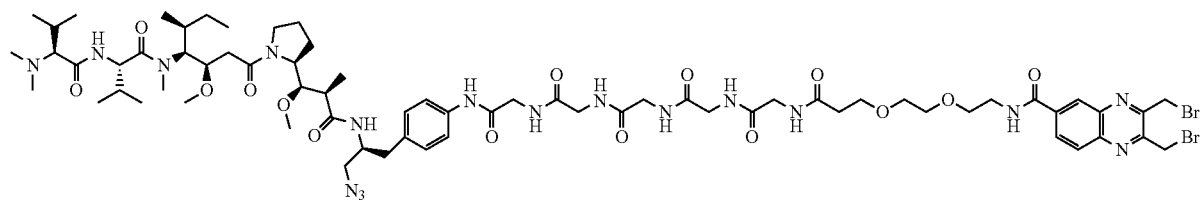

39

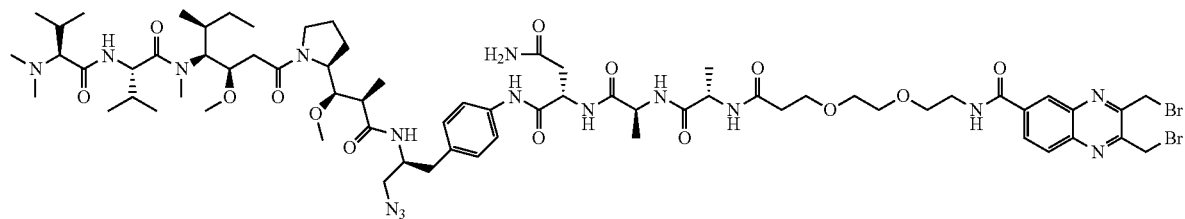

52

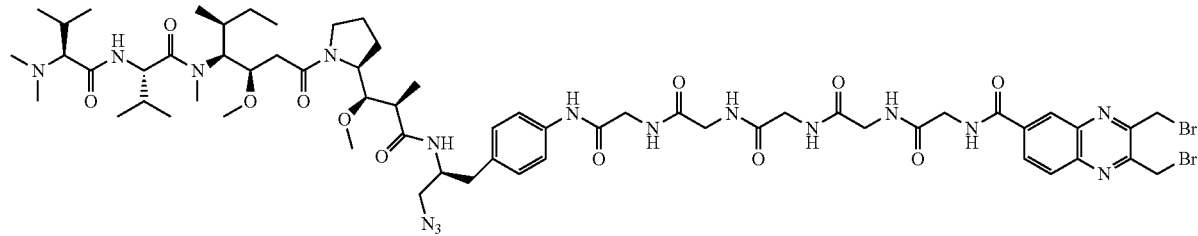

The present disclosure provides a method for treating multiple myeloma, comprising administering an effective amount of an antibody drug conjugate (ADC) composition comprising an IgG antibody that binds to CD38, a conjugation linker moiety that binds to Cys residues in the hinge region of an IgG antibody and to a toxin moiety. By "binds to Cys residues" it is meant that the conjugation linker moiety may be covalently bound to the sulfur atoms of Cys residues in the hinge region of the IgG antibody. Preferably, the toxin moiety is a tubulin inhibitor or a doxorubicin analog. Preferably, the antibody is an IgG antibody called human C38A2 (heavy/light SEQ ID NOs 3/4 in US patent application 2016/0297888 or SEQ ID NOs. 1/2 for heavy/light chain variable regions herein) family or is a C38D8 (heavy/light SEQ ID NOs 21/22 in US patent application 2016/0297888 or SEQ ID NOs. 3/4 for heavy/light chain variable regions herein). One of skill will recognize that toxin moieties as disclosed herein, conjugated to a linker and a conjugation moiety as disclosed herein, represent intermediate toxin linker conjugates, which, when covalently bound (conjugated to) the IgG antibody as disclosed herein, are ADCs as disclosed herein. Preferably, the conjugated toxin with linker structure is selected from the group consisting of (with each compound number indicated):

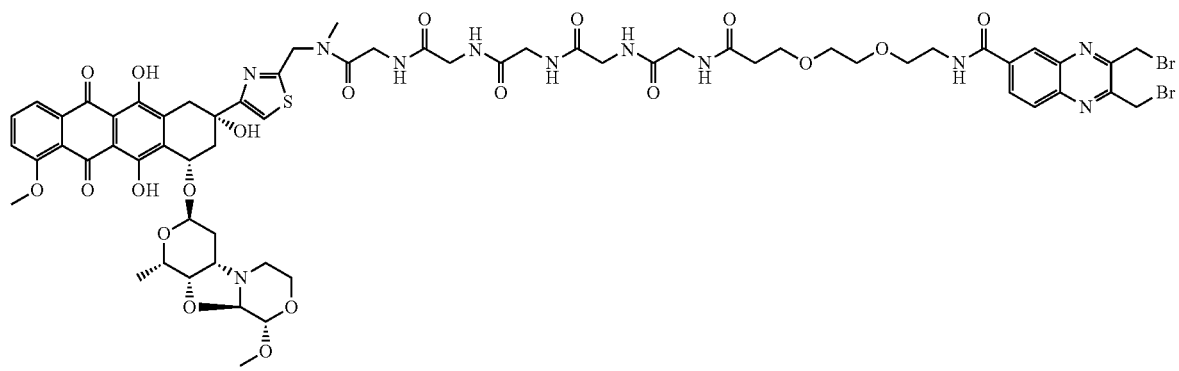
18
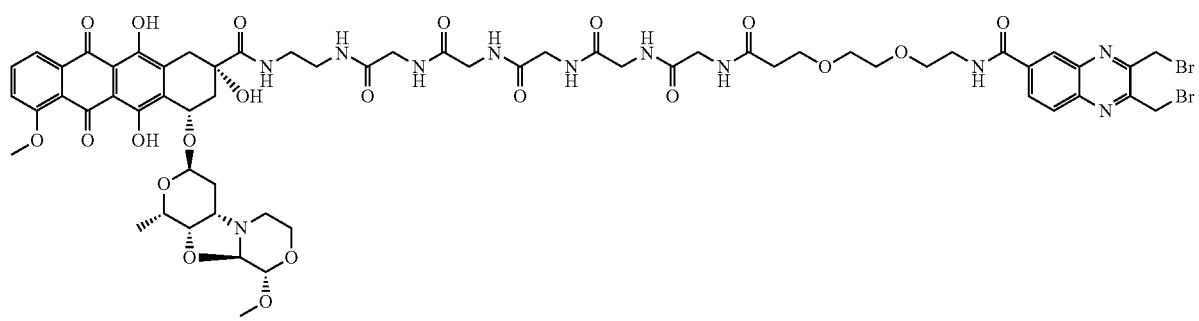
22
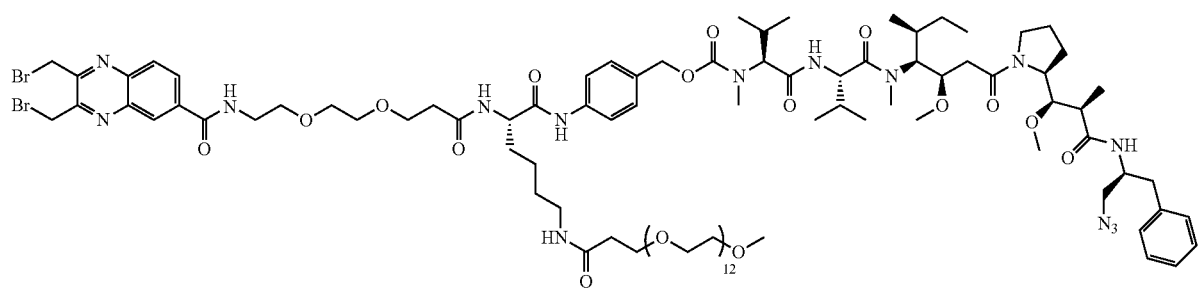
27
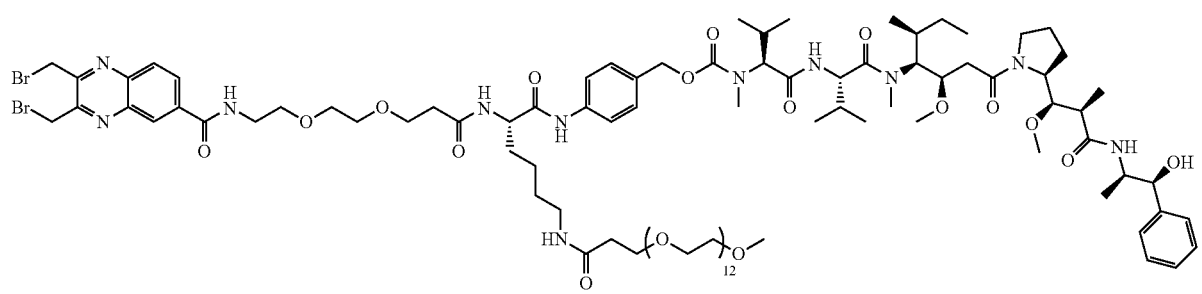
31
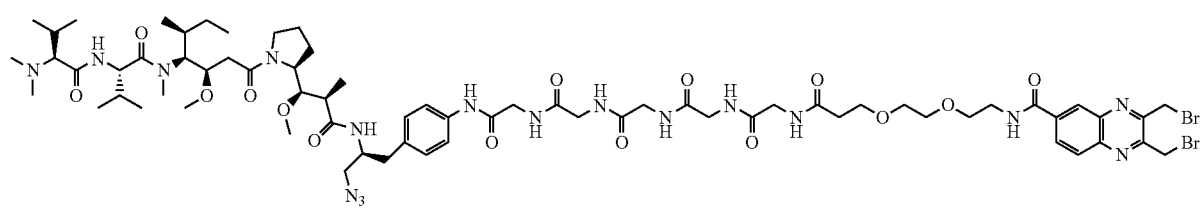
34

-continued

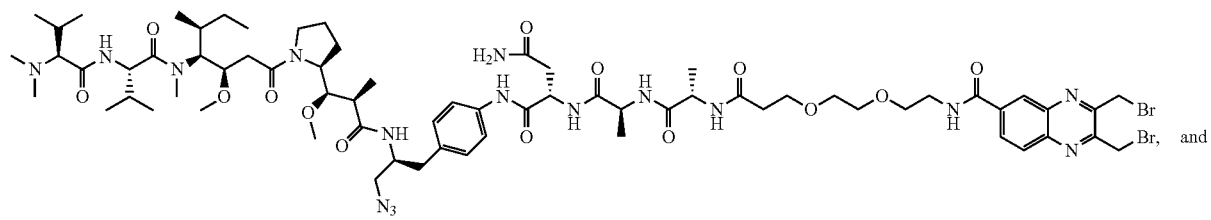
39

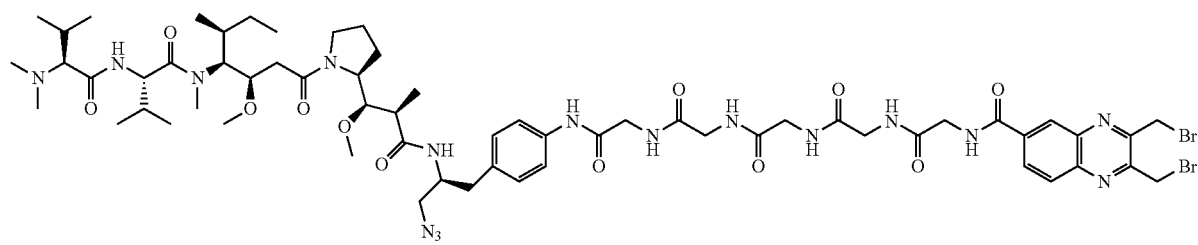
and
52

| Entry | Cytotoxic agent (D) | Linker (L2) | Conjugation method (L1) |
|---|---|---|---|
| D1 | ![structure] | —C(=O), Gly, Ser, Thr, beta-Ala, —(CH$_2$CH$_2$O)$_n$—, or combinations thereof, wherein n is an integer from 1 to 24. | ![structure] |
| D2 | ![structure] | —C(=O), Gly, Ser, Thr, beta-Ala, —(CH$_2$CH$_2$O)$_n$—, and combinations thereof, wherein n is an integer from 1 to 24. | |
| D3 | ![structure] | —C(=O), —(CH$_2$CH$_2$O)$_n$—, Val, Phe, Lys, PAB, or combinations thereof, wherein n is an integer from 1 to 24 | |

| Entry | Cytotoxic agent (D) | Linker (L2) | Conjugation method (L1) |
|---|---|---|---|
| D3 | 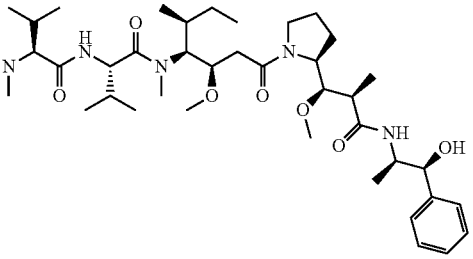 [SMILES: CC[C@H](C)[C@@H]([C@@H](CC(=O)N1CCC[C@H]1[C@H](OC)[C@@H](C)C(=O)N[C@H](C)[C@@H](O)c1ccccc1)OC)N(C)C(=O)[C@@H](NC(=O)[C@@H](NC)C(C)C)C(C)C] | —C(=O), —(CH$_2$CH$_2$O)$_n$—, Val, Phe, Lys, PAB, or combinations thereof, wherein n is an integer from 1 to 24 | |
| D4 | 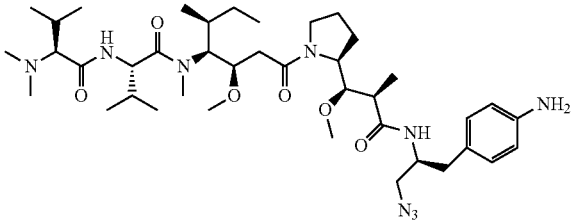 [SMILES: CC[C@H](C)[C@@H]([C@@H](CC(=O)N1CCC[C@H]1[C@H](OC)[C@@H](C)C(=O)N[C@H](CN=[N+]=[N-])Cc1ccc(N)cc1)OC)N(C)C(=O)[C@@H](NC(=O)[C@H](C(C)C)N(C)C)C(C)C] | —C(=O), Gly, Ser, Thr, beta-Ala, —(CH$_2$CH$_2$O)$_n$—, or combinations thereof, wherein n is an integer from 1 to 24 | |
| D5 | 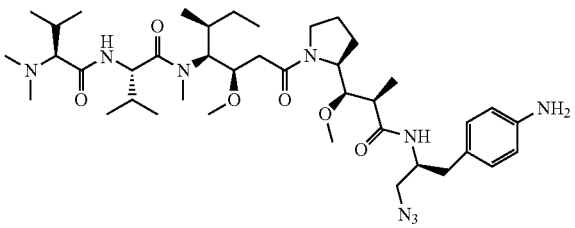 [SMILES: CC[C@H](C)[C@@H]([C@@H](CC(=O)N1CCC[C@H]1[C@H](OC)[C@@H](C)C(=O)N[C@H](CN=[N+]=[N-])Cc1ccc(N)cc1)OC)N(C)C(=O)[C@@H](NC(=O)[C@H](C(C)C)N(C)C)C(C)C] | —C(=O), —(CH$_2$CH$_2$O)$_n$—, PAB, Val-Cit-PAB, Val-Ala-PAB, Ala-Ala-Asn-PAB, or combinations thereof, wherein n is an integer from 1 to 24 | |

Toxin moieties (D): D1 and D2 are anthracycline derivatives. D3, D4, and D5 are tubulin inhibitors.

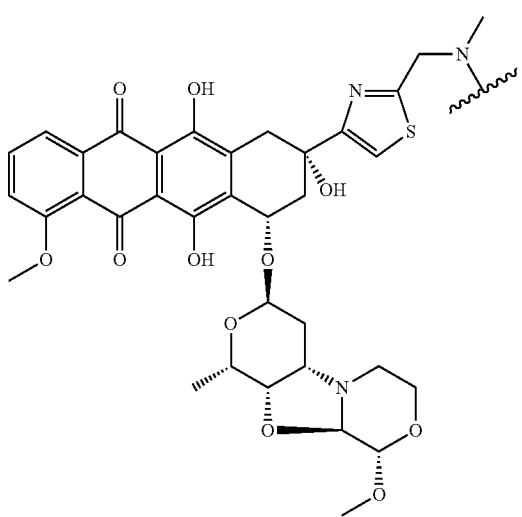

D1

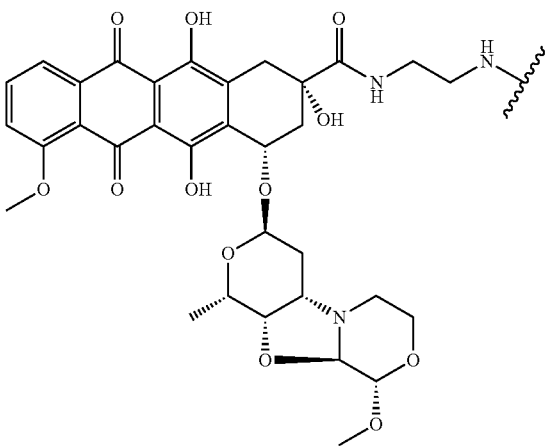

D2

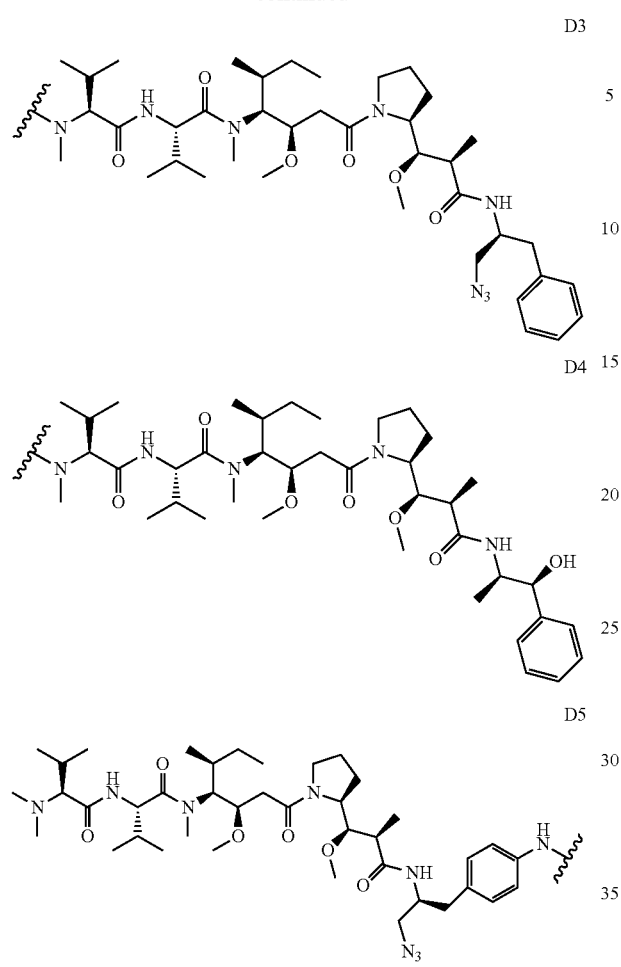
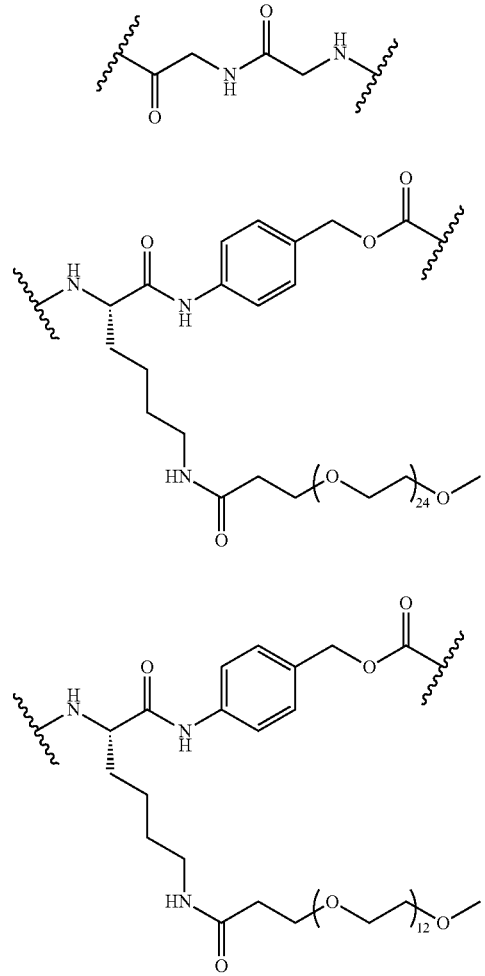
Linker Moieties (L2):
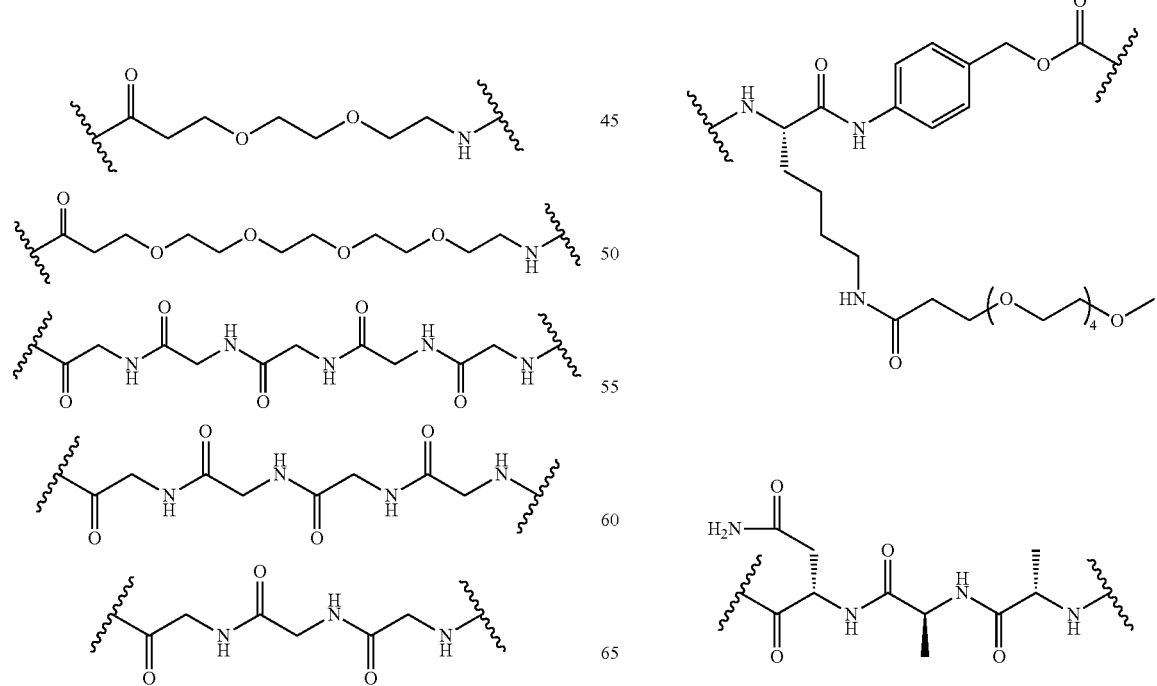

Conjugation Method (L1)

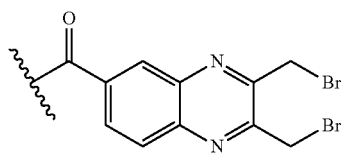 [SMILES: *C(=O)c1ccc2nc(CBr)c(CBr)nc2c1]

The wavy line indicates the point of attachment to the linker.

In some embodiments, the drug linker conjugate comprises a linker L2 and a conjugation moiety, wherein the linker L2 is covalently bound to the conjugation moiety; the conjugation moiety is capable of reacting with free cysteine thiol groups in the hinge region of an IgG antibody. In some embodiments, the conjugation moiety has the structure

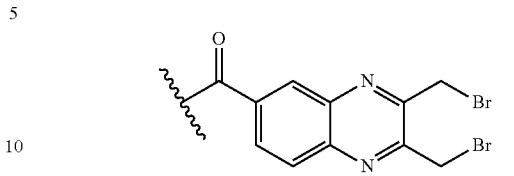

("conjugation method L1").

Examples of Drug Linker Conjugates:

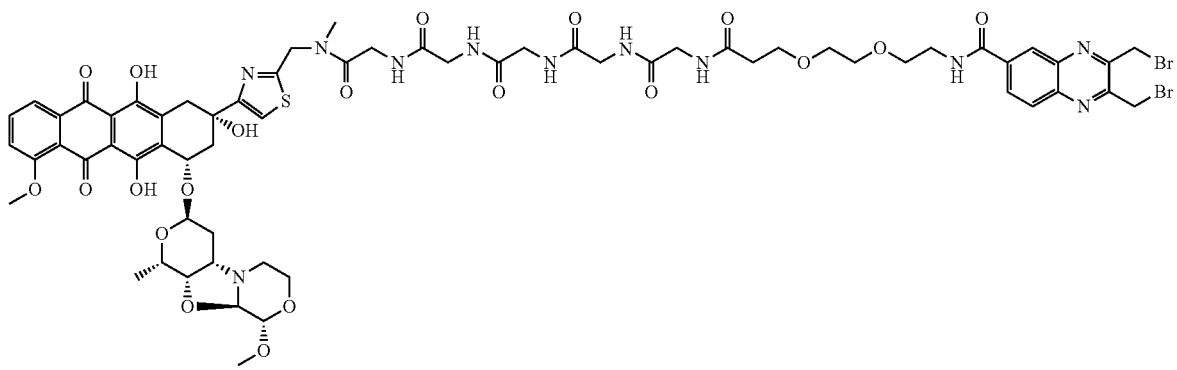

18

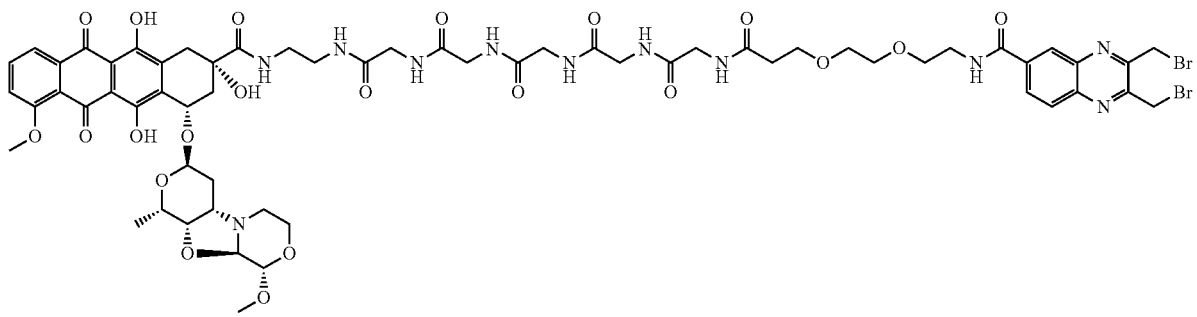

22

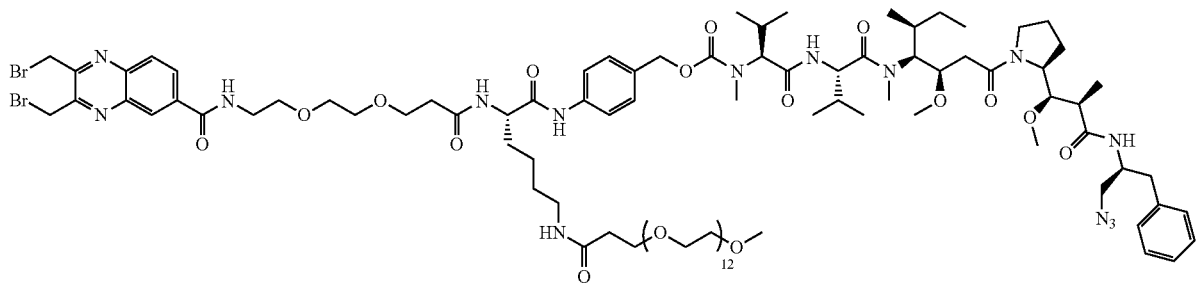

27

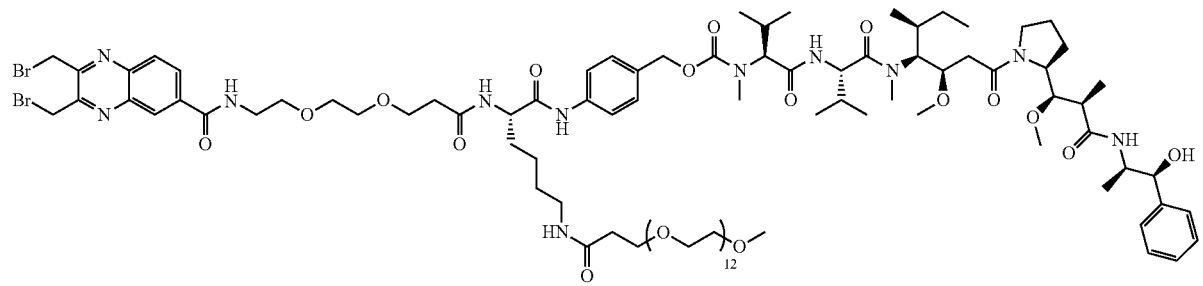
31
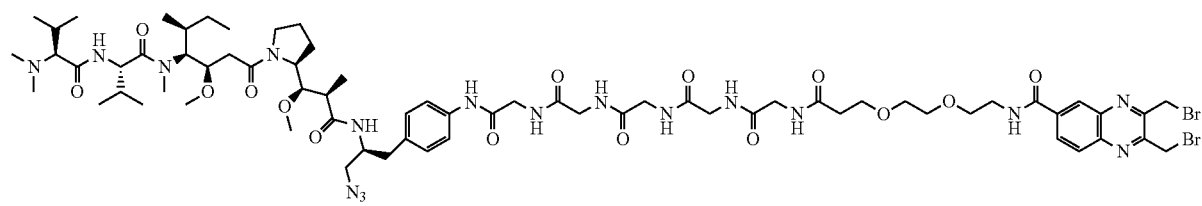
34
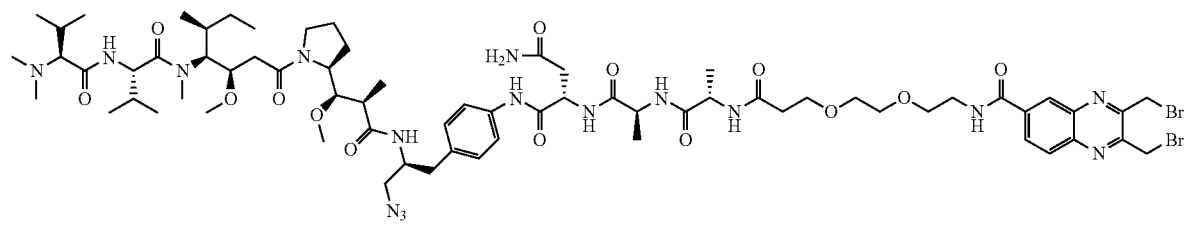
39
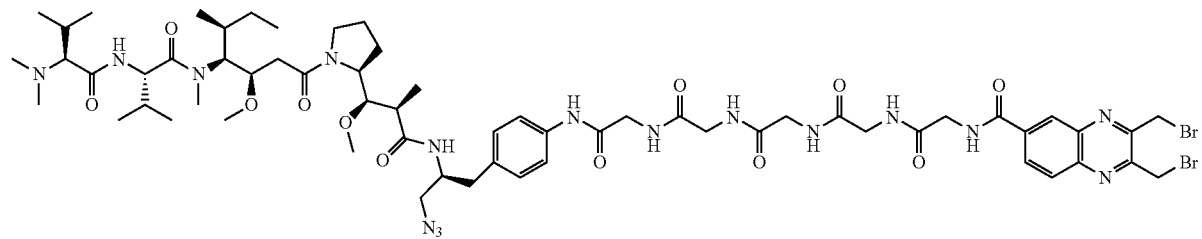
52
Examples of Anti-CD 38 ADCs
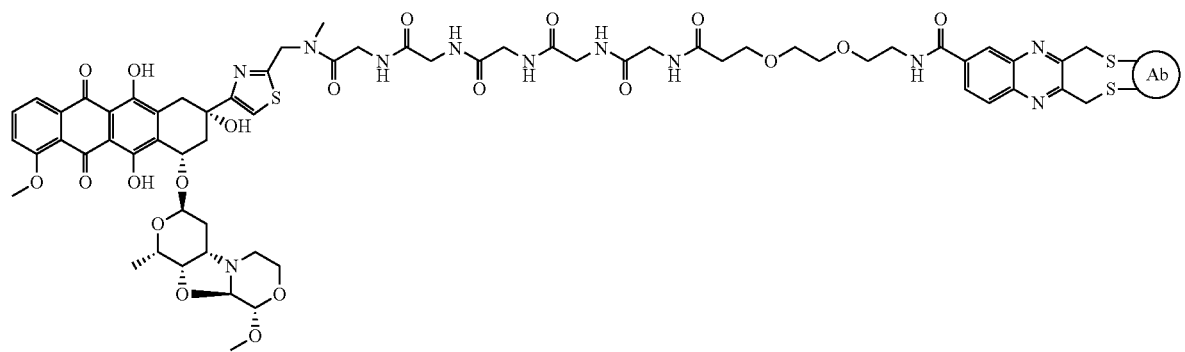
40

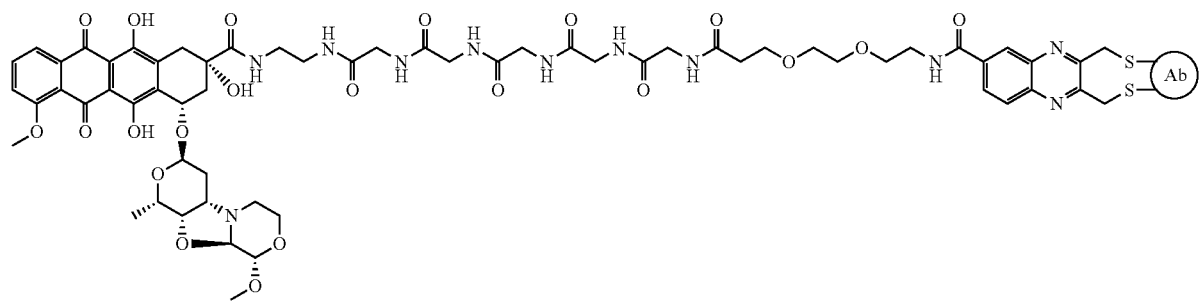
41
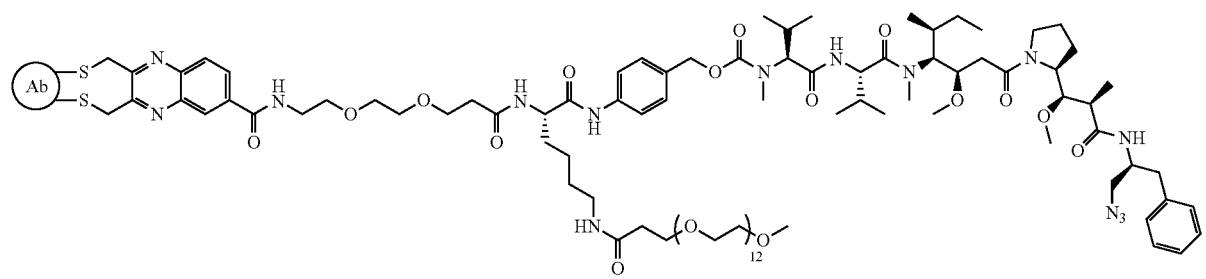
42
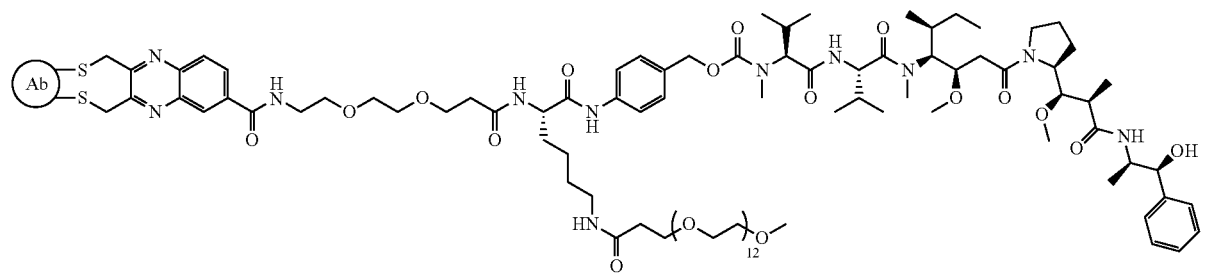
43
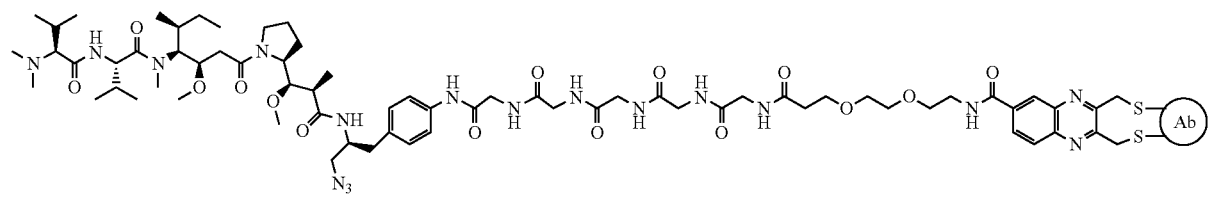
44
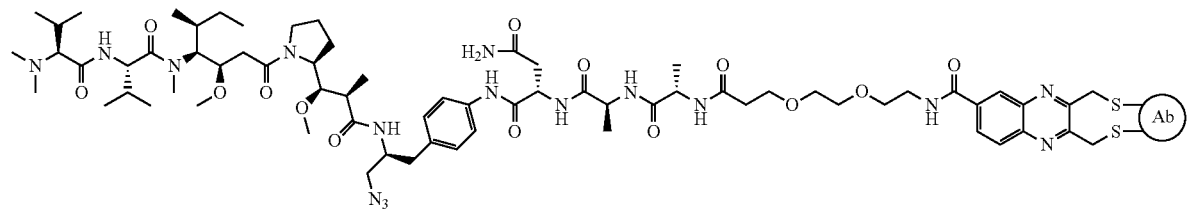
45

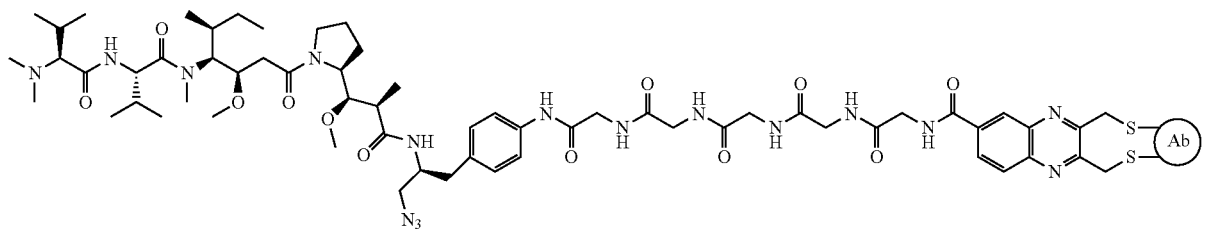

46

Definitions

As used herein, common organic abbreviations are defined as follows:
Ac Acetyl
ACN Acetonitrile
Ala Alanine
Asn Asparagine
aq. Aqueous
BOC or Boc tert-Butoxycarbonyl
° C. Temperature in degrees Centigrade
Cit Citrulline
DCM dichloromethane
DIEA Diisopropylethylamine
DMF N,N'-Dimethylformamide
EDC 1-Ethyl-3-(3-dimethylaminopropyl)carbodiimide
Et Ethyl
EtOAc Ethyl acetate
Eq Equivalents
Fmoc 9-Fluorenylmethoxycarbonyl
g Gram(s)
h Hour (hours)
HATU 2-(1H-7-azabenzotriazol-1-yl)-1,1,3,3-tetramethyl uronium hexafluorophosphate
HOBt N-Hydroxybenzotriazole
HPLC High-performance liquid chromatography
LC/MS Liquid chromatography-mass spectrometry
Me Methyl
mg milligrams
MeOH Methanol
mL Milliliter(s)
µL/µL Microliter(s)
mol moles
mmol millimoles
µmol/umol micromoles
MS mass spectrometry
NHS N-Hydroxysuccinimide
PAB p-aminobenzyl
Pip piperidine
RP-HPLC reverse phase HPLC
rt room temperature
t-Bu tert-Butyl
Tert, t tertiary
TFA Trifluoroacetic acid
THF Tetrahydrofuran
Val Valine Examples of Drug Linker Conjugates:

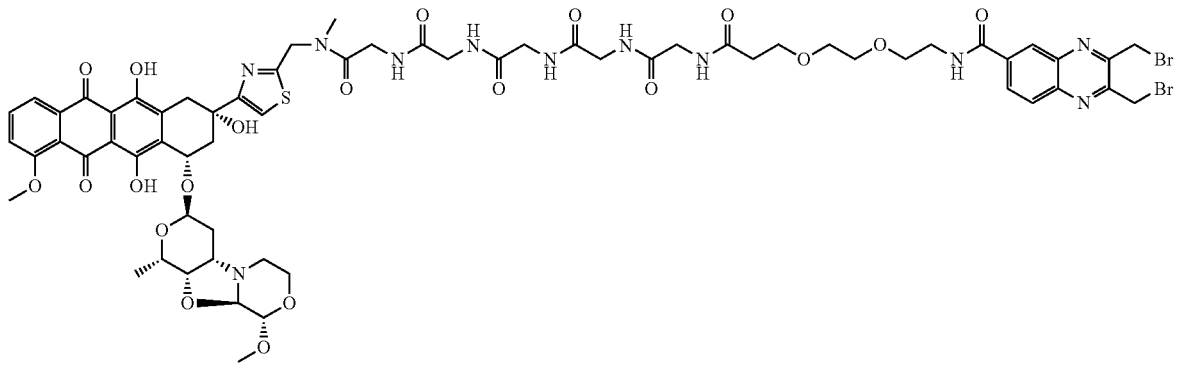

18

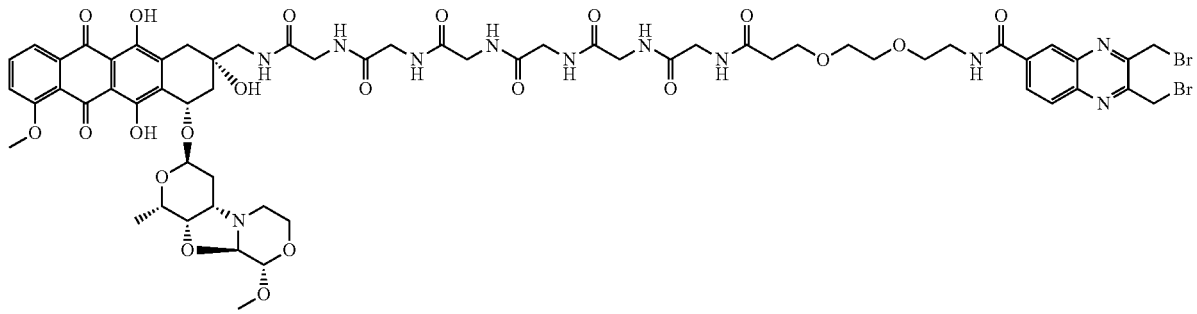

22

27
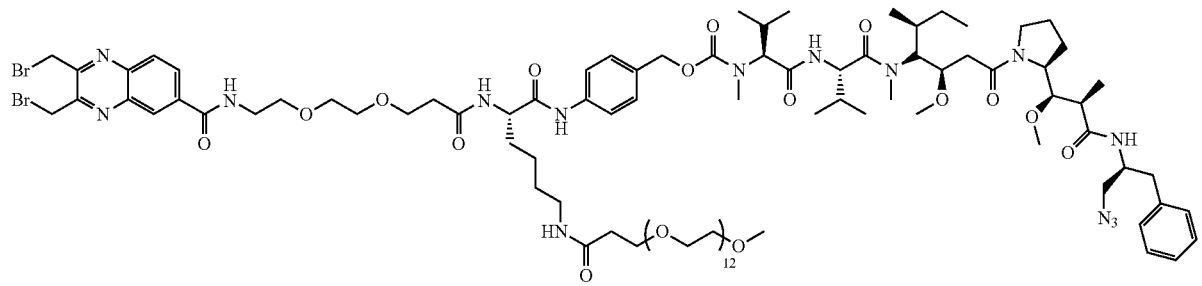
31
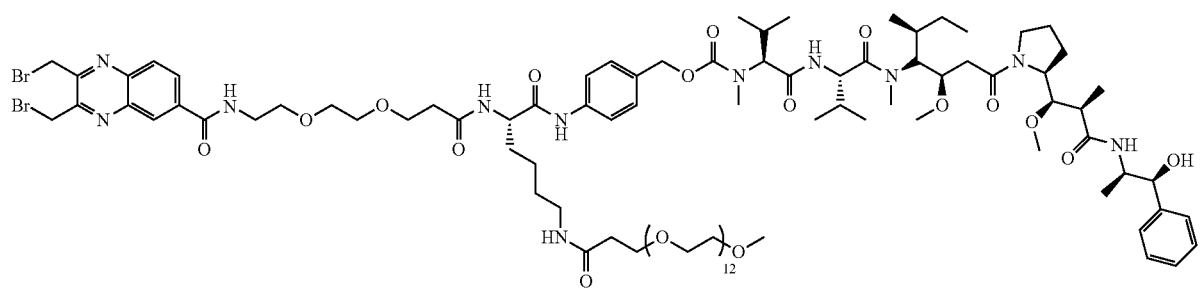
34
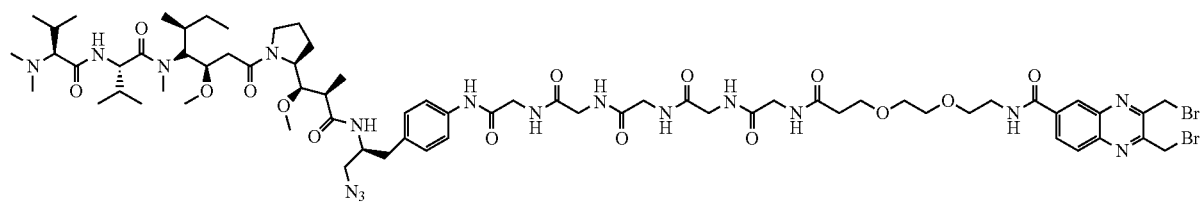
39
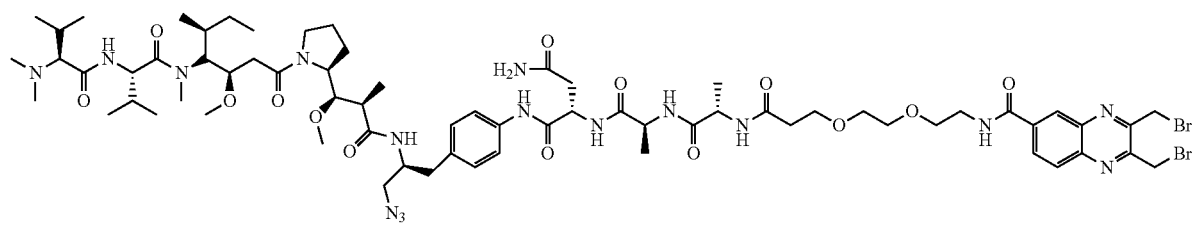
52
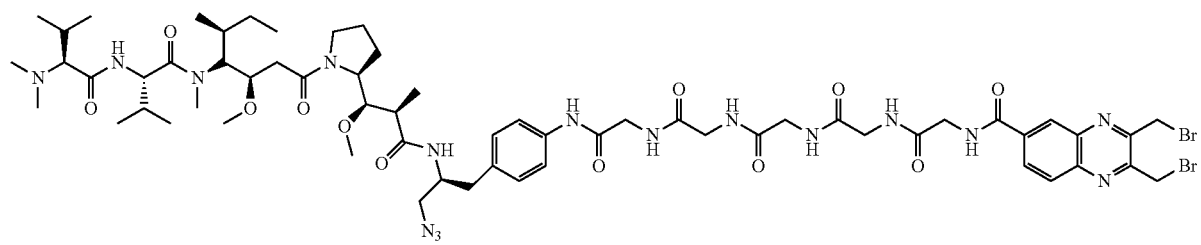

Examples of Anti-CD38 ADCs (the antibody component is called "Ab"):
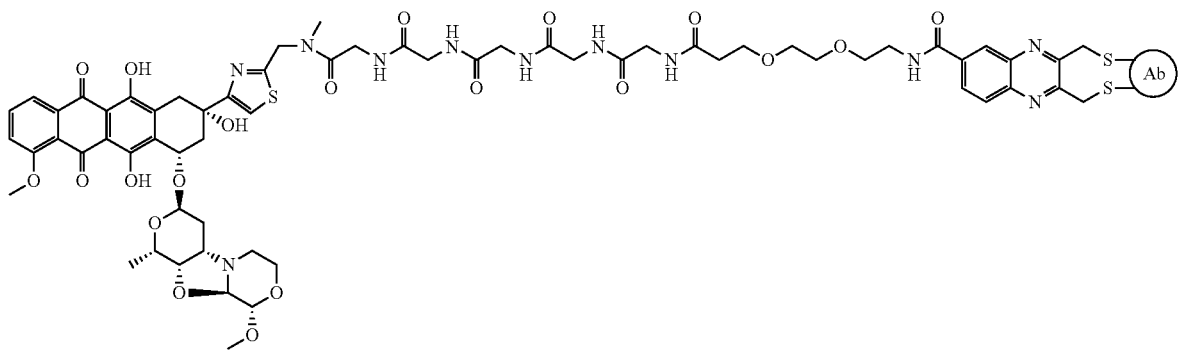
40
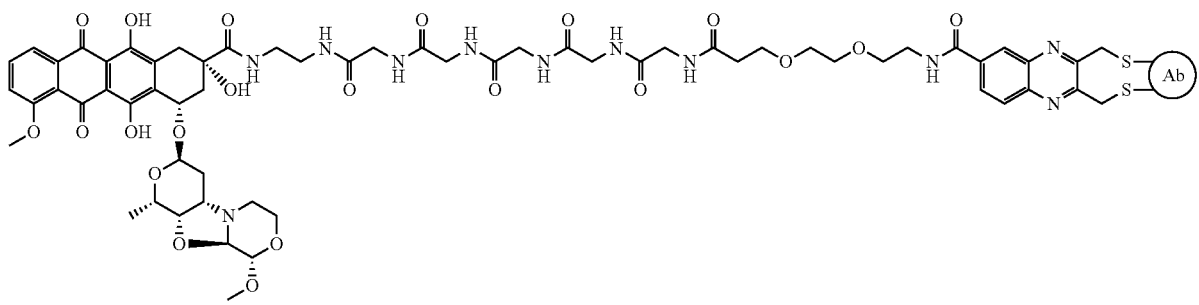
41
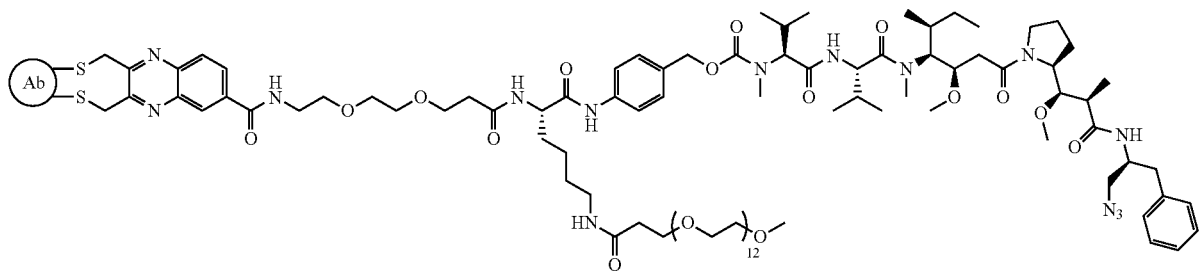
42
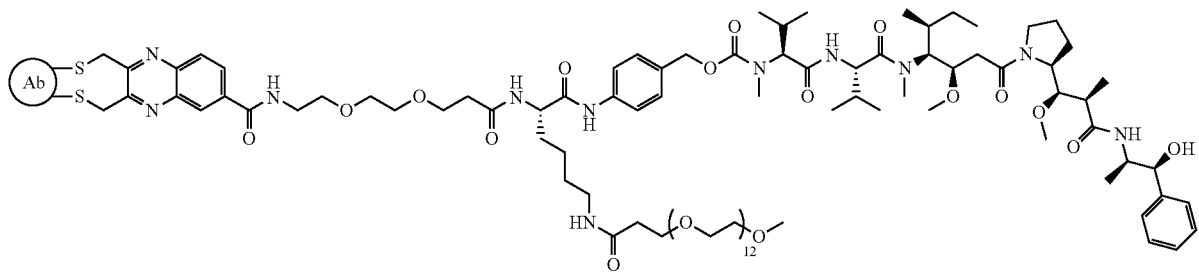
43
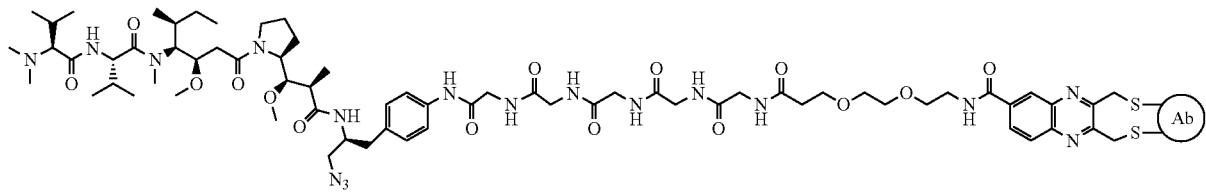
44

-continued
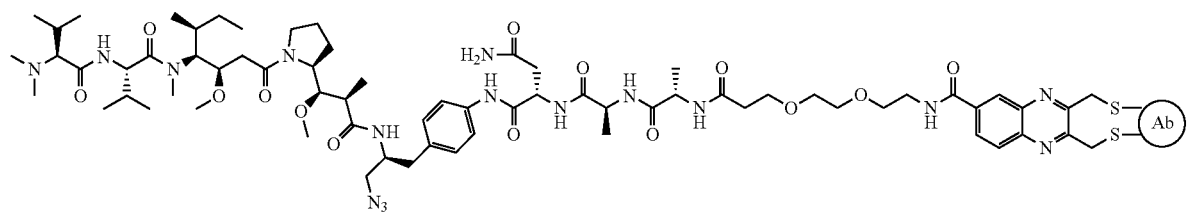
45
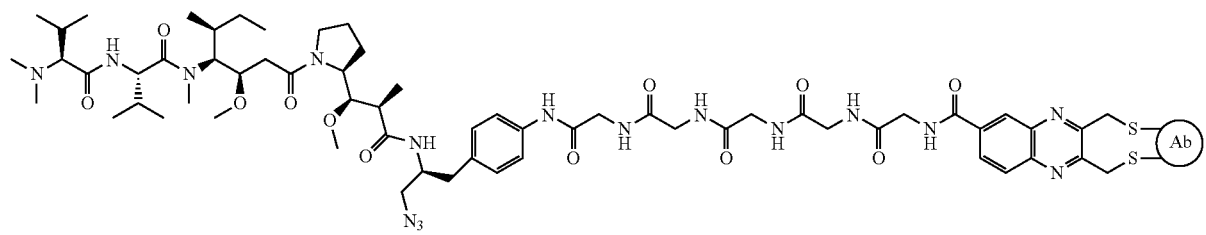
46
SYNTHESIS EXAMPLES 1
Synthesis of Compound 18:
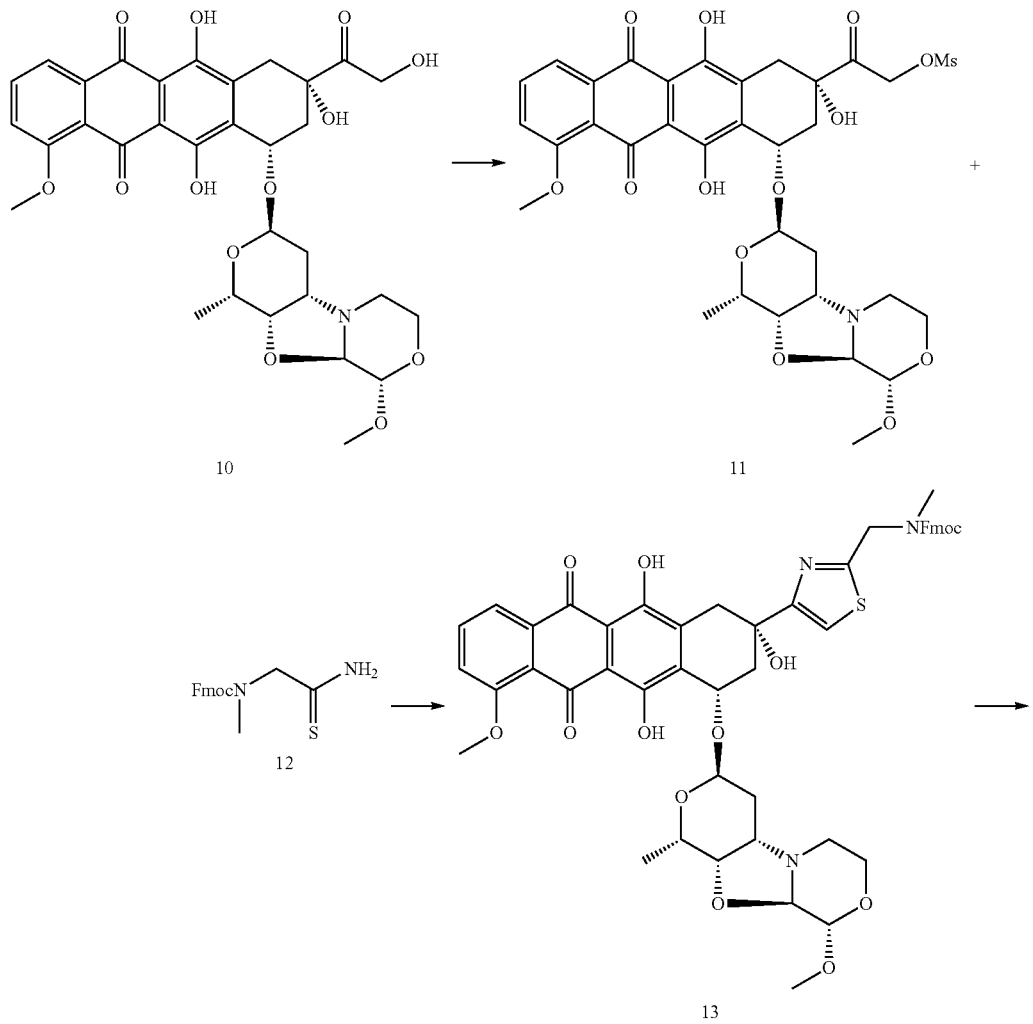

-continued
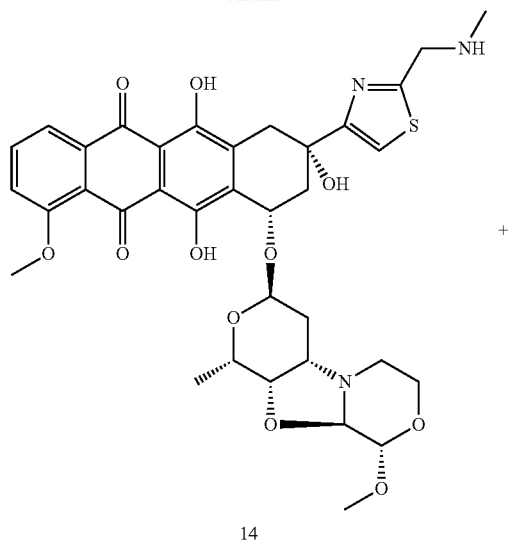
14
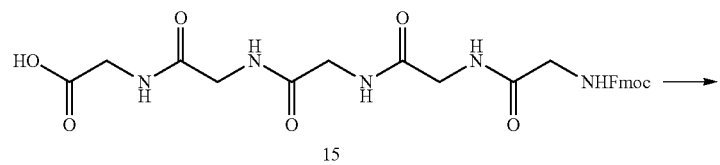
15
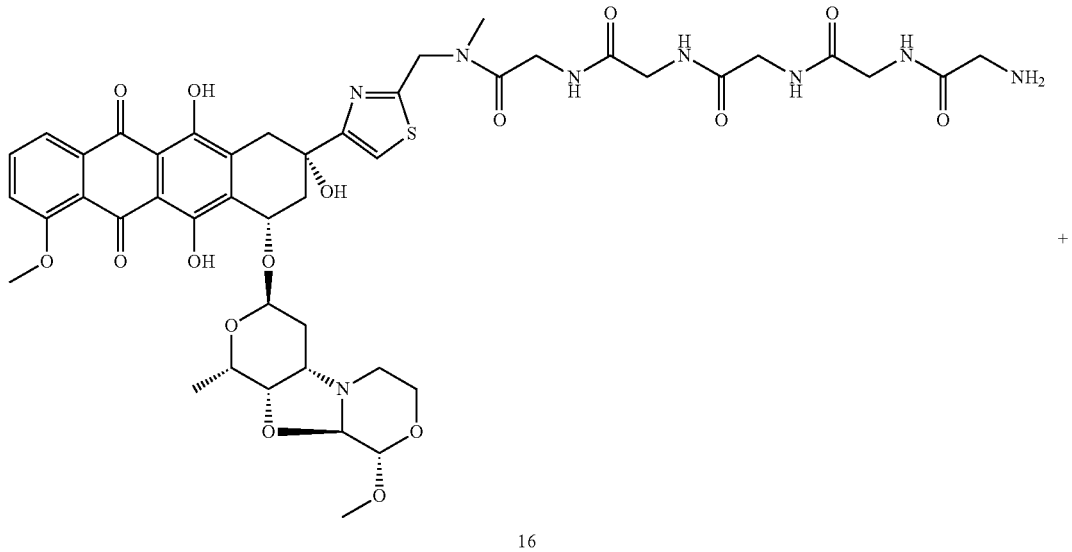
16
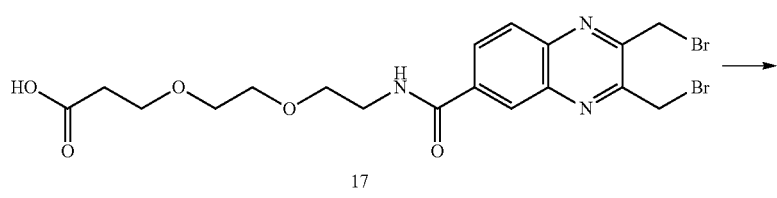
17

-continued

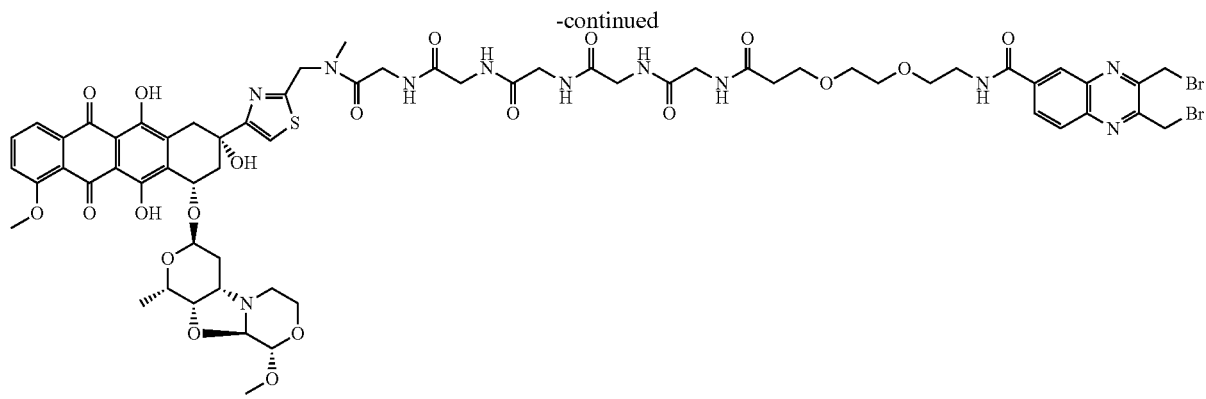

18

Synthesis of Compound 11:

Compound 10 (30 mg, 46.8 µmol) was dissolved in 3 mL of anhydrous DCM under nitrogen. Then DIEA (24 µL, 140 µmol) was added and the reaction mixture was cooled with ice bath. Then methane sulfonyl chloride (7.2 µL, 93.6 µmol) was added and the mixture was stirred for 30 min. The reaction was diluted with 3 mL of DCM and washed with 4 mL of water, dried over anhydrous $Na_2SO_4$ and evaporated to give compound 11 as a red solid (33 mg, 98%). MS m/z=720.5 (M+H)

Synthesis of Compound 13:

Compound 11 (20 mg, 27.8 µmol) was dissolved in 3 mL of anhydrous ethanol under nitrogen. Then thioamide 12 (45 mg, 139 µmol) was added and the mixture was heated at 40° C. for 24 h. The mixture was purified by HPLC to give compound 13 as a red solid (15 mg, 59%). MS m/z=932.6 (M+H)

Synthesis of Compound 14:

Compound 13 (15 mg, 16.1 µmol) was dissolved in 2 mL of anhydrous DMF under nitrogen. Then 60 µL of piperidine was added and the mixture was stirred at ambient temperature for 10 min. The mixture was purified by HPLC to give compound 14 as a red solid (6.9 mg, 60%). MS m/z=710.4 (M+H)

Synthesis of Compound 16:

Compound 15 (8.9 mg, 16.9 µmol) was dissolved in 2 mL of DMF, then HATU (6.4 mg, 16.8 µmol) and DIEA (9 µL, 51.8 µmol) was added. After 2 min, compound 14 (10 mg, 14.1 µmol) was added and the mixture was stirred at ambient temperature for 1 h. To the mixture was added 40 µL of DBU and stirred for 10 min. Then the mixture was purified by HPLC to give compound 16 as a red solid (12.2 mg, 87%). MS m/z=995.4 (M+H)

Synthesis of Compound 18:

Compound 17 (12.5 mg, 24.2 µmol) was dissolved in 2 mL of DCM, then DIC (1.6 mg, 12.7 µmol) was added. After 10 min, compound 16 (12 mg, 12.1 µmol) dissolved in 0.5 mL of DMF was added and the mixture was stirred at ambient temperature for 10 min. Then the mixture was purified by HPLC to give compound 18 as a red solid (12.8 mg, 71%). MS m/z=1494.4 (M+H)

Synthesis of Compound 22:

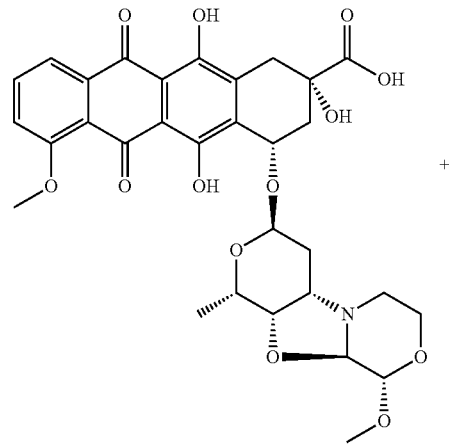

19

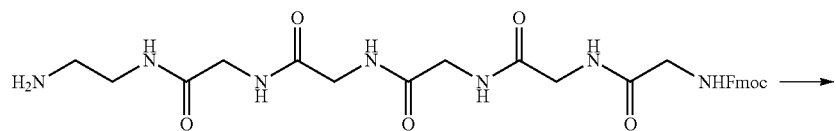

20

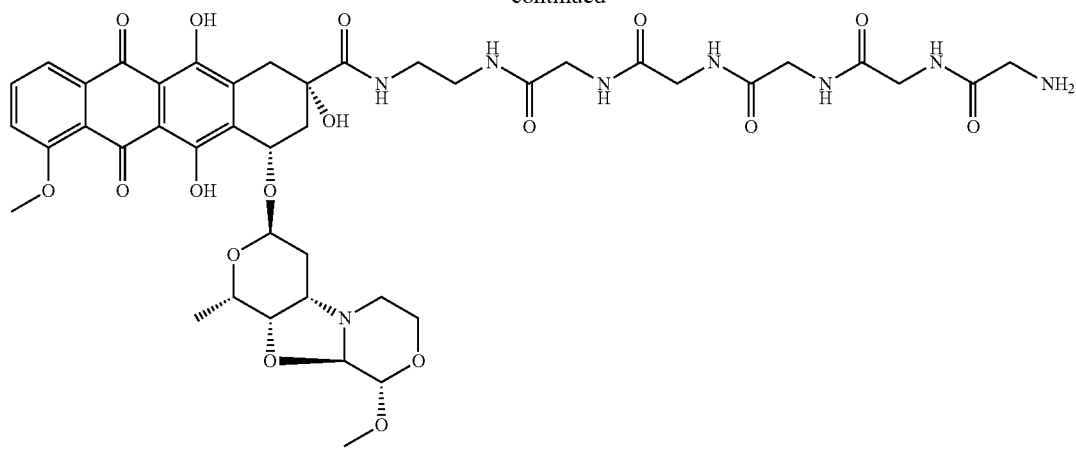
21
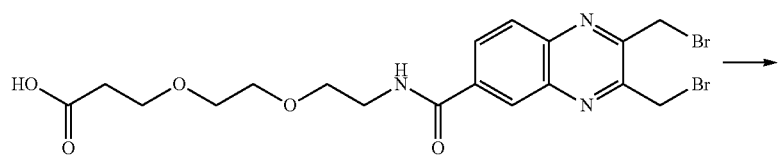
17
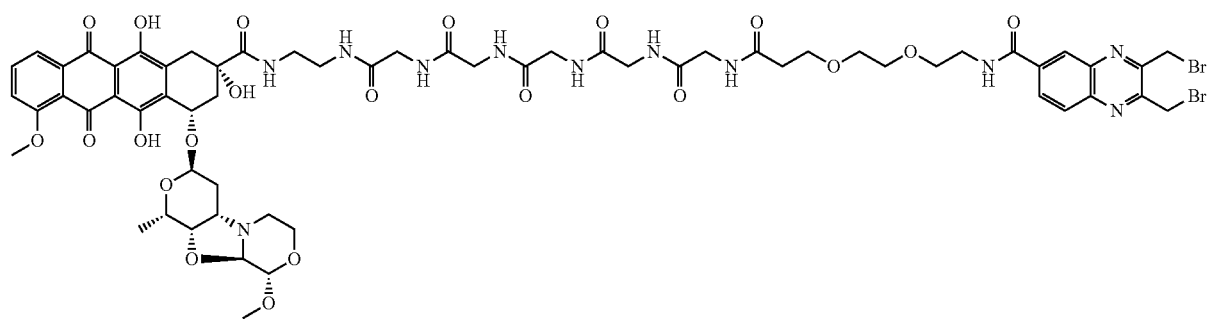
22

Synthesis of Compound 21:

To a solution of acid 19 (51 mg, 81 μmol) in 6 mL of DCM, add N-hydroxysuccinimide (46 mg, 400 μmol), and EDC (100 mg, 523 μmol). After 30 min, the mixture was washed with water (2×6 mL), dried over $Na_2SO_4$ and evaporated. The residue was dissolved in 2 mL of DMF. Then amine 20 (55 mg, 81 μmol, as TFA salt) was added, followed by DIEA (50 μL). The mixture was stirred for 1 h. Then piperidine (40 μL) was added and stirred for 20 min. The mixture was purified by HPLC to give compound 21 (34 mg, 44%) as a red solid; MS m/z 955.2 (M+H).

Synthesis of Compound 22:

Compound 17 (12.5 mg, 24.2 μmol) was dissolved in 2 mL of DCM, then DIC (1.6 mg, 12.7 μmol) was added. After 10 min, compound 21 (11.5 mg, 12.1 μmol) dissolved in 0.5 mL of DMF was added and the mixture was stirred at ambient temperature for 10 min. Then the mixture was purified by HPLC to give compound 22 as a red solid (7.0 mg, 42%). MS m/z=1453.6 (M+H)

Synthesis of Compound 27:

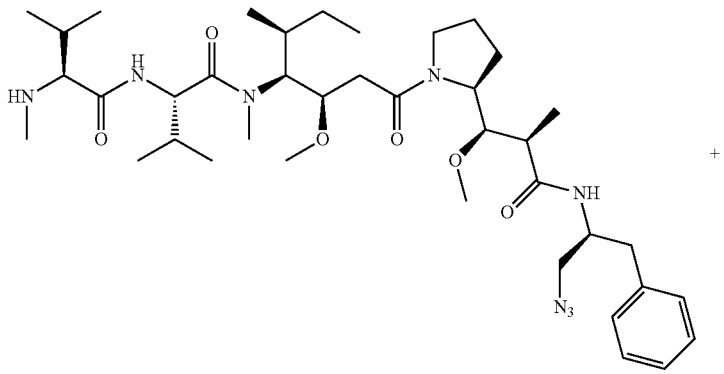

23

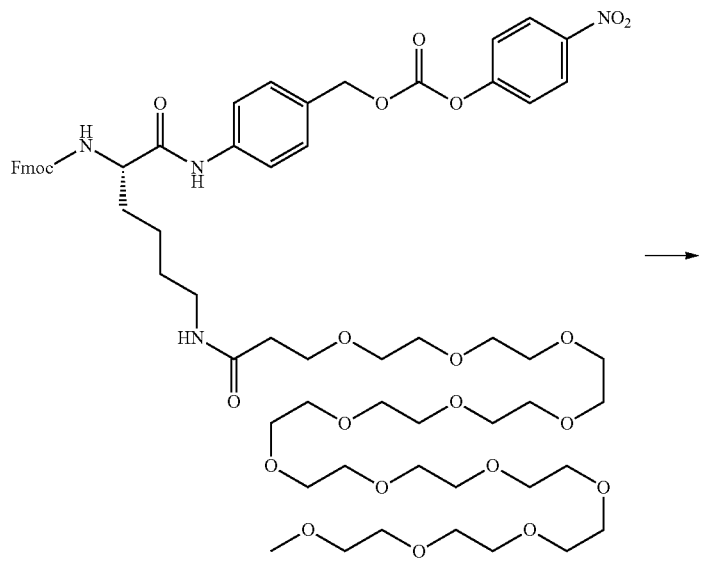

24

63
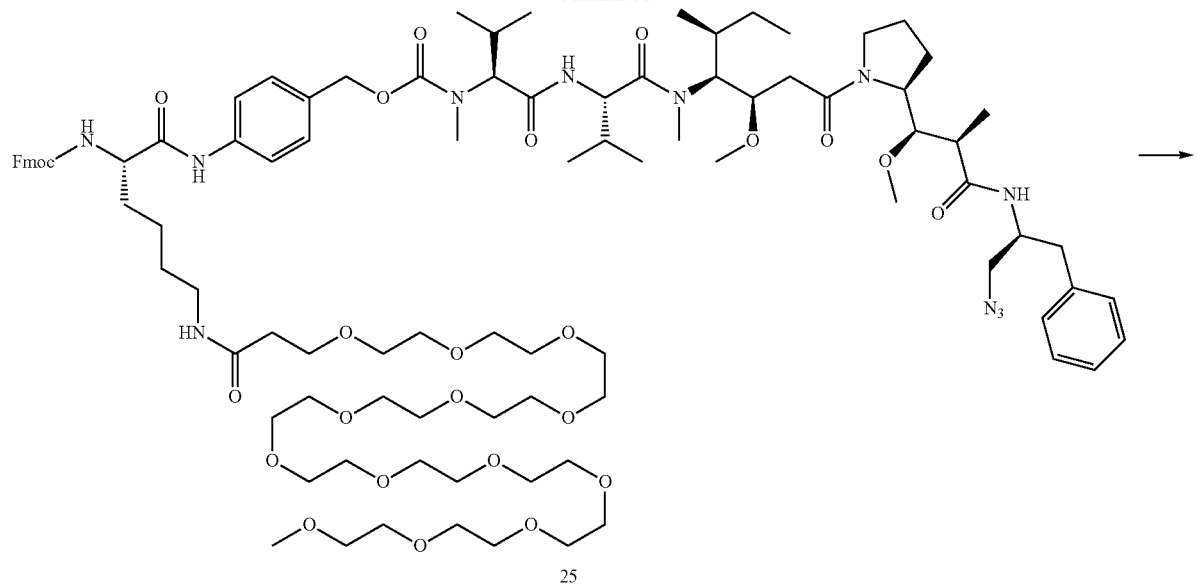
25
64
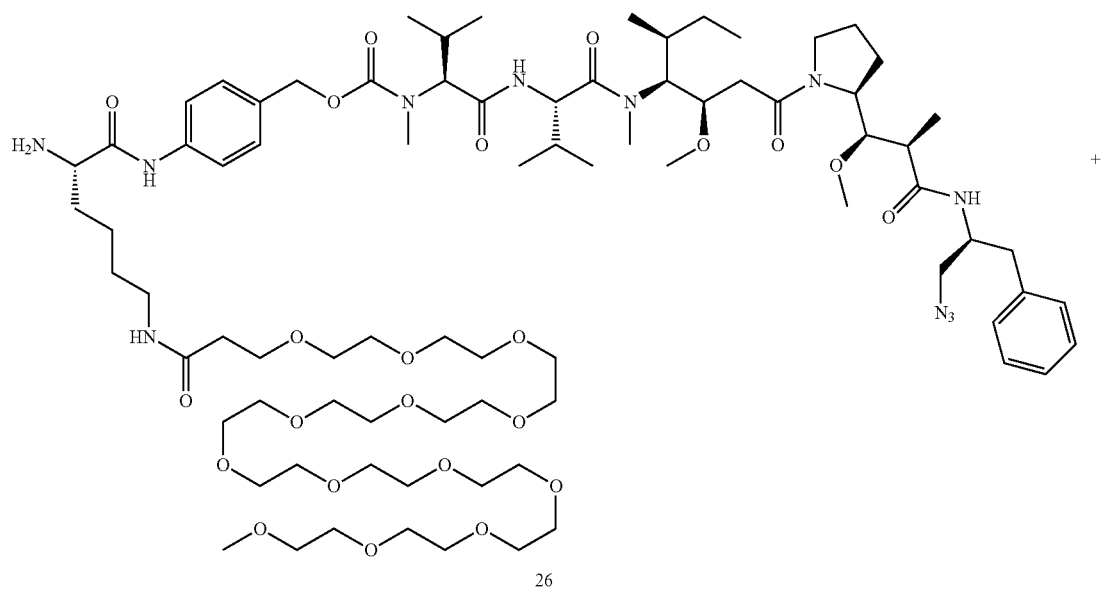
26

-continued

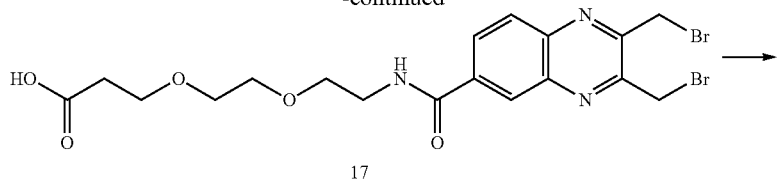

17

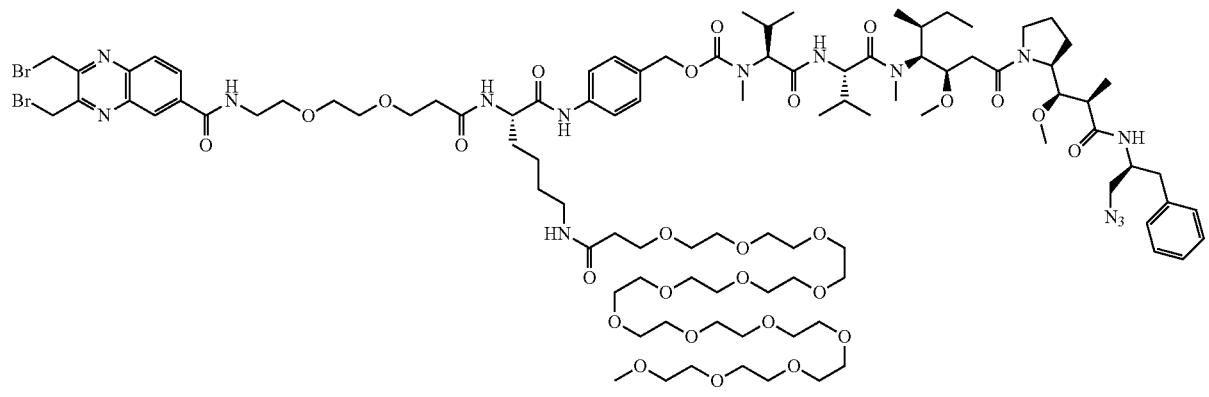

27

Synthesis of Compound 26:

To a solution of compound 23 as TFA salt (84.2 mg, 96.3 μmop in 2 mL of DMF was added compound 24 (120.6 mg, 96.2 μmol), DIEA (50 μμL), HOBt (13 mg, 96.3 μmol). After 24 h, the reaction was completed and then piperidine (60 μL) was added and stirred for 10 min. The mixture was purified by HPLC to give compound 26 (134 mg, 80%) as a white solid; MS m/z 1635.3 (M+H).

Synthesis of Compound 27:

Compound 17 (25 mg, 48.4 μmol) was dissolved in 2 mL of DCM, then DIC (3.2 mg, 25.4 μmol) was added. After 10 min, compound 26 (39.5 mg, 24.2 μmol) dissolved in 0.5 mL of DMF was added and the mixture was stirred at ambient temperature for 10 min. Then the mixture was purified by HPLC to give compound 27 as a white solid (32.0 mg, 62%). MS m/z=2134.1 (M+H)

Synthesis of Compound 31:

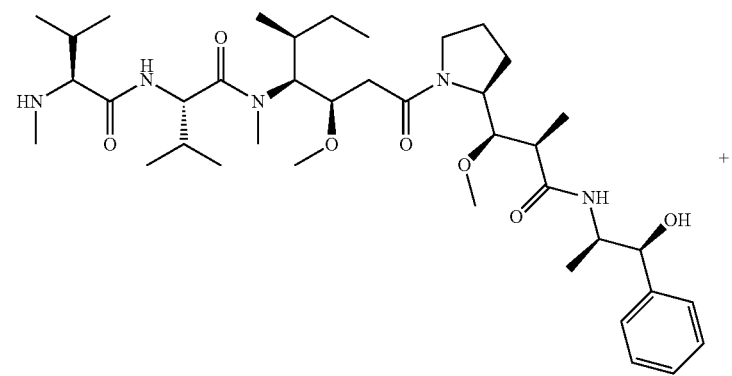

28

-continued
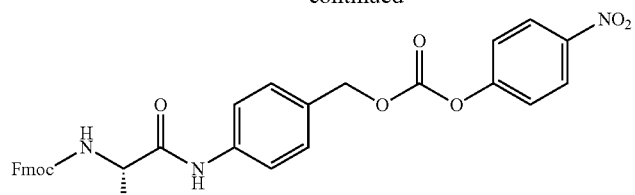
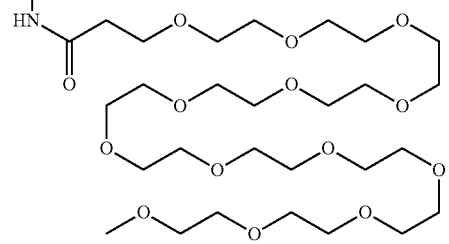
24
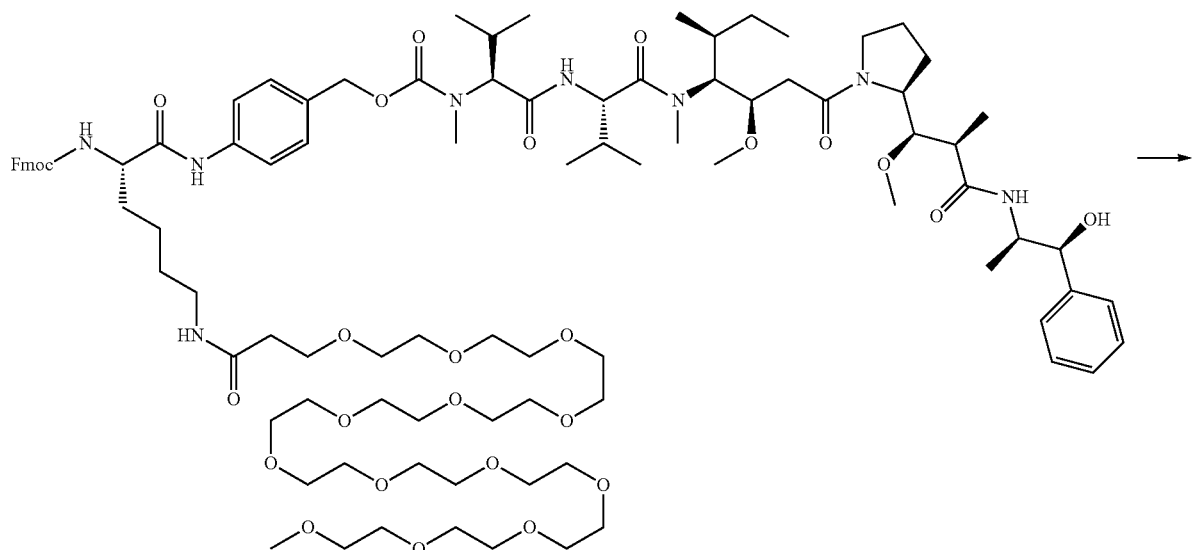
29

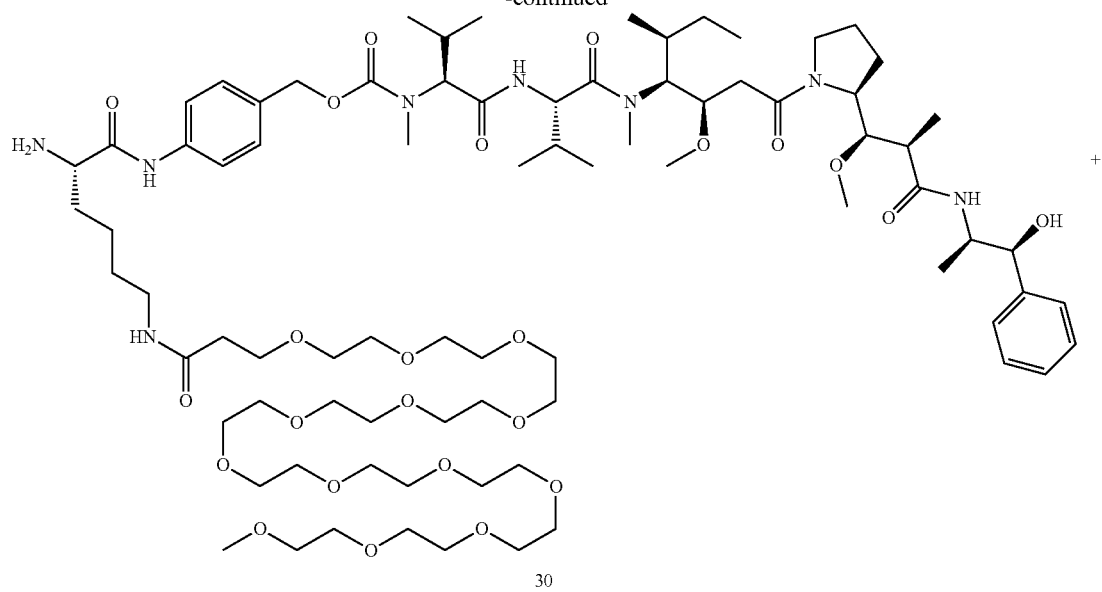
30
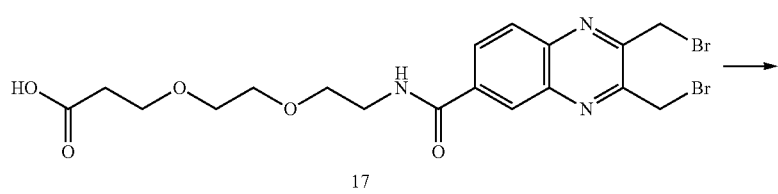
17
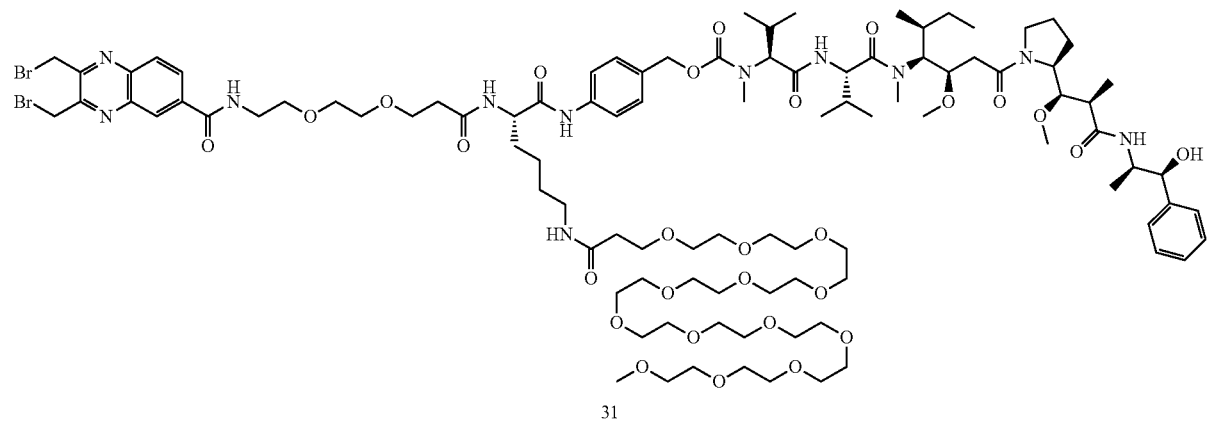
31

Synthesis of Compound 30:

To a solution of compound 28 as TFA salt (30 mg, 36 μmol) in 1 mL of DMF was added compound 24 (45 mg, 36 μmol), DIEA (20 μL), HOBt (5 mg, 37 μmol). After 24 h, the reaction was completed and then piperidine (20 μL) was added and stirred for 30 min. The mixture was purified by HPLC to give compound 30 (46 mg, 79%) as a white solid; MS m/z 1635.3 (M+H).

Synthesis of Compound 31:

Compound 17 (30 mg, 57.1 μmol) was dissolved in 2 mL of DCM, then DIC (3.6 mg, 28.6 μmol) was added. After 10 min, compound 30 (46 mg, 28.6 μmol) dissolved in 0.5 mL of DMF was added and the mixture was stirred at ambient temperature for 10 min. Then the mixture was purified by HPLC to give compound 31 as a white solid (44.8 mg, 59%). MS m/z=2109.2 (M+H).

Synthesis of Compound 34:

Synthesis of Compound 33:

Compound 15 (17 mg, 33 μmol) was dissolved in 2 mL of DMF, then HATU (12.5 mg, 32.9 μmol) and DIEA (23 μL) was added. After 2 min, compound 32 as TFA salt (24 mg, 27.6 μmol) was added and the mixture was stirred at ambient temperature for 1 h. To the mixture was added 40 μL of DBU and stirred for 10 min. Then the mixture was purified by HPLC to give compound 33 as a white solid (30.2 mg, 85%). MS m/z=1057.8 (M+H)

Synthesis of Compound 34:

Compound 17 (12.5 mg, 24.2 μmol) was dissolved in 2 mL of DCM, then DIC (1.6 mg, 12.7 μmol) was added. After 10 min, compound 33 (12.8 mg, 12.1 μmol) dissolved in 0.5 mL of DMF was added and the mixture was stirred at ambient temperature for 10 min. Then the mixture was purified by HPLC to give compound 34 as a white solid (14.5 mg, 77%). MS m/z=1556.8 (M+H).

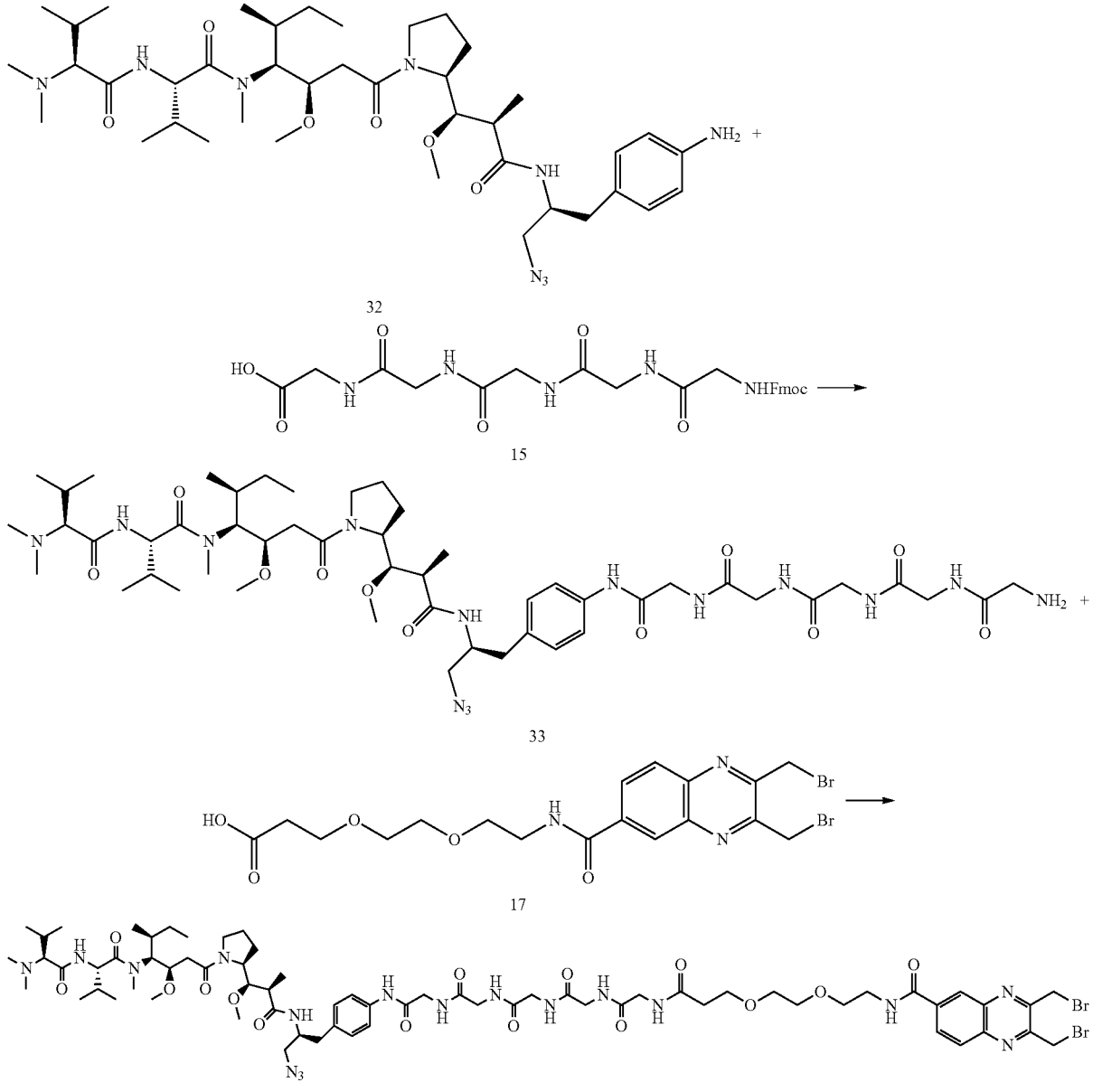

Synthesis of Compound 39:
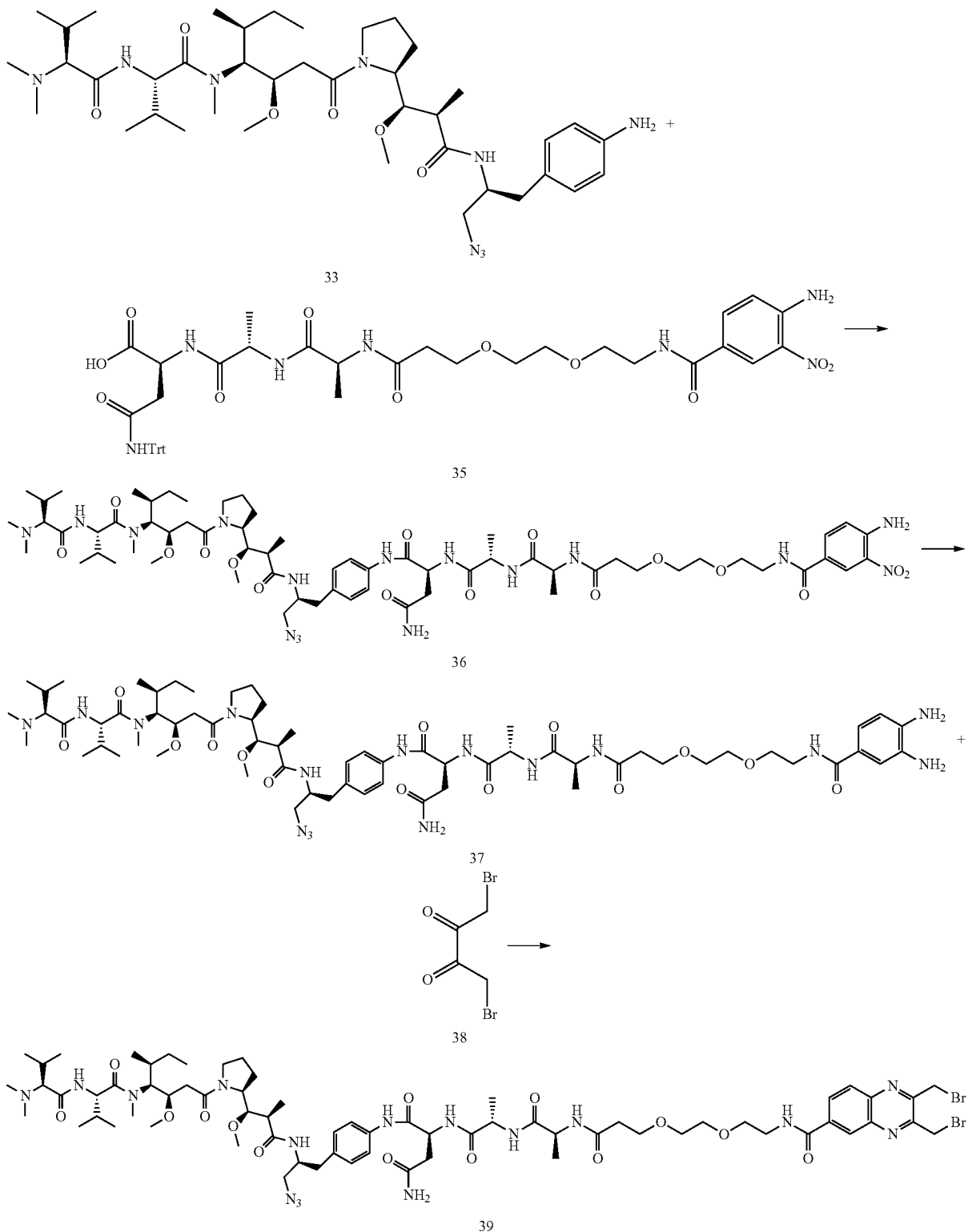
Synthesis of Compound 36:
To a round bottom flask add compound 33 as TFA salt (88.6 mg, 0.1 mmol), compound 35 (84 mg, 0.1 mmol), HOAt (41 mg, 0.3 mmol), DCM (5 mL), DIEA (104 μL), and DIC (25 mg, 0.2 mmol). After 16 h of stirring dilute the reaction mixture with 5 mL of DCM, then wash it with 5 mL of water, dry over $Na_2SO_4$, evaporate solvent under vacuum to give crude glassy solid which was used in the next step.

Dissolve the obtained solid in mixture consisting of 2 mL of DCM, 2 mL of TFA and 0.2 mL of triisopropylsilane and stir for 1 h. Evaporate the solvent under vacuum and purify by HPLC to give compound 36 (81 mg, 60%), MS m/z 1351.5 (M+H).

Synthesis of Compound 37:

To a round bottom flask add compound 36 (81 mg, 0.06 mmol), 2 mL of ACN, 1 mL of water and 1 mL of sat. NaHCO₃ aq. Then add Na₂S₂O₄ (42 mg, 0.24 mmol) and continue stirring for 20 min. Purify the mixture by HPLC to give compound 37 (55 mg, 70%), MS m/z 1321.7 (M+H).

Synthesis of Compound 39:

Compound 37 (53 mg, 0.04 mmol) was dissolved in 2 mL of ACN and 1,4-dibromo-2,3-butanedione (38) (29 mg, 0.12 mmol) was added. After stirring for 20 min, the reaction was purified by HPLC to give compound 39 (40 mg, 65%), MS m/z 1527.6 (M+H).

Synthesis of Compound 52:

then 1 mL of piperidine was added and stirred for 20 min. The mixture was purified by HPLC to give compound 51 TFA salt (1020 mg, 69%) as a white solid; MS m/z 1191.7 (M+H).

Synthesis of Compound 52:

Compound 51 TFA salt (200 mg, 141 umol) was dissolved in 2 mL of ACN and 1 mL of water. Then a solution of 1,4-dibromo-2,3-butanedione 38 (69 mg, 282 μmop in 1 mL of ACN was added. After stirring for 15 min, the reaction was purified by HPLC to give compound 52 as a white solid (166 mg, 84%). MS m/z=1397.6 (M+H)

ADC PREPARATION EXAMPLE 1

Preparation of ADC46

Affinity purified anti-CD38 antibody was buffer exchanged into 50 mM sodium phosphate buffer, pH 7.0-7.2 with 4 mM EDTA at a concentration of 5-10 mg/mL To a

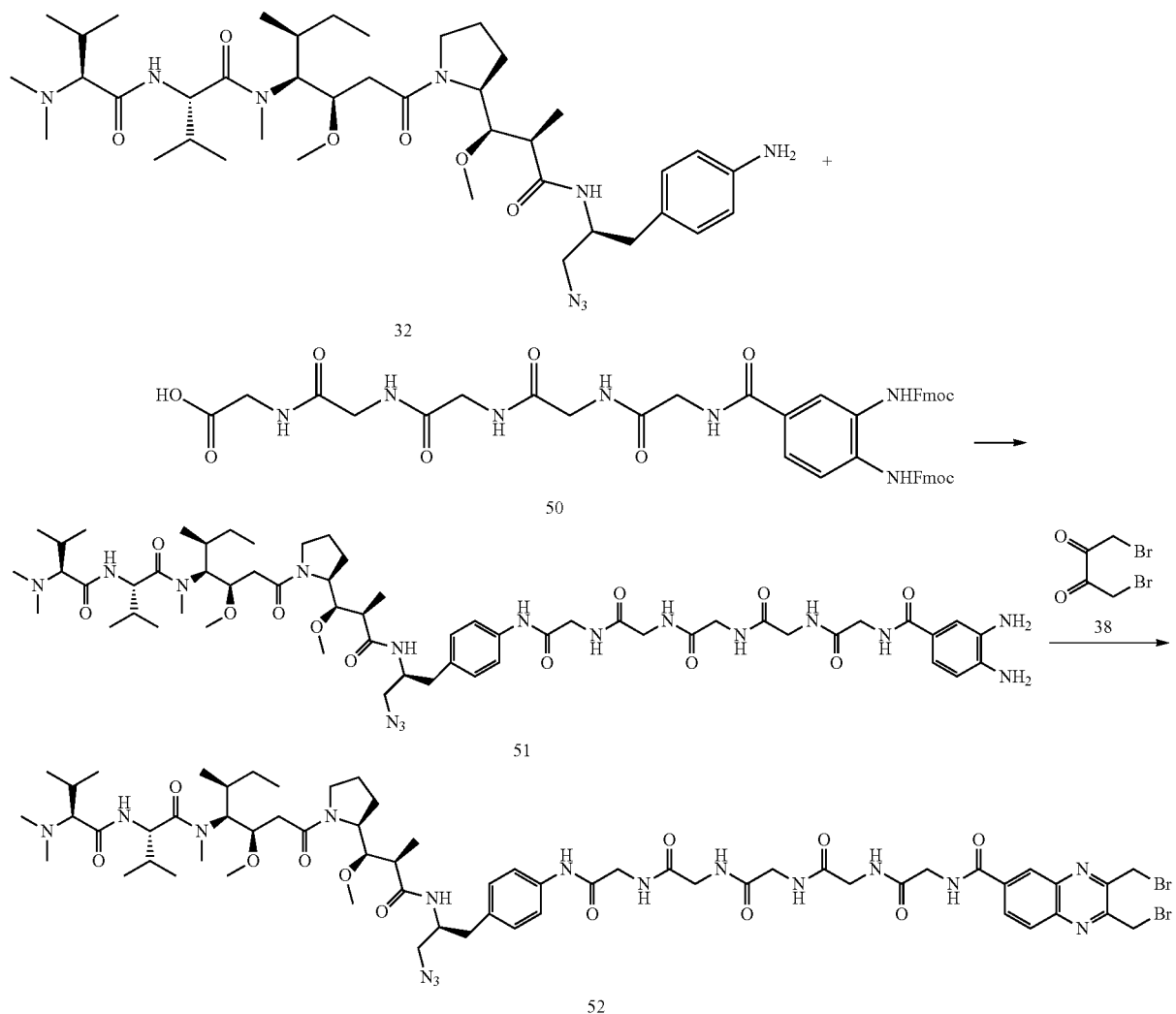

Synthesis of Compound 51:

To a solution of amine 32 (875 mg, 1.13 mmol) and acid 50 (1000 mg, 1.13 mmol) in 10 mL of DMF, was added Oxima-pure (160 mg, 1.13 mmol), followed by DIC (428 mg, 2.74 mmol). After 2 h, the coupling was completed and portion of this antibody stock was added a freshly prepared 10 mM water solution of tris(2-carboxyethyl)phosphine) (TCEP) in up to 20-fold molar excess. The resulting mixture was incubated at 4-8° C. overnight. The excess TCEP was removed by gel-filtration chromatography or several rounds of centrifugal filtration. UV-Vis quantification of recovered, reduced antibody material was followed by confirmation of sufficient free thiol-to-antibody ratio. Briefly, a 1 mM aliquot of freshly prepared (5,5'-dithiobis-(2-nitrobenzoic acid) in 50 mM sodium phosphate, pH 7.0-7.2, 4 mM EDTA was mixed with an equal volume of purified antibody solution. The resulting absorbance at 412 nm was measured and the reduced cysteine content was determined using the extinction coefficient of 14,150 $M^{-1}$ $cm^{-1}$.

Figure 8:
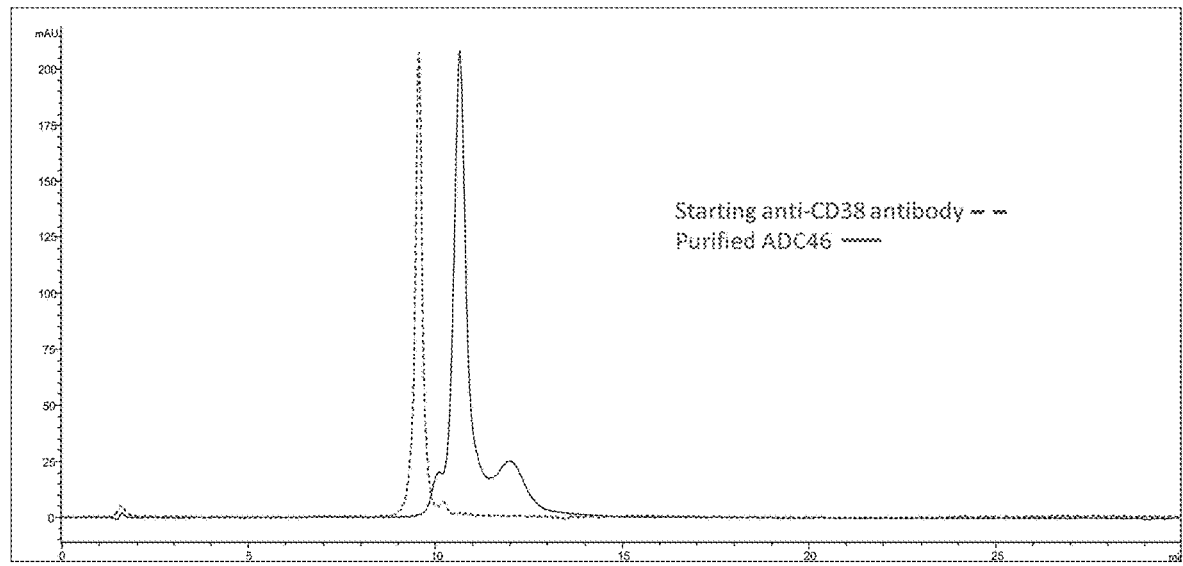
FIG. 8. shows the HIC-HPLC overlay of starting anti-CD38 antibody and purified ADC46 conjugate at 280 nm detection.

To initiate conjugation of compound 52 to anti-CD38 antibody, L014-077 was first dissolved in a 3:2 acetonitrile/water mixture at a concentration of 5 mM. An aliquot of this freshly prepared toxin-linker solution was then added to a portion of the reduced, purified anti-CD38 antibody intermediate in 4.5-5 fold molar excess. After thorough mixing and incubation at ambient temperature for ≥1 h, the crude conjugation reaction was analyzed by HIC-HPLC chromatography to confirm reaction completion (disappearance of starting antibody peak) at 280 nm wavelength detection. Purification of ADC46 was then carried out by gel-filtration chromatography using an AKTA system equipped with a Superdex 200 pg column (GE Healthcare) equilibrated with PBS. The drug-to-antibody ratio (DAR) was calculated based on UV-VIS and HIC-HPLC. FIG. 8 shows a representative HIC-HPLC comparison of starting anti-CD38 antibody and purified ADC46. Confirmation of low percent (<5%) high molecular weight (HMW) aggregates for the resulting ADC46 was determined using analytical SEC-HPLC.

Preparation of ADC41

Figure 9:
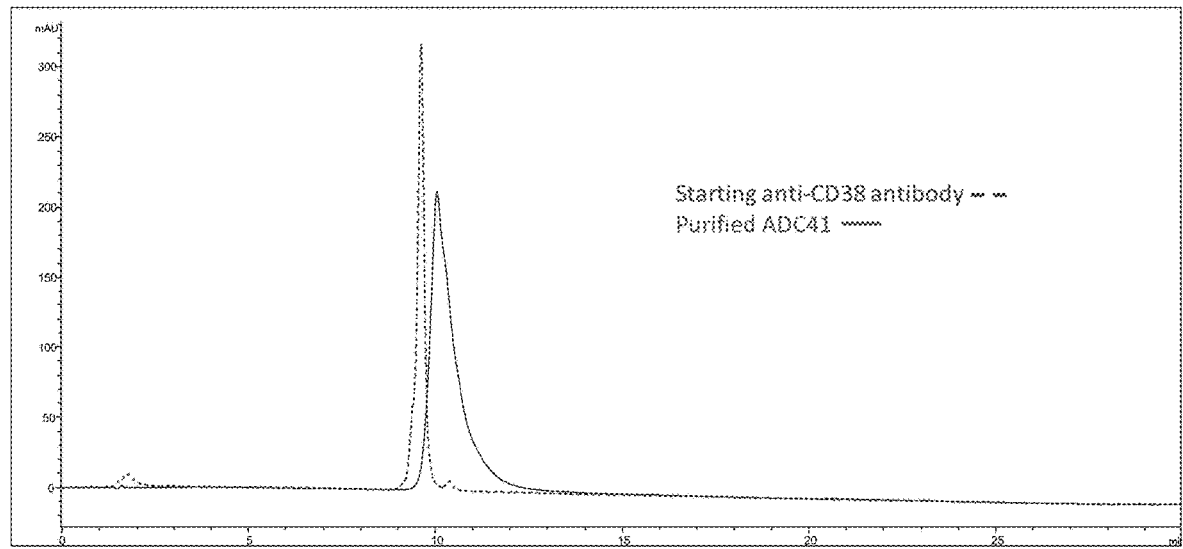
FIG. 9. shows the HIC-HPLC overlay of starting anti-CD38 antibody and purified ADC41 conjugate at 280 nm detection.
Figure 10A:
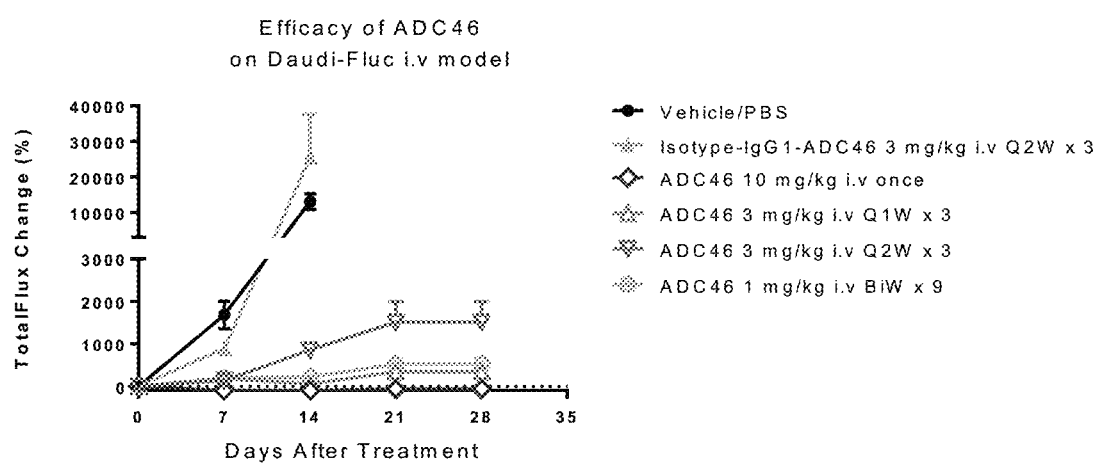
FIG. 10A shows an in vivo study of anti-CD38 ADC46 on Burkitt lymphoma model. In the study, 10 million of Daudi cells were injected s.c. to Nu Nu mice. ADC 46 was iv injected to tumor bearing mice after the average tumor volume reached 200 mm$^3$.
Figure 10B:
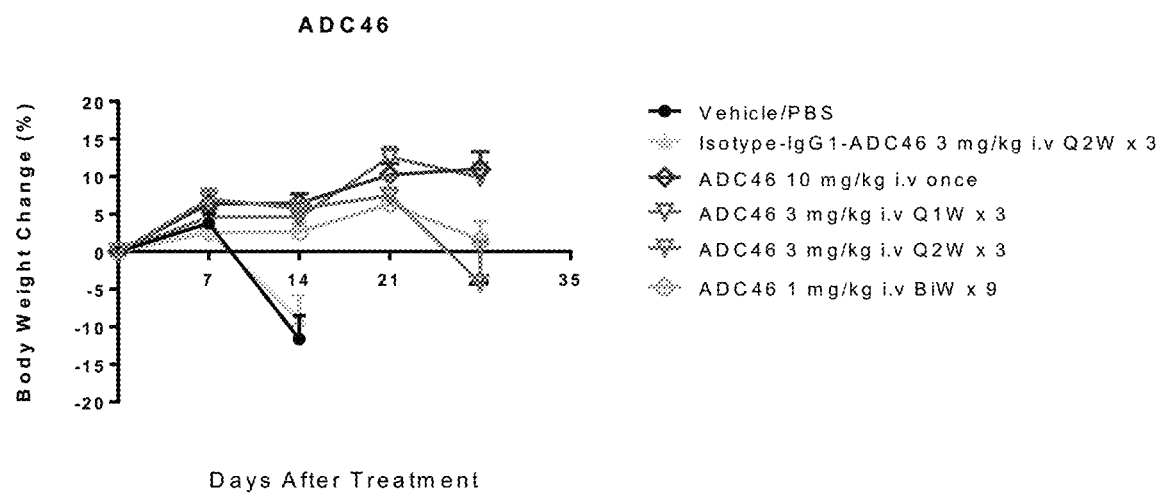
FIG. 10B shows bodyweight measure of mice treated with ADC 46 at three different indicated doses.

Reduction and analysis of anti-CD38 antibody for ADC41 was conducted in a manner identical to the procedure used to generate ADC46. To initiate final drug-linker conjugation to antibody, Compound 22 was first dissolved in a 2:3 acetonitrile/water mixture at a concentration of 5 mM. Propylene glycol (PG) was then added to an aliquot of the reduced, purified anti-CD38 antibody to give a final concentration of 10-30% (v/v) PG before addition of the freshly prepared compound 22 solution in 4.5-5-fold molar excess. Subsequent analysis and purification of ADC41 was carried out in a manner identical to the procedure for ADC46. FIG. 9 shows a representative HIC-HPLC comparison of starting anti-CD38 antibody and purified ADC41.

ASSAY EXAMPLE 1

Upon receipt, animals were housed 5 mice per cage in a room with a controlled environment. Animals were provided rodent chow and water ad libitum. Acclimation of the mice to laboratory conditions was at least 72 hours prior to the start of cell administration and dosing. During the acclimation period, the animals' health status was determined. Only animals that are observed to be healthy prior to study initiation were used.

This example provides an in vivo experiment comparing treatment of mice with control (PBS), anti-CD38 IgG1 antibody (STI-0602 and STI-0607) and an ADC variant of both antibodies. The procedure first does a tumor cell inoculation & establishment of tumors:

a. U87 cells were cultured with 10% FBS U87 medium (EMEM) and harvested with 0.05% trypsin. Cells were washed 2 times with serum-free EMEM, counted, and resuspended at $5\times10^6$ cells in 0.2 mL or, $25\times10^6$ cells/mL in a 1:1 mix of serum-free EMEM and matrigel and injected subcutaneously into the upper right flank of each mouse.

b. Tumor growth was monitored by tumor volume measurement using a digital caliper starting Day 6-9 after inoculation, 2 times per week thereafter and prior to study termination.

c. Tumors were measured with digital calipers. The length (the longest dimension) and the width (the distance perpendicular to and in the same plane as the length) were measured. The formula for calculating tumor volume was TV (mm3)=½×L×W2.

Treatments:

a. Once tumors were staged to the desired volume (average from 200 to 300 mm3), animals were randomized and mice with very large or small tumors culled. Mice were divided into 8 groups of 10 mice each, randomized by tumor volume.

b. Mice were treated with either vehicle or Test Article according to FIG. 4. Mice received a total of 5 doses.

c. Tumor responses were monitored and study terminated once clear treatment trends are established and/or when tumor load in vehicle-treated mice reaches IACUC protocol limits (2000 $mm^3$).

ASSAY EXAMPLE 2

This example is an in vivo experiment comparing two disclosed CD38 ADCs in vivo with mice In the in vivo study, 10 million of Daudi-fluc cells were injected iv into NOD-SCID mice. 4 days after tumor established in mice, anti-CD38 antibody and ADCs were injected to mice by IV. The inhibition of tumor growth by antibody or ADCs was monitored by the luminesce intensity change of the tumor (FIGS. 3, 4, 5 and 6).

ADC #45 and ADC # 41 were tested. Both ADC's use the same A2 antibody. The Daudi and Ramos cell line was obtained from ATCC. The cells were cultured in RPMI 1640 1× medium with 10% FBS and at 37° C. in a 5% carbon dioxide humidified environment. Cells were cultured for a period of 2 weeks and were passaged 3 times before harvest. Prior to injection, Daudi or Ramos cells were resuspended in a 1:1 ratio of HBSS (Hank's balanced salt solution) and Matrigel, and 10 million cells per 0.2 ml were injected subcutaneously into the upper right flank of each mouse.

The Daudi-luc cells were cultured in RPMI 1640 1× medium with 10% FBS and 0.2 ug/ml puromycin at 37° C. in a 5% carbon dioxide humidified environment. Cells cultured for a period of 2 weeks and were passaged 3 times before harvest. Prior to injection, Daudi-luc cells were resuspended in HBSS. 10 million cells per 0.2 ml were injected intravenously in to the tail vein of each mouse.

Female NOD SCID mice aged 6 weeks (Charles River) were used for Daudi subcutaneous xenografts and Daudi-luc intravenous xenografts. Female Nu/Nu mice aged 6 weeks (Charles River) were used for Ramos subcutaneous xenografts in the studies. Upon receipt, mice were housed 5 mice per cage in a room with a controlled environment. Rodent chow and water was provided ad libitum. Mice were acclimated to laboratory conditions for 72 hours before the start of dosing. The animals' health status was monitored during the acclimation period. Each cage was identified by group number and study number, and mice were identified individually by ear tags.

The study design and dosing regimens are shown in the following table.

| Tumor Models | Group | # of Animal | Treatment | Dose/frequency | Volume/route |
|---|---|---|---|---|---|
| Daudi subcutaneous xenograft in NOD SCID mice | 1 | 7 | PBS | 0 mg/kg, single | 0.2 ml/iv |
| | 2 | 7 | ADC#45 | 10 mg/kg, single | 0.2 ml/iv |
| | 3 | 7 | ADC#45 | 3 mg/kg, single | 0.2 ml/iv |
| | 4 | 7 | ADC#45 | 1 mg/kg, single | 0.2 ml/iv |
| Ramos subcutaneous xenograft in Nu/Nu mice | 1 | 7 | PBS | 0 mg/kg single | 0.2 ml/iv |
| | 2 | 7 | ADC#45 | 10 mg/kg, single | 0.2 ml/iv |
| | 3 | 7 | ADC#45 | 3 mg/kg, single | 0.2 ml/iv |
| | 4 | 7 | ADC#45 | 1 mg/kg, single | 0.2 ml/iv |
| Daudi-luc intravenous model in NOD SCID mice | 1 | 8 | PBS | 0 mg/kg, single | 0.2 ml/iv |
| | 2 | 8 | Ab | 3 mg/kg, single | 0.2 ml/iv |
| | 3 | 8 | ADC#45 | 3 mg/kg, single | 0.2 ml/iv |
| | 4 | 8 | ADC#41 | 3 mg/kg, single | 0.2 ml/iv |

Tumor growth was monitored by measurement of tumor width and length using a digital caliper starting day 5-7 after inoculation, and followed twice per week until tumor volume reached ~100-250 mm$^3$. Tumor volume was calculated using the formula: Volume (mm$^3$)=[Length (mm)×Width (mm)$^2$]/2.

Once tumors were staged to the desired volume, animals were randomized, and mice with very large or small tumors were culled. Mice were divided into groups with animal numbers per group as indicated in study design. Mice were then treated intravenously (0.2 ml/animal) with either PBS, Ab, ADC #45, or ADC #41. Tumor growth, animal health and body weight were monitored after treatment. Testing animals were sacrificed when the average subcutaneous tumor load for the group exceeded 2000 mm$^3$, animal body-weight loss exceed 20%, or at the end of the study.

Tumor volume was measured twice weekly throughout the experimental period. TGI (tumor growth inhibition %) was calculated using the formula: TGI=[(Last Volume Measurement of PBS Group−Volume of Treatment group on the same day as the PBS control)/(Last Volume Measurement of PBS Group)]×100. The body weight of each mouse was measured twice weekly by electric balance.

Raw data of individual body weight and tumor volume were calculated. Group average and standard deviation were calculated, and statistical analyses (one-way ANOVA with Dunnett's multiple comparison test; GraphPad Prism 6.0) was carried out. All treatment groups were compared with the PBS group. $P<0.05$ was considered statistically significant.

Figure 1B:
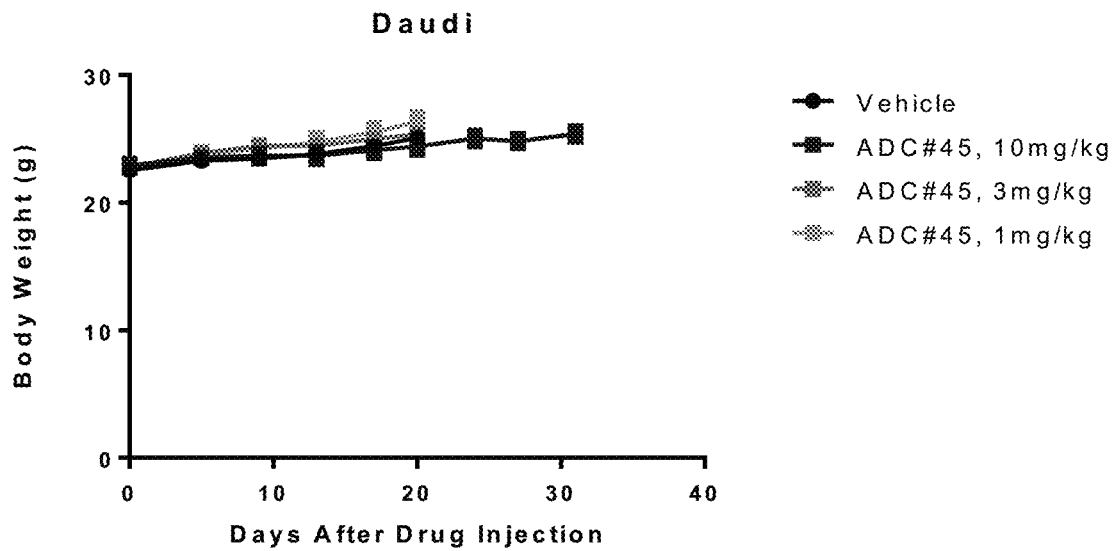
FIG. 1B shows bodyweight measure of mice treated with ADC #45 at three different indicated doses.

ADC #45 at 10 mg/kg significantly inhibited Daudi tumor growth compared to PBS treated control group. Although the tumor regained growth after 3 weeks, the single 10 mg/kg treatment significantly delayed tumor growth. In this case, multiple treatment may be tested to achieve sustained tumor inhibition. While a single dose of ADC #45 at 3 mg/kg or 1 mg/kg did not significantly inhibited tumor growth. However, although the difference was not significant, a single dose of ADC #45 did show slightly inhibition of tumor growth compared to PBS treated control group. Dose response was observed in this study, where higher dose showed better tumor growth inhibition (FIG. 1A). There was no body weight loss in the testing animals with a single dose of intravenously administered ADC #45 at 10 mg/kg or lower dose (FIG. 1B).

Figure 2A:
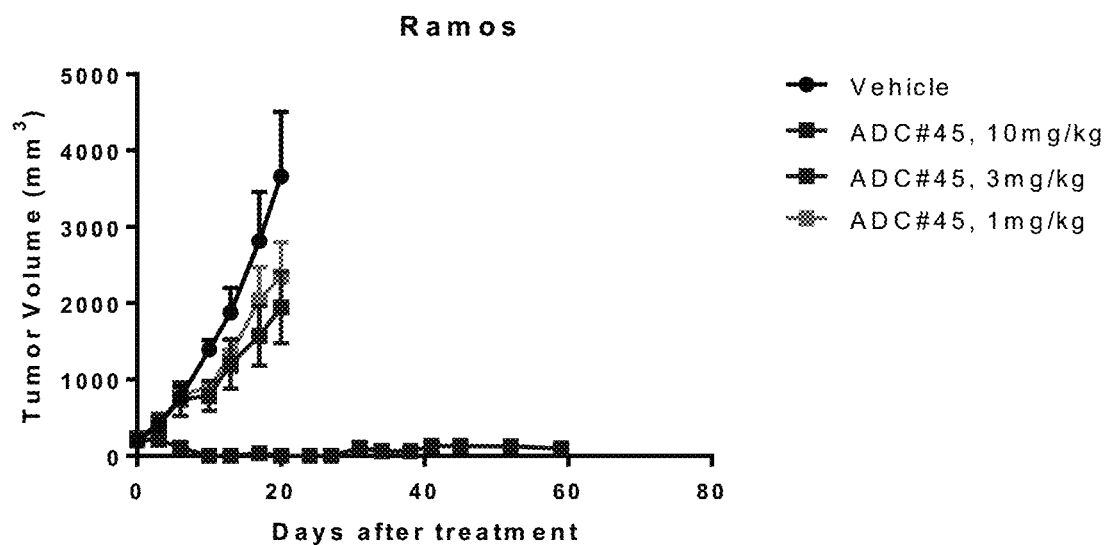
FIG. 2A shows an in vivo study of anti-CD38 ADCs on Burkitt lymphoma model. In the study, 10 million of Ramos cells were s.c injected to Nu Nu mice. ADC #45 was iv injected to tumor bearing mice at the dosages indicated after the average tumor volume reached 200 mm$^3$.
Figure 2B:
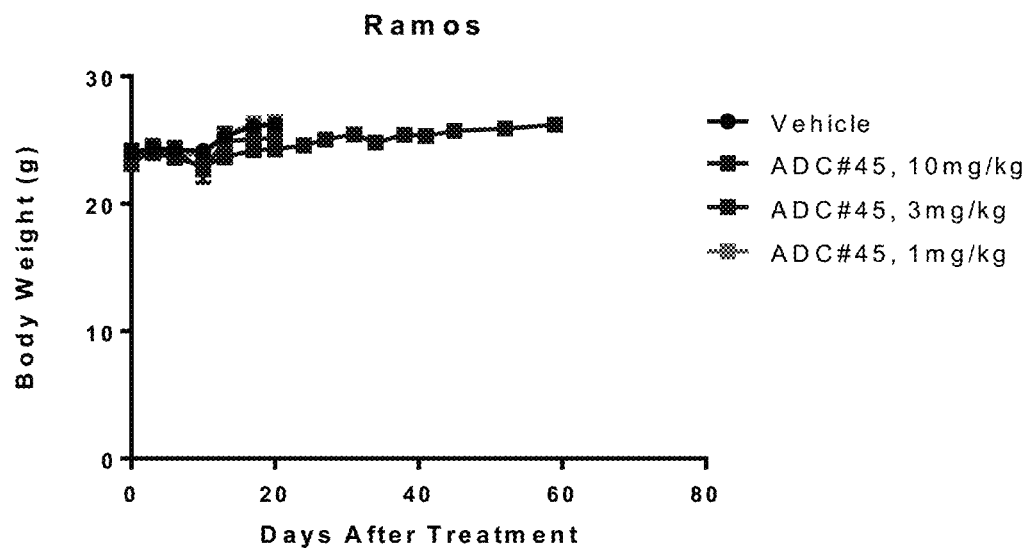
FIG. 2B shows bodyweight measure of mice treated with anti-CD38-ADC.

Similarly, ADC #45 at 10 mg/kg significantly inhibited Ramos tumor growth compared to PBS treated control group and had sustained tumor inhibition effect for up to 60 days. A single dose of ADC #45 at 3 mg/kg or 1 mg/kg did not significantly inhibit tumor growth. However, although the difference was not significant, a single dose of ADC #45 at 3 mg/kg or 1 mg/kg did show slightly inhibition of tumor growth compared to PBS treated control group. Dose response was observed in this study, where higher dose showed better tumor growth inhibition (FIG. 2A). There was no body weight loss in the testing animals with a single dose of intravenously administered ADC #45 at 10 mg/kg or lower dose (FIG. 2B).

Figure 3:
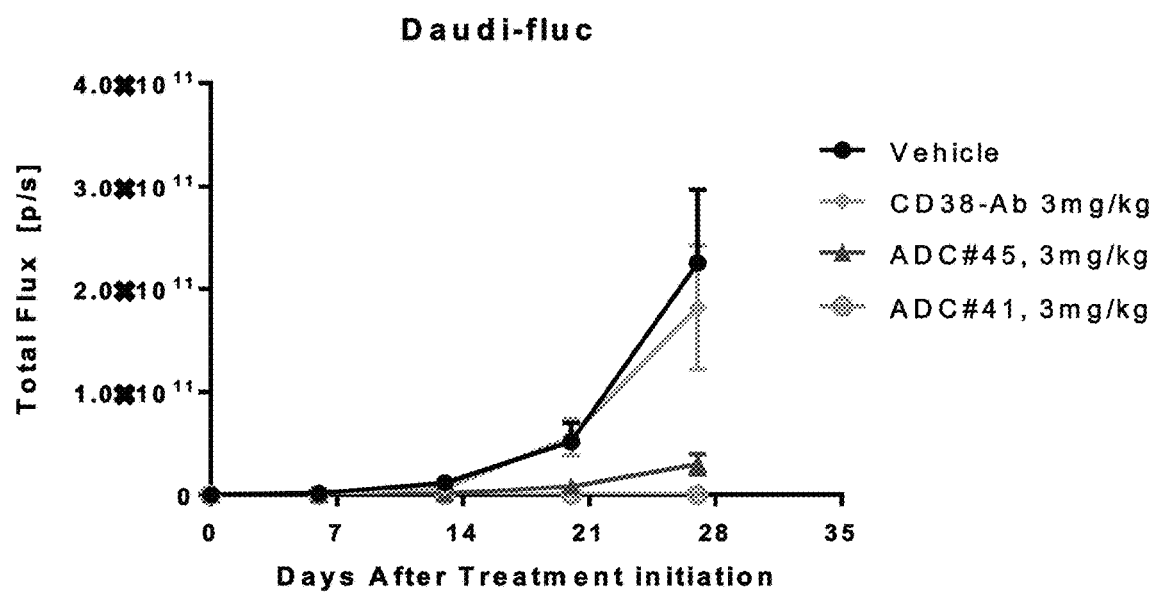
FIG. 3 shows an in vivo study of anti-CD38 ADCs on Burkitt lymphoma model. In the study, 10 million of Daudi-luc cells were iv injected to NOD-SCID mice. Anti-CD38 antibody (A2) and two anti-CD38 ADCs made with the same A2 antibody were iv injected to tumor bearing mice 14 days after injection of tumors
Figure 4:
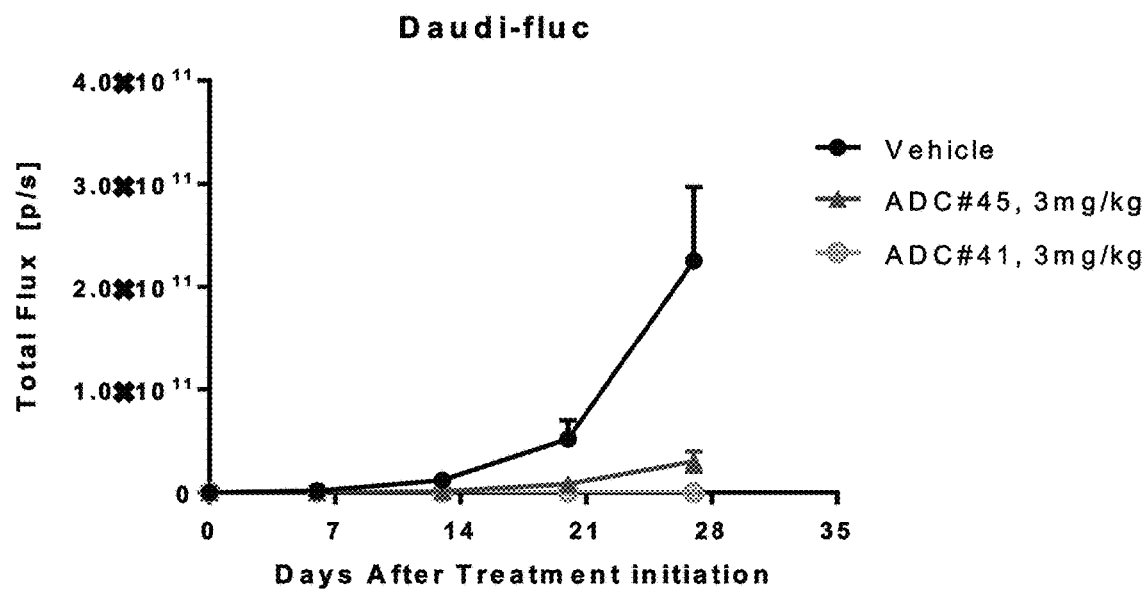
FIG. 4 shows an in vivo study of anti-CD38 ADCs on Burkitt lymphoma model. In the study, 10 million of Daudi-luc cells were iv injected to NOD-SCID mice. ADC #45 and ADC #41 were iv injected to tumor bearing mice 14 days after injection of tumors.
Figure 5:
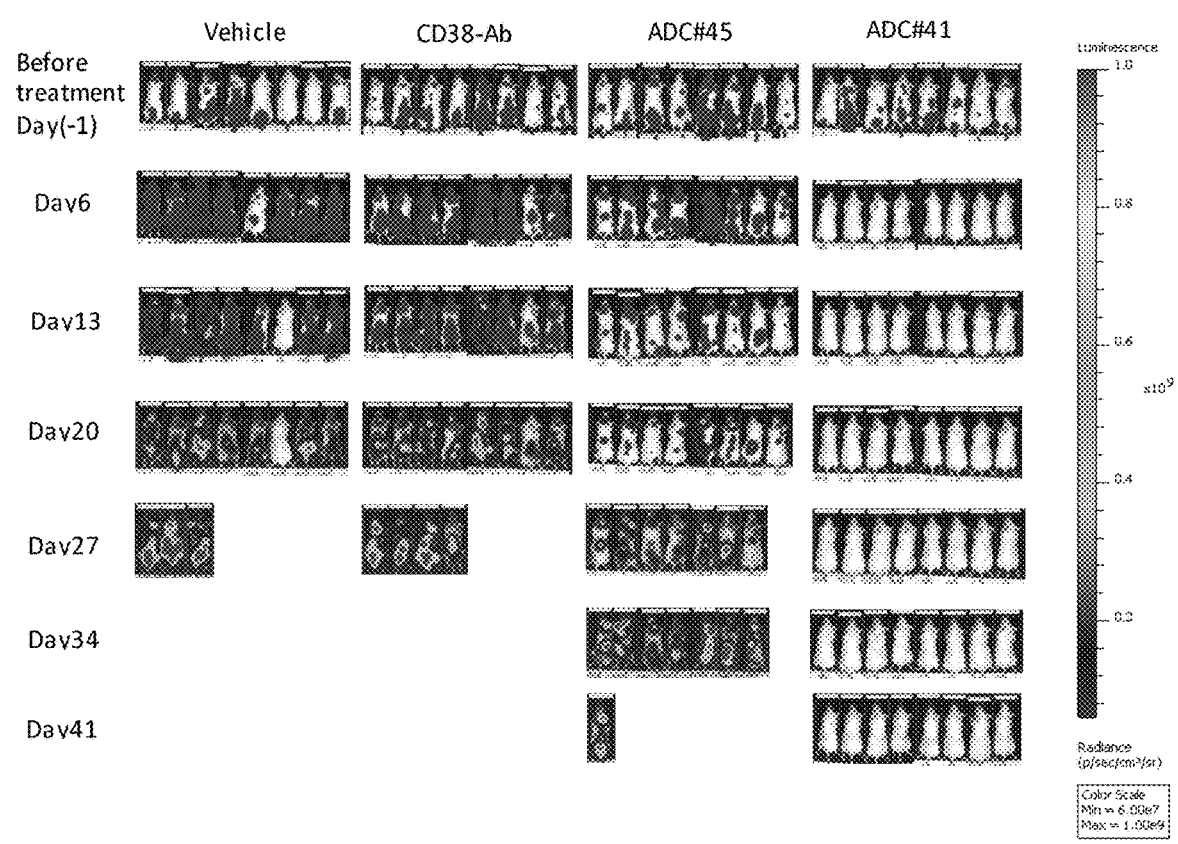
FIG. 5 shows an in vivo study of anti-CD38 ADCs on Burkitt lymphoma model. In the study, 10 million of Daudi-luc cells were iv injected to NOD-SCID mice. Anti-CD38 antibody and anti-CD38-ADC were iv injected to tumor bearing mice 14 days after injection of tumors. Mice images were taken once a week.
Figure 6:
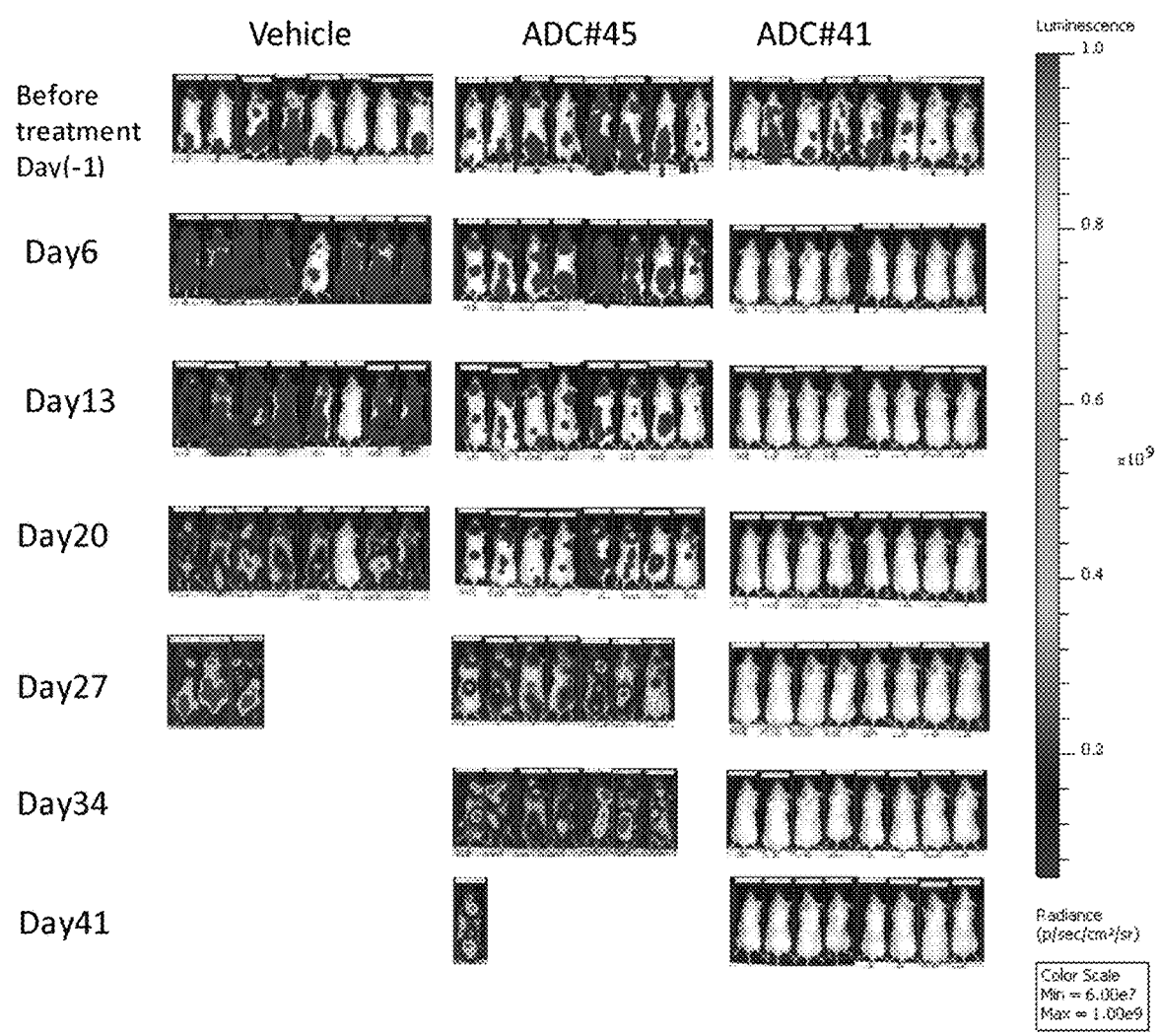
FIG. 6 shows an in vivo study of anti-CD38 ADCs on Burkitt lymphoma model. In the study, 10 million of Daudi-luc cells were iv injected to NOD-SCID mice. ADC #45 and ADC #41 were iv injected to tumor bearing mice 14 days after injection of tumors. The imagines of mice were taken once a week.
Figure 7:
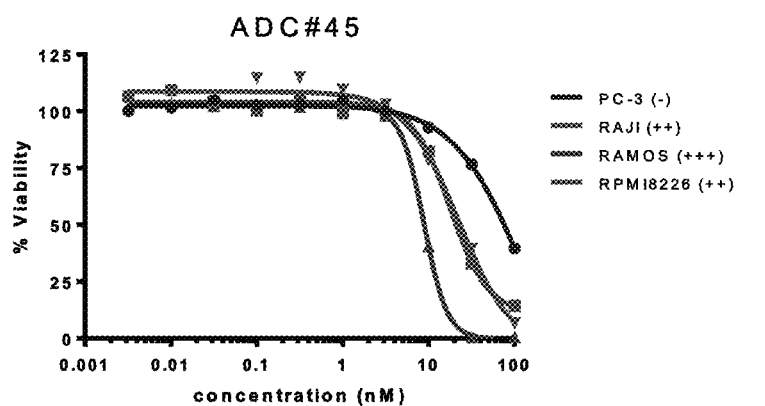
FIG. 7 shows CD38 expressing cancer cell lines, Ramos, Raji and RPMI8226, along with a CD38 negative cell line, PC-3 were plated in 96 well plate and treated with serial diluted ADC #45, ADC #41, and ADC #46, starting at 100 nM. The cells were treated for 3-5 days, depending on the nature of the conjugated payload. At the end of the treatment, the cells were stained with CelltitreGlo™ luminescent kit from Promega and the signals were captured by a luminescent plate reader. The activity of the ADCs on tumor cell growth inhibition were expressed as the concentration required for 50% cell growth inhibition, the so called EC50 (in nM). The data indicated that ADC #45, ADC #41, and ADC #46 showed selective inhibition toward cells that expressed CD38 on their surface.
Figure 7:
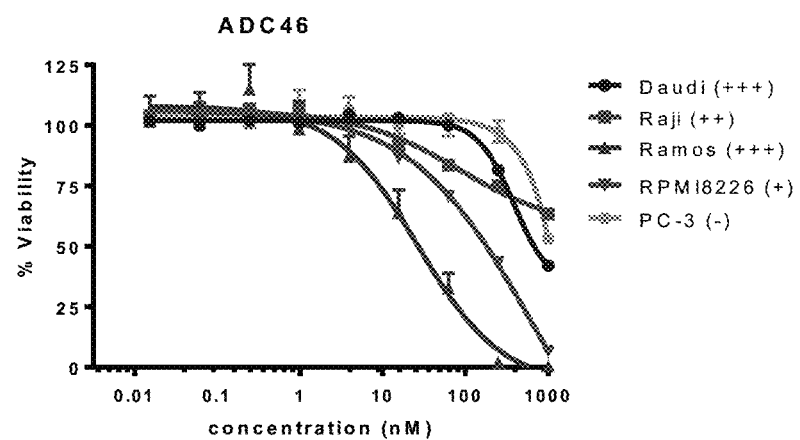
Figure 7:
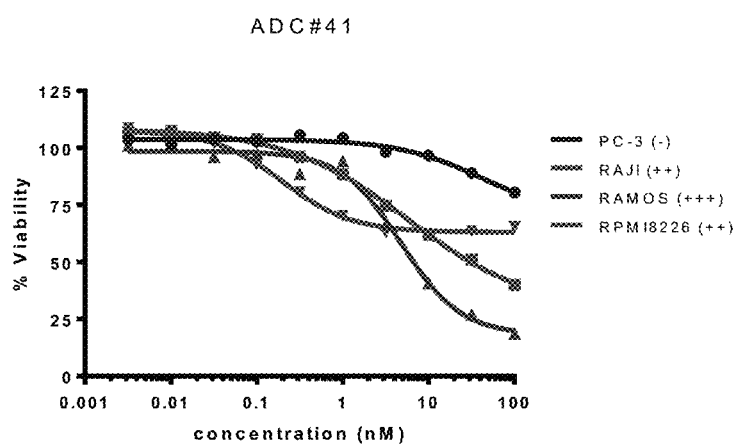

ADC #45 at a single dose of 3 mg/kg completely inhibited tumor growth with 100% survival up to Day 48 after treatment. ADC #41 at a single dose of 3 mg/kg significantly inhibited tumor growth compared to PBS control group, and significantly prolonged survival in mice. (FIGS. 3 and 4).

ADC #45 and ADC #41, at 10 mg/kg single dose, significantly inhibited tumor growth, while at 3 mg/kg, or 1 mg/kg, both did not show significant tumor inhibition in Daudi and Ramos subcutaneously injected xenograft tumor model in mice. ADC #45 at 3 mg/kg single dose completely inhibited tumor growth with a 100% survival up to 48 days in Daudi-luc intravenously injected tumor model in female NOD SCID mice. ADC #41 at 3 mg/kg single dose significantly inhibited tumor growth, and prolonged survival in Daudi-luc intravenously injected tumor model in female NOD SCID mice. Dose response was observed for ADC #45 and ADC #41 in this study. ADC #45 showed better tumor growth inhibition effect than ADC #41 with the same (10 mg/kg, or 3 mg/kg) dose regime. No treatment-related body weight loss was observed during the study for all treatment groups.

Sequence Listing

| Binder | Heavy chain variable domain region | Light chain variable domain region |
|---|---|---|
| A2 wt | QVQLVESGGGLVKPGGSLRLSCAAS GFTFSDDYMSWIRQAPGKGLEWVAS VSNGRPTTYYADSVRGRFTISRDNA KNSLYLQMNSLRAEDTAVYYCARE DWGGEFTDWGRGTLVTVSS SEQ ID NO. 1 | QAGLTQPPSASGT SGQRVTISCSGSS SNIGINFVYWYQH LPGTAPKLLIYKN NQRPSGVPDRFSG SKSGNSASLAISG LRSEDEADYYCAA WDDSLSGYVFGSG TKVTVL SEQ ID NO. 2 |
| A2-SV | QVQLVESGGGLVKPGGSLRLSCAAS GFTFSDDYMSWIRQAPGKGLEWVAS VSNGRPTTYYADSVRGRFTISRDNA KNSLYLQMNSLRAEDTAVYYCARE DWGGEFTDWGRGTLVTVSS SEQ ID NO. 1 | QSVLTQPPSASGT SGQRVTISCSGSS SNIGINFVYWYQH LPGTAPKLLIYKN NORPSGVPDRFSG SKSGNSASLAISG LRSEDEADYYCAA WDDSLSGYVFGSG TKVTVL SEQ ID NO. 3 |

We claim:

1. An antibody drug conjugate (ADC) composition comprising an IgG antibody that binds to CD38, a linker moiety conjugated to a Cys residue in a hinge region of an IgG antibody, wherein the IgG antibody comprises a heavy chain mutated such that the hinge region contains only one Cys residue, wherein the ADC is chosen from

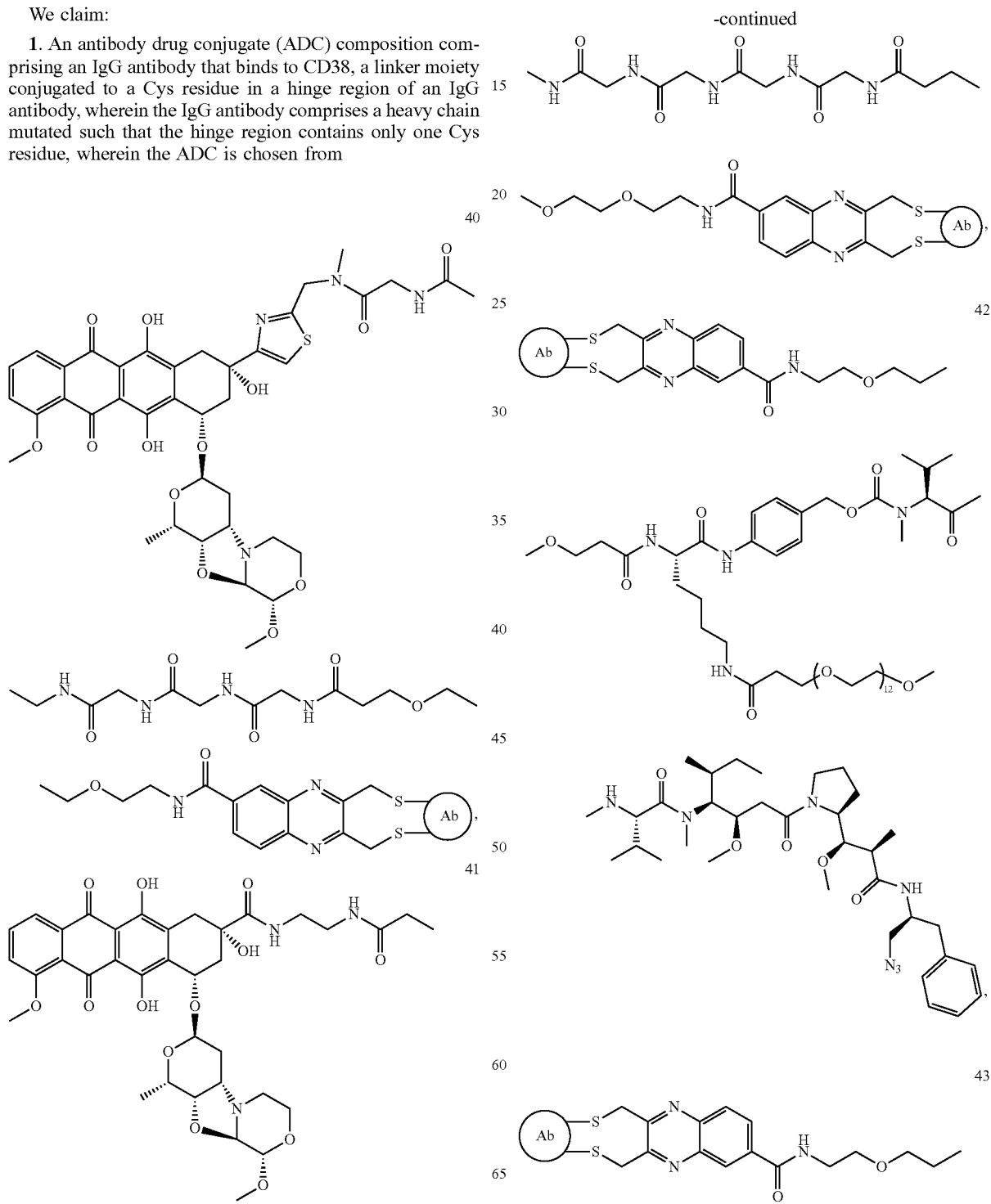

85
-continued
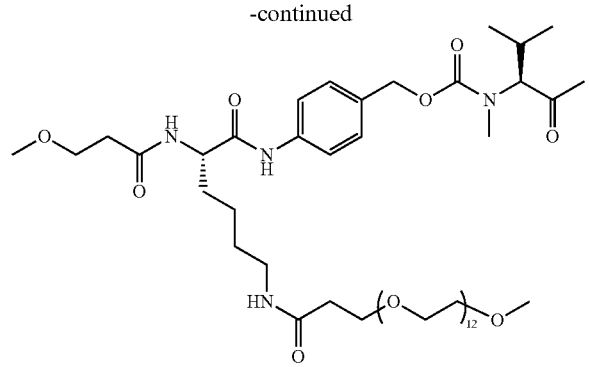
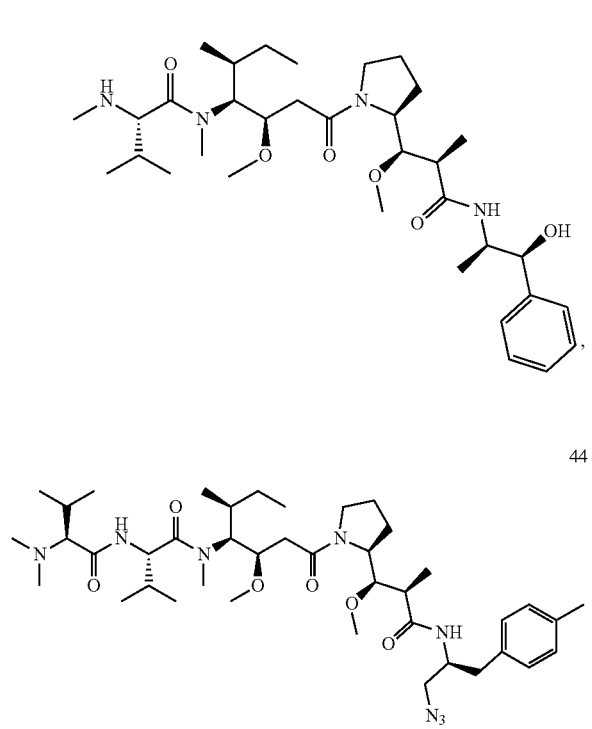
86
-continued
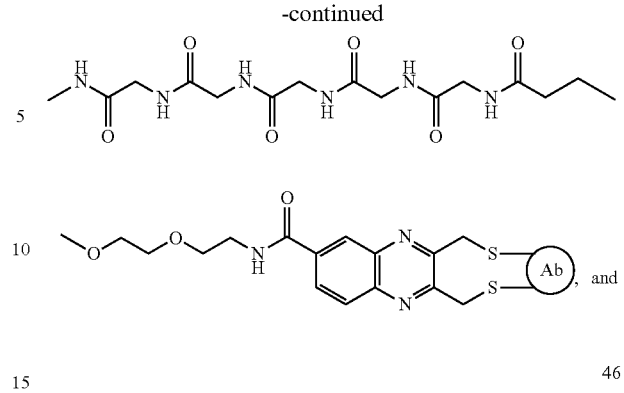
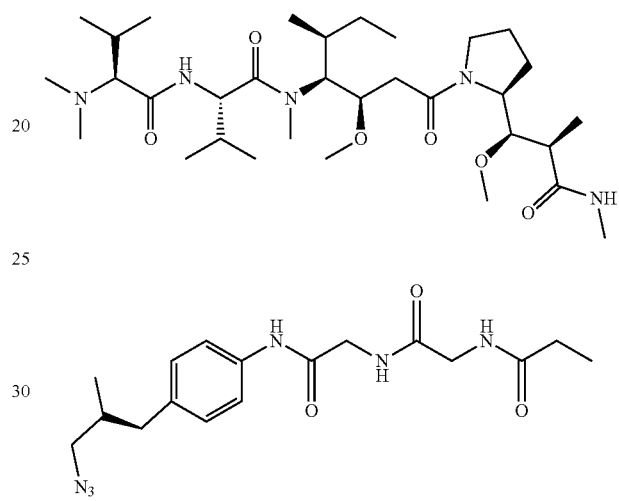
2. The ADC composition of claim 1, wherein the ADC is
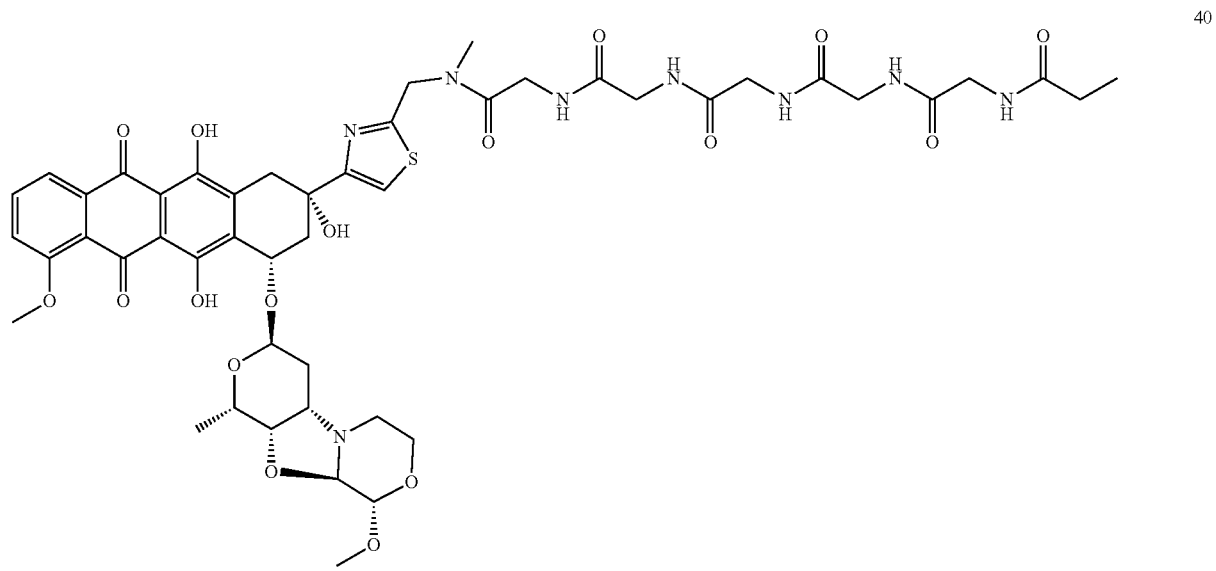

-continued
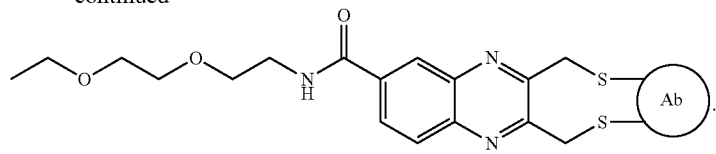
3. The ADC composition of claim 1, wherein the ADC is
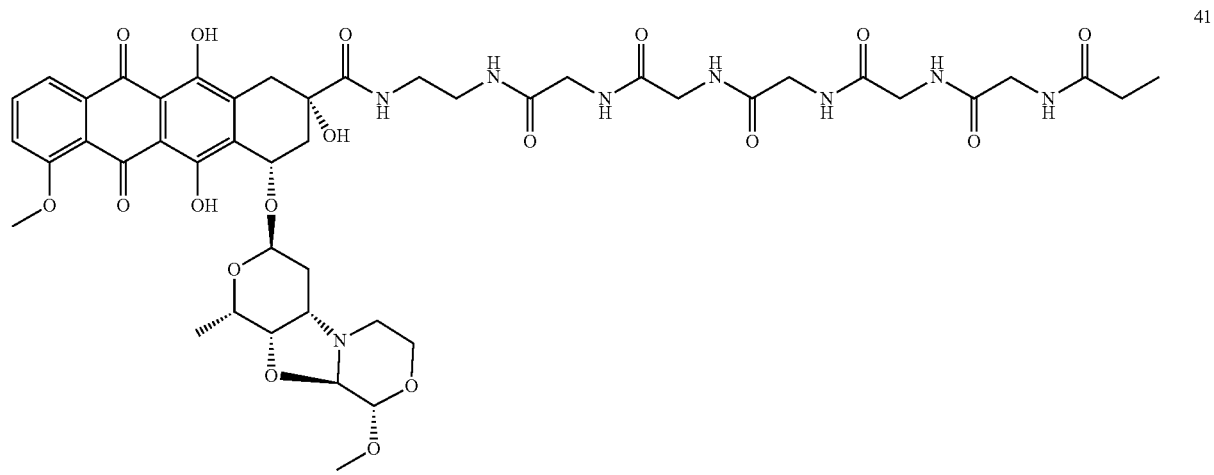
41
4. The ADC composition of claim 1, wherein the ADC is
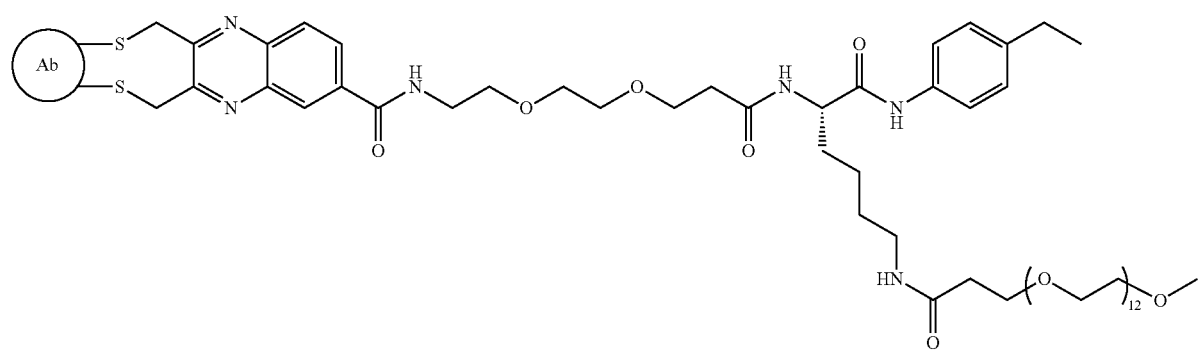
42

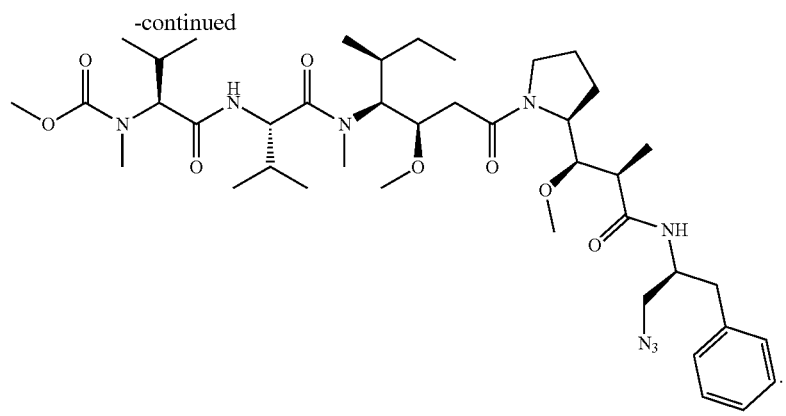
5. The ADC composition of claim 1, wherein the ADC is
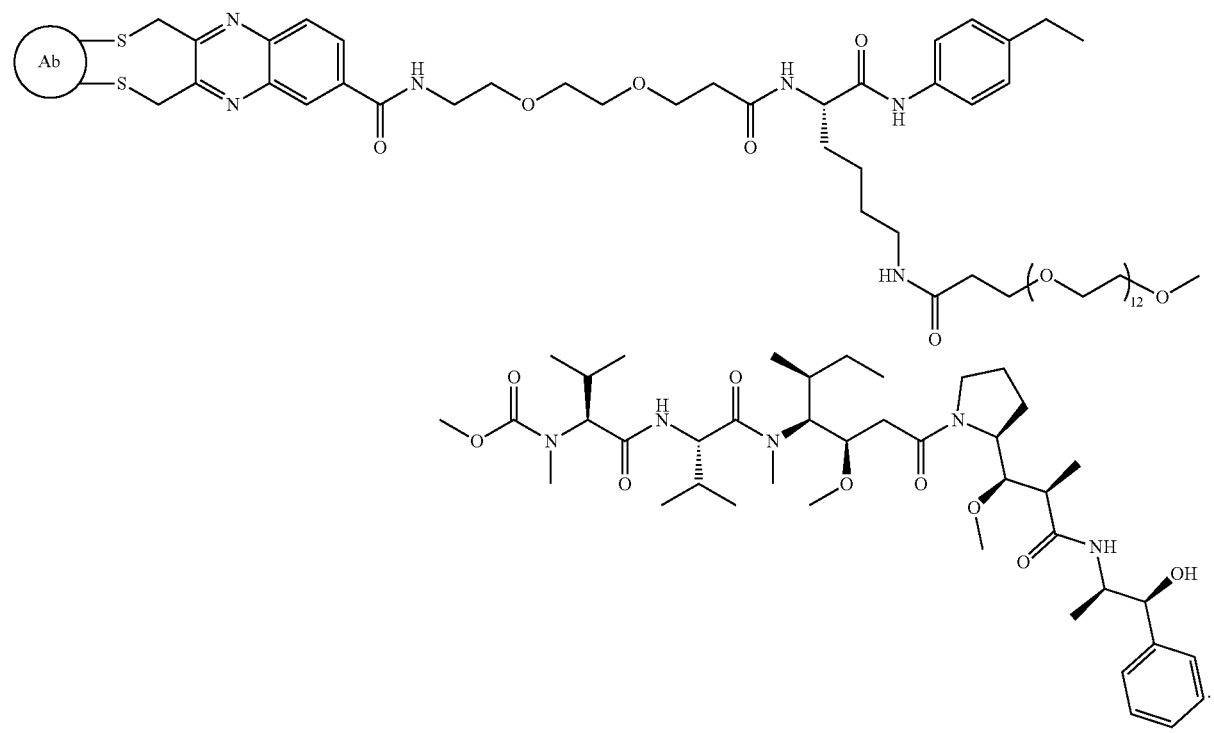
6. The ADC composition of claim 1, wherein the ADC is
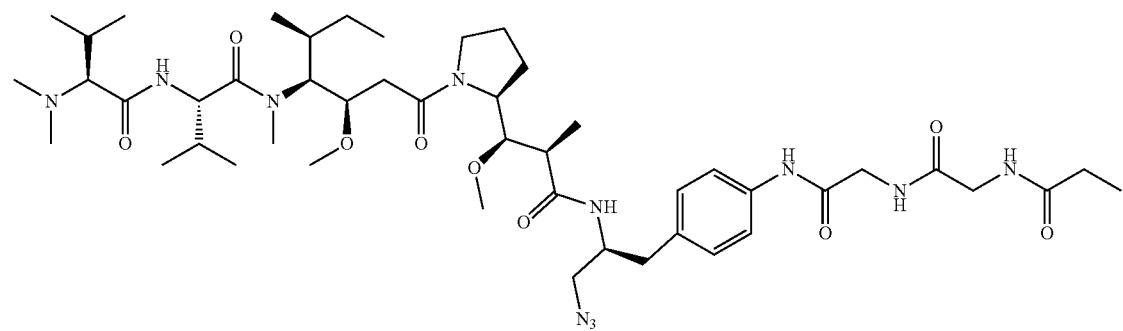

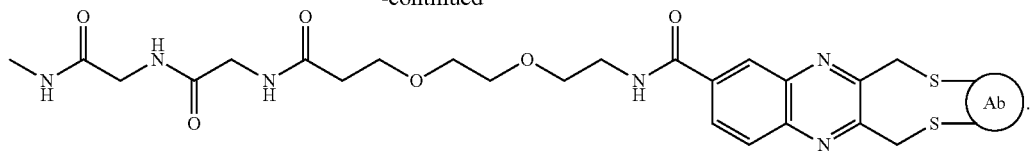

7. The ADC composition of claim 1, wherein the ADC is

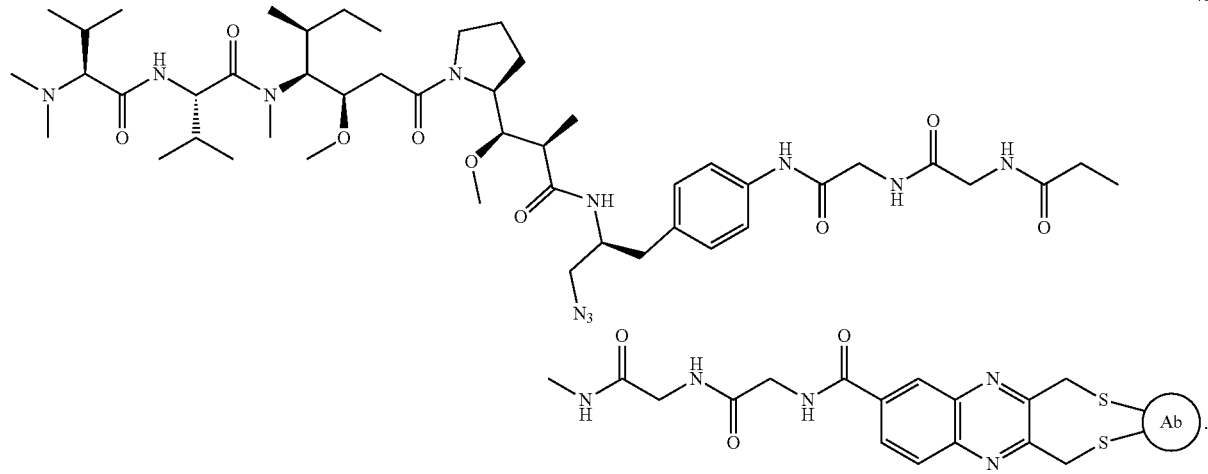

8. An anti-CD38 ADC composition comprising:
(a) an anti-CD38 IgG antibody comprising a heavy chain variable region comprising the sequence of SEQ ID NO. 1 and a light chain variable region comprising the sequence of SEQ ID NO. 2 or 3;
(b) a conjugation linker moiety, wherein the conjugation linker comprises a linker and a conjugation moiety which covalently binds to a single Cys residue in a hinge region of an IgG antibody, and
wherein the anti-CD38 ADC is chosen from:

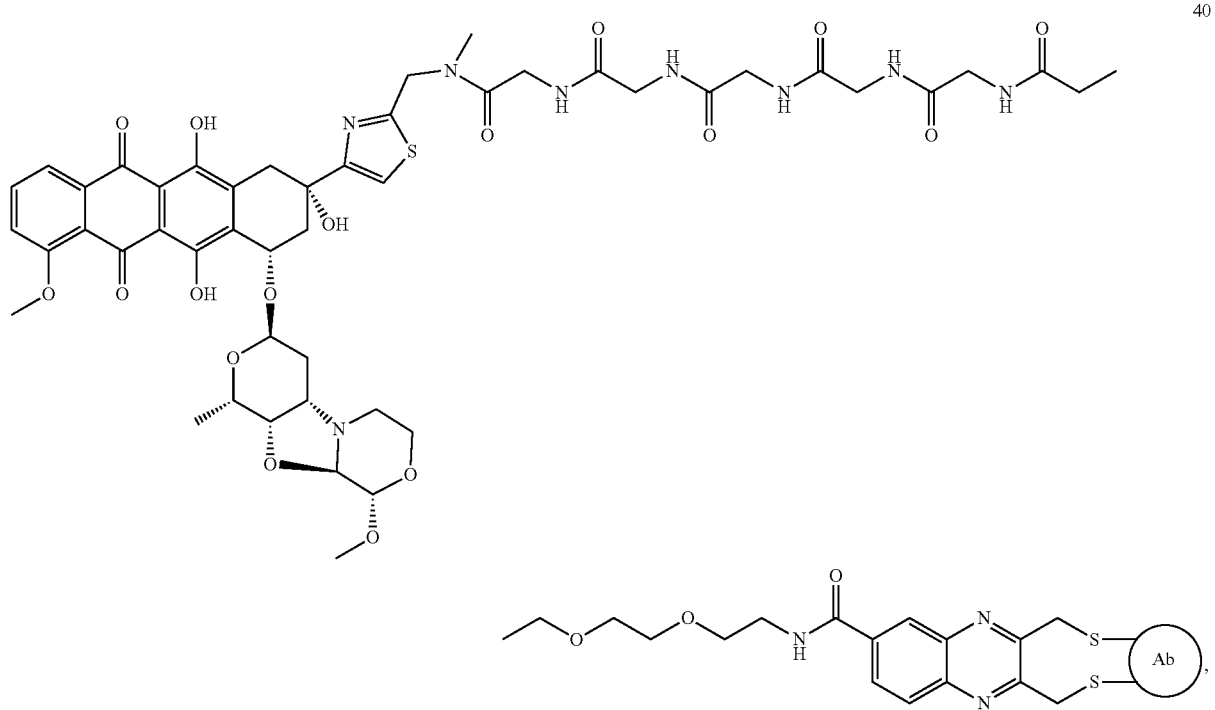

-continued
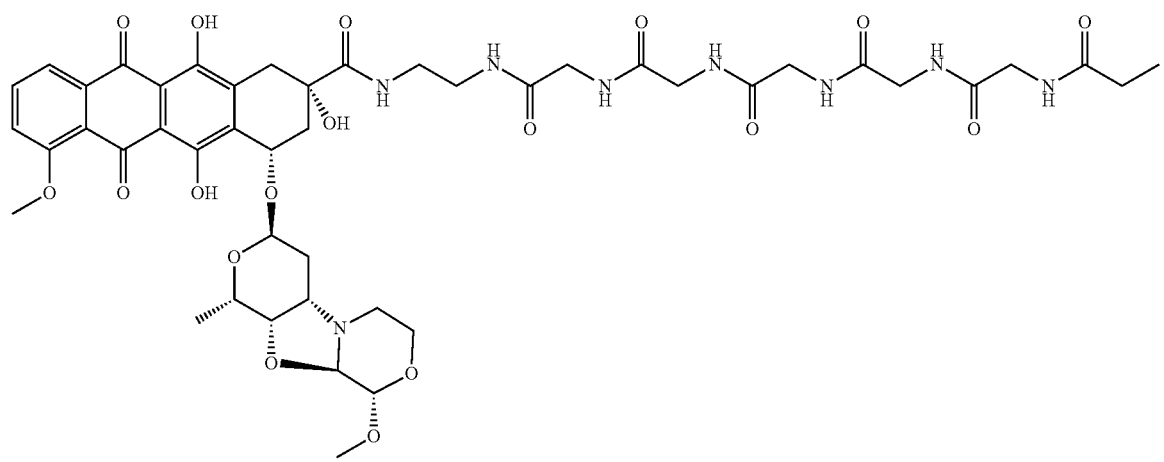
41
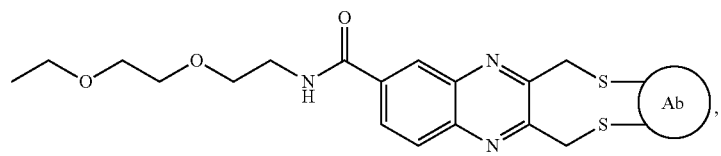
42
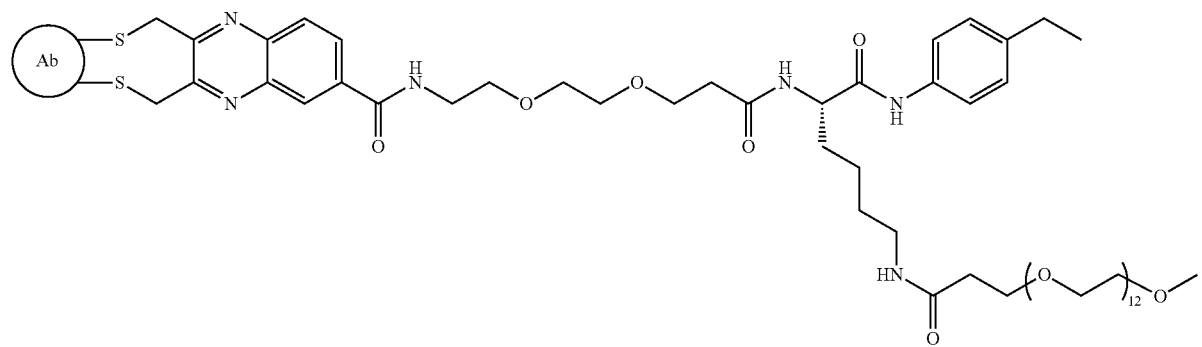
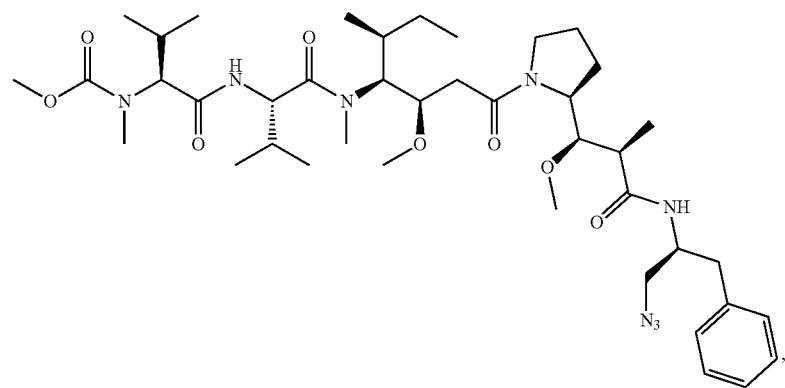

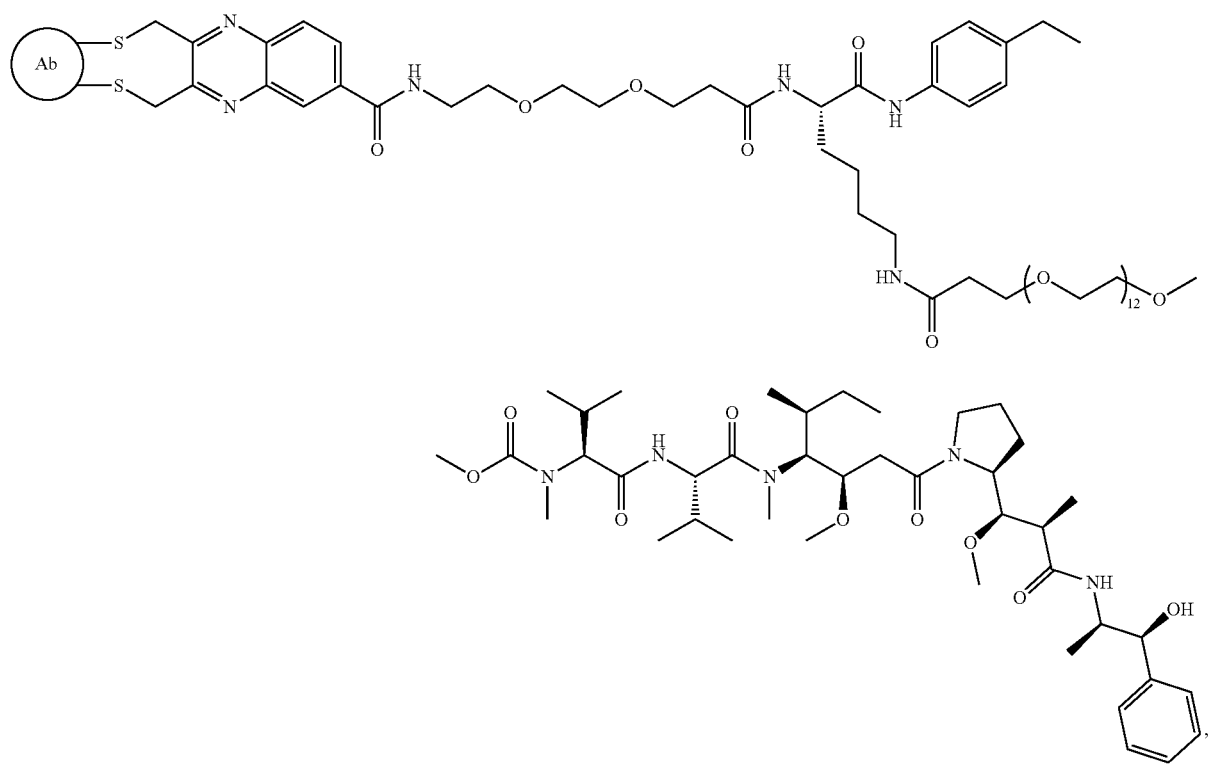
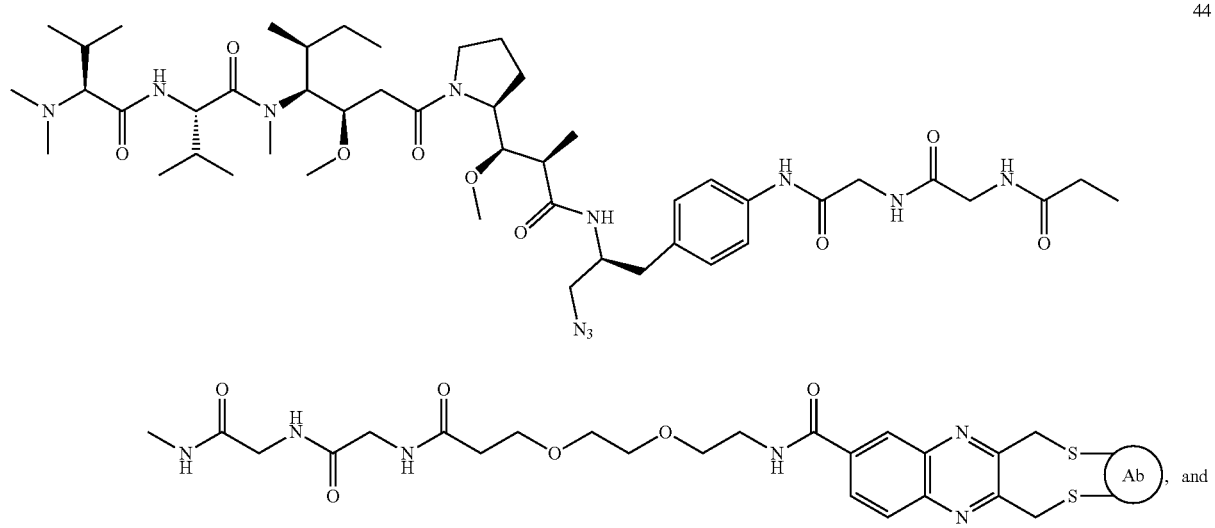
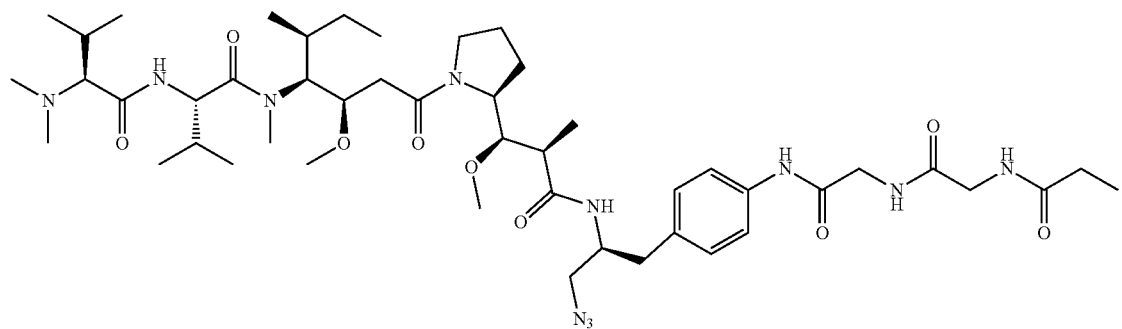

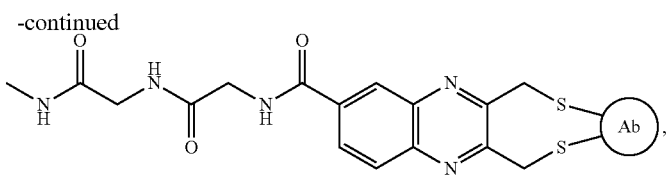
wherein Ab is the anti-CD38 IgG antibody.
9. The ADC composition of claim 8, wherein the ADC is
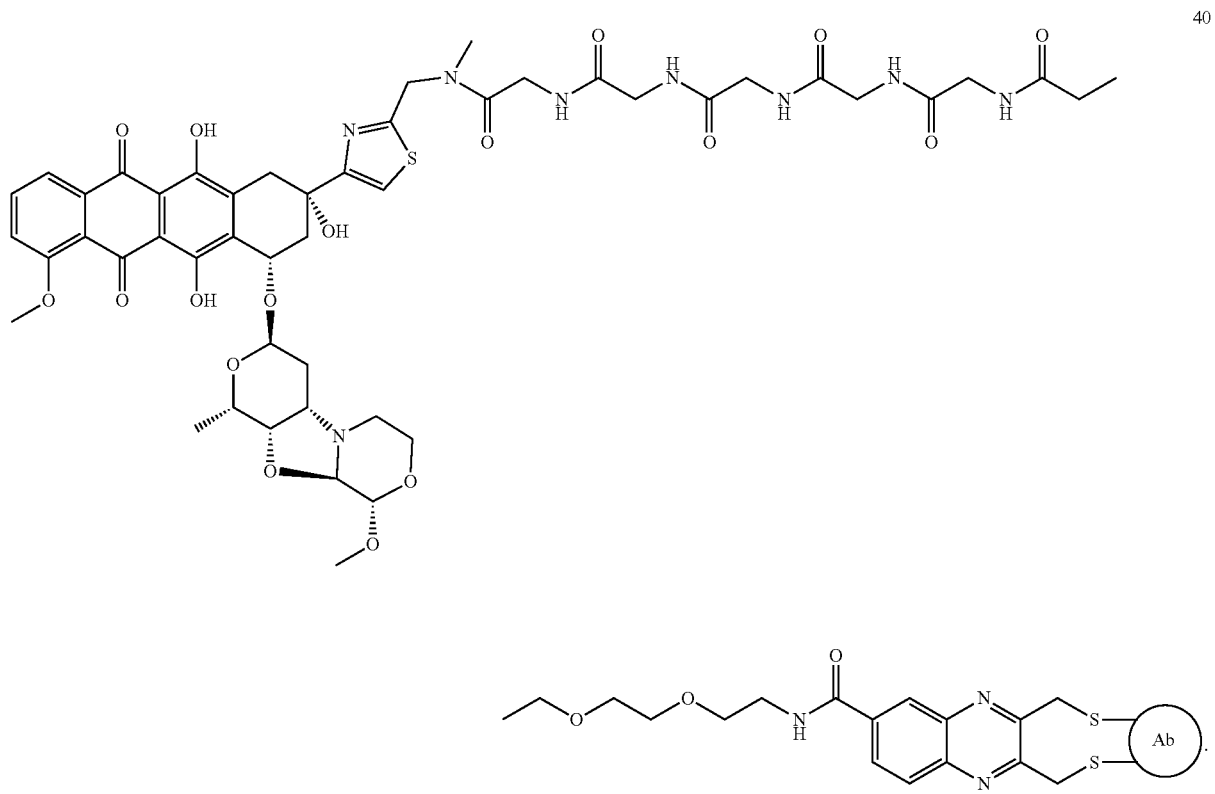
10. The ADC composition of claim 8, wherein the ADC is
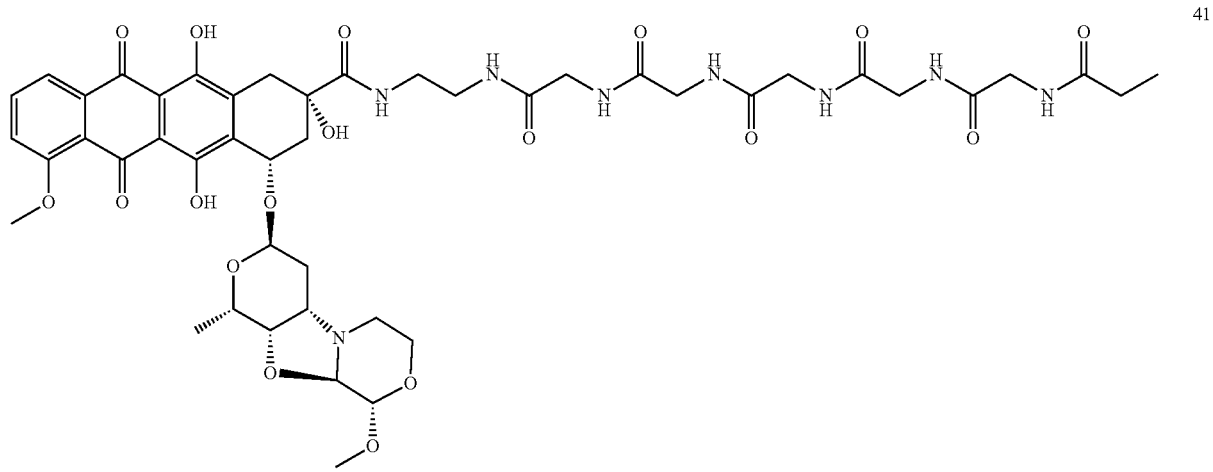

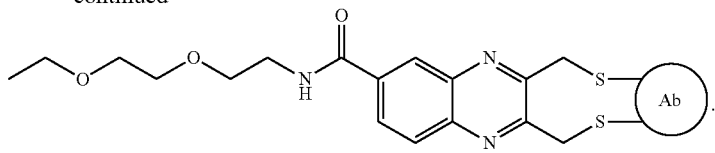
11. The ADC composition of claim 8, wherein the ADC is
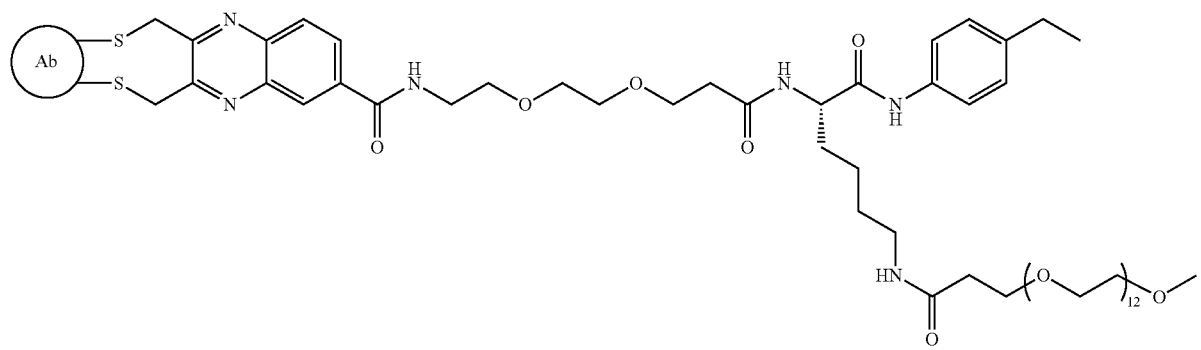
42
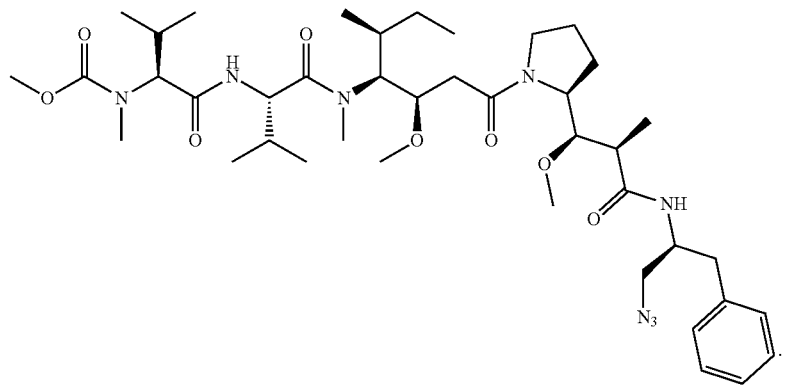
12. The ADC composition of claim 8, wherein the ADC is
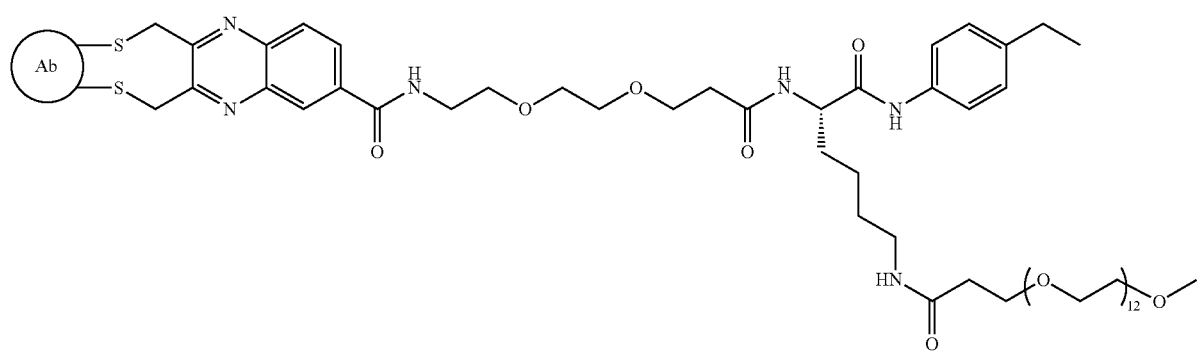
43

-continued
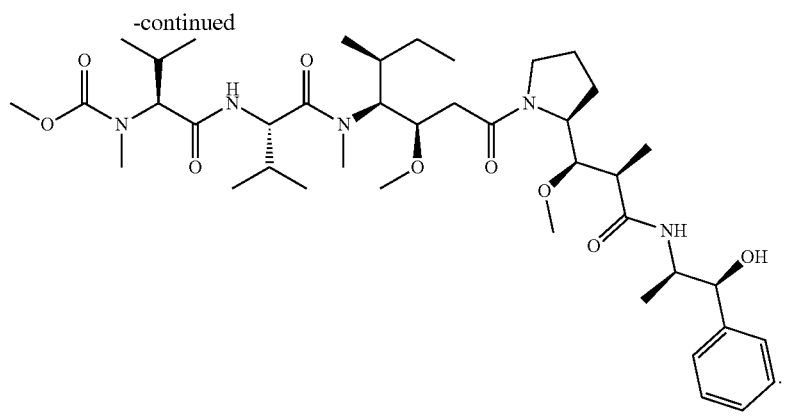
13. The ADC composition of claim 8, wherein the ADC is
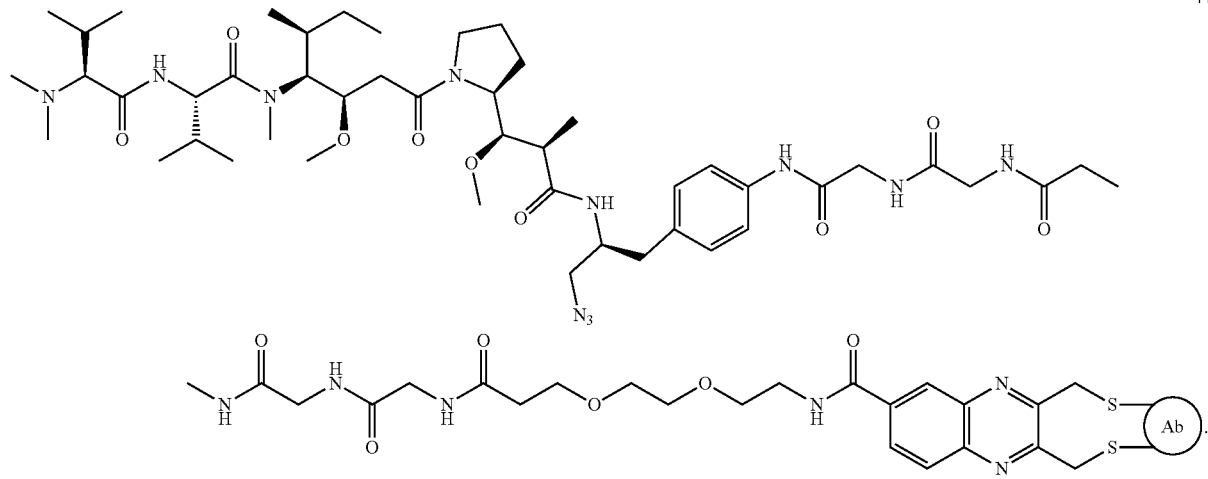
44
14. The ADC composition of claim 8, wherein the ADC is
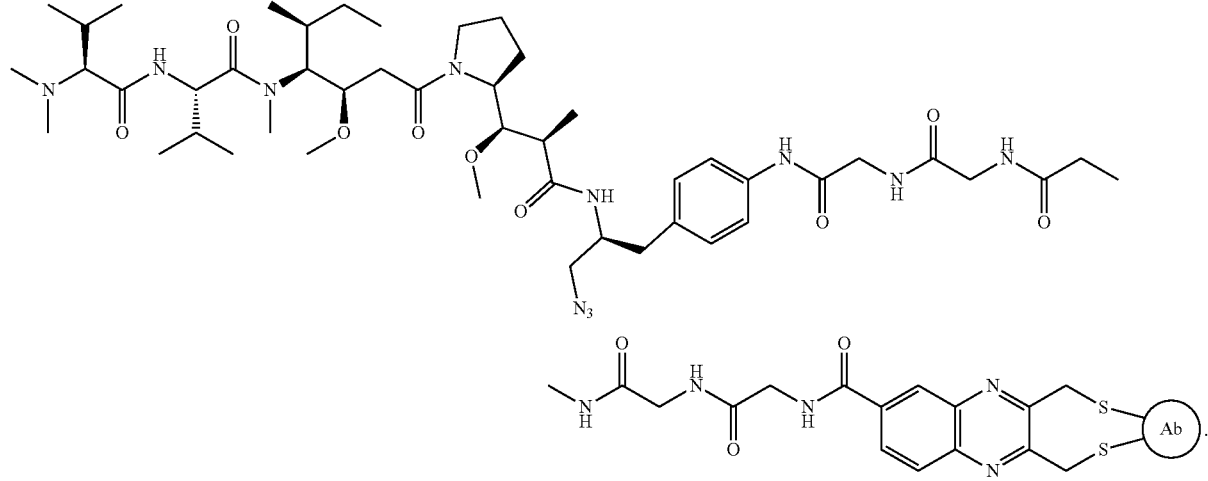
46

15. The ADC composition of claim 8, wherein the heavy chain hinge region of the IgG antibody is mutated such that the heavy chain hinge region contains only one Cys residue.
16. A compound selected from:
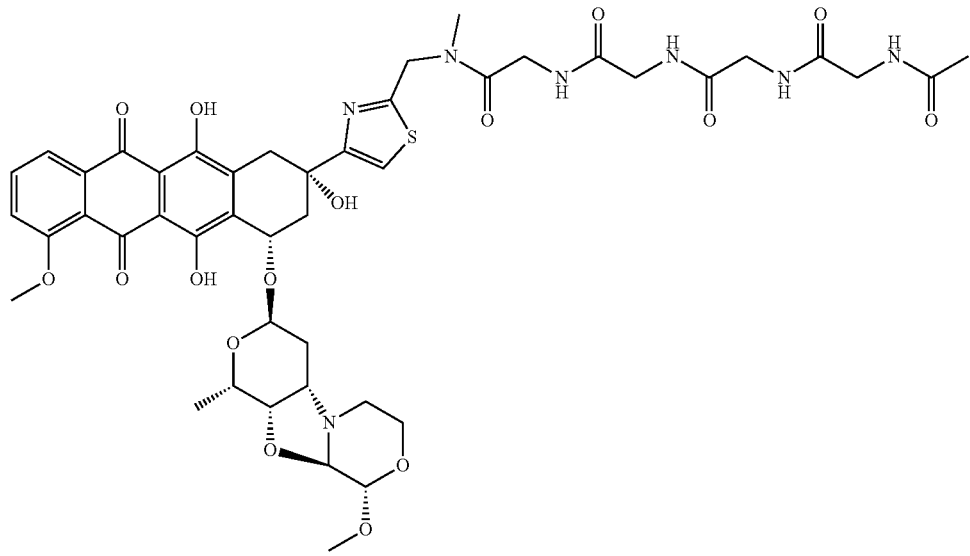
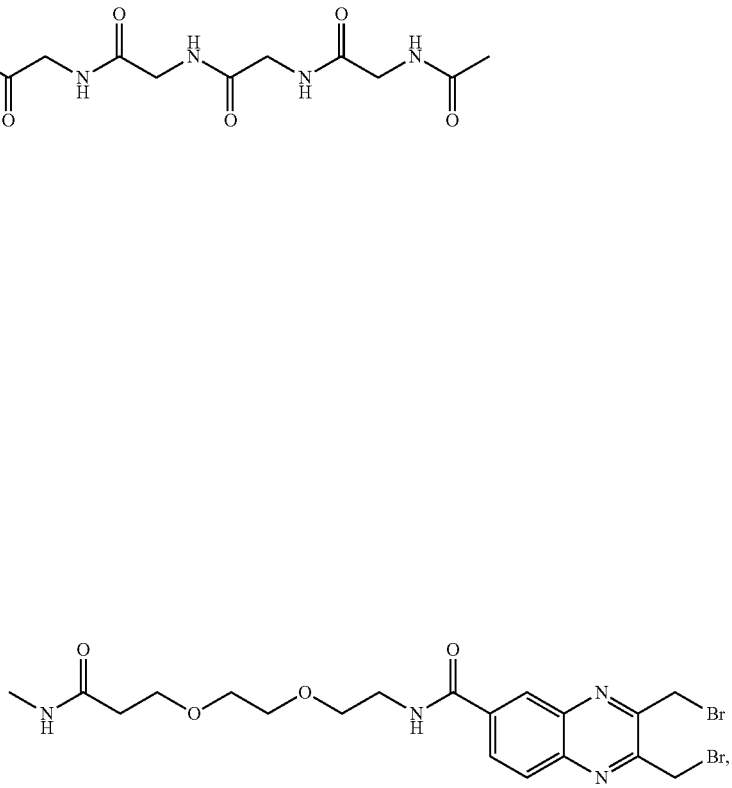
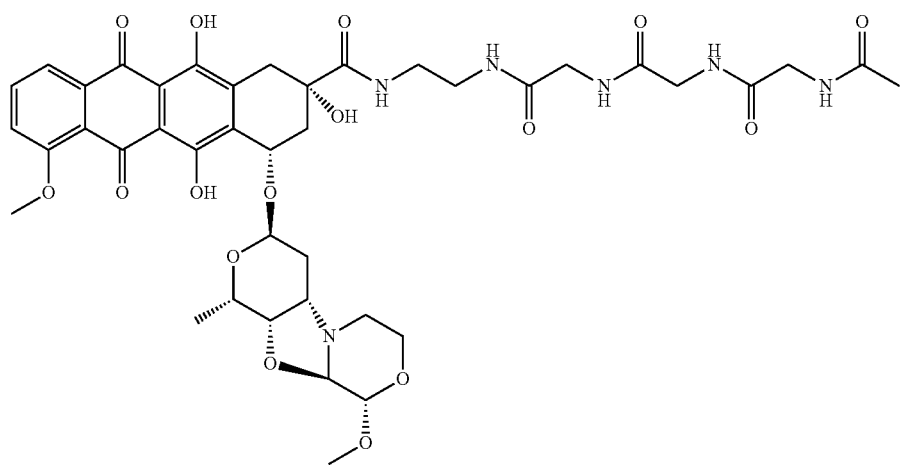
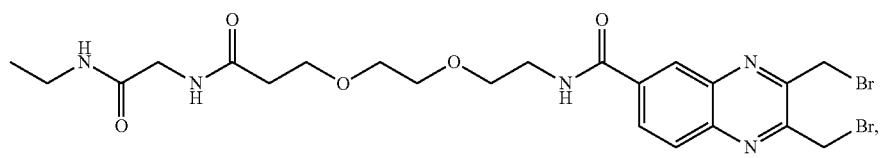

105
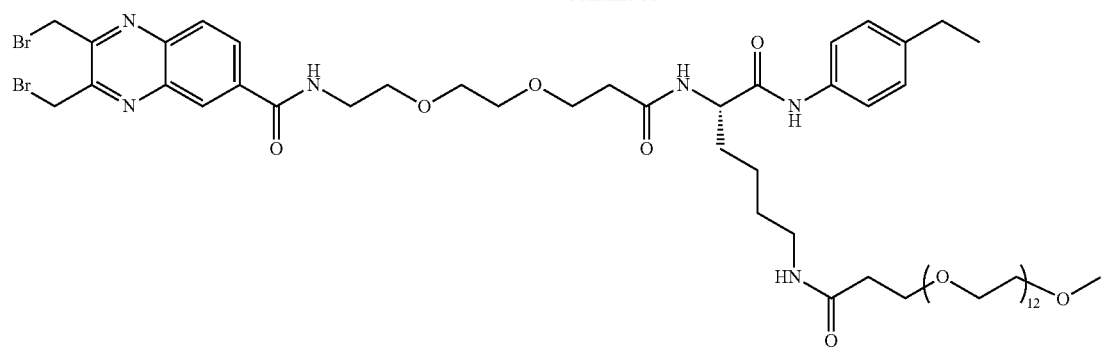
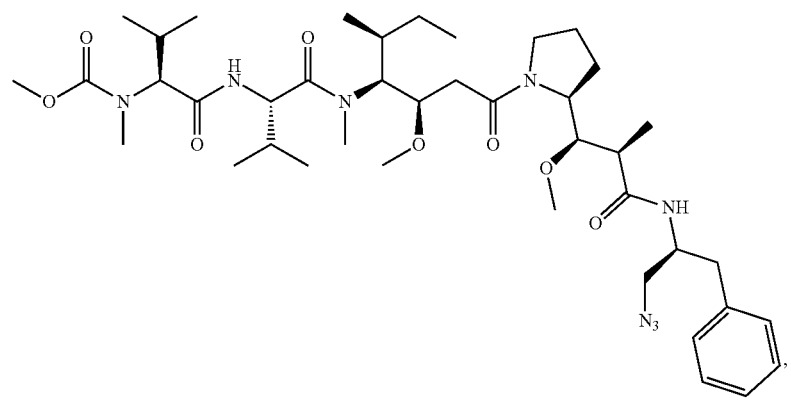
106
-continued
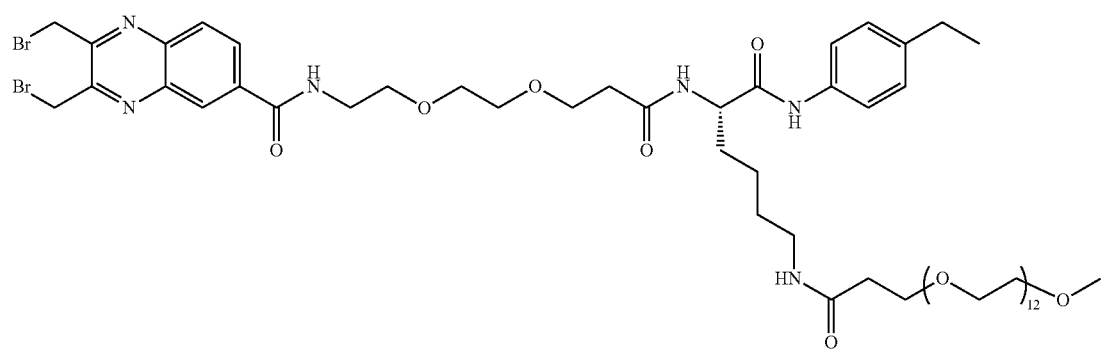
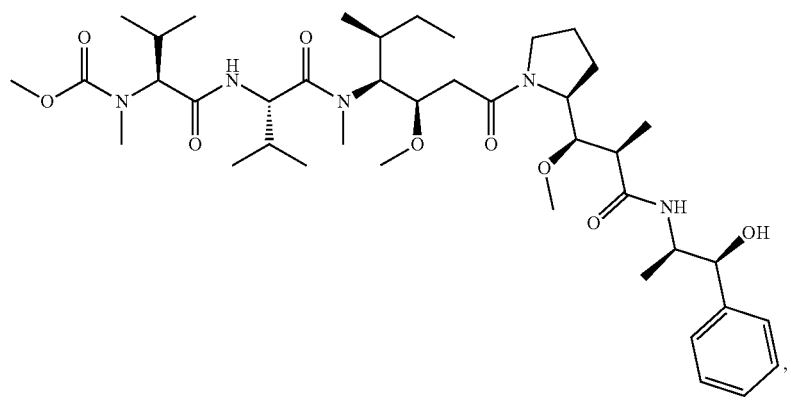

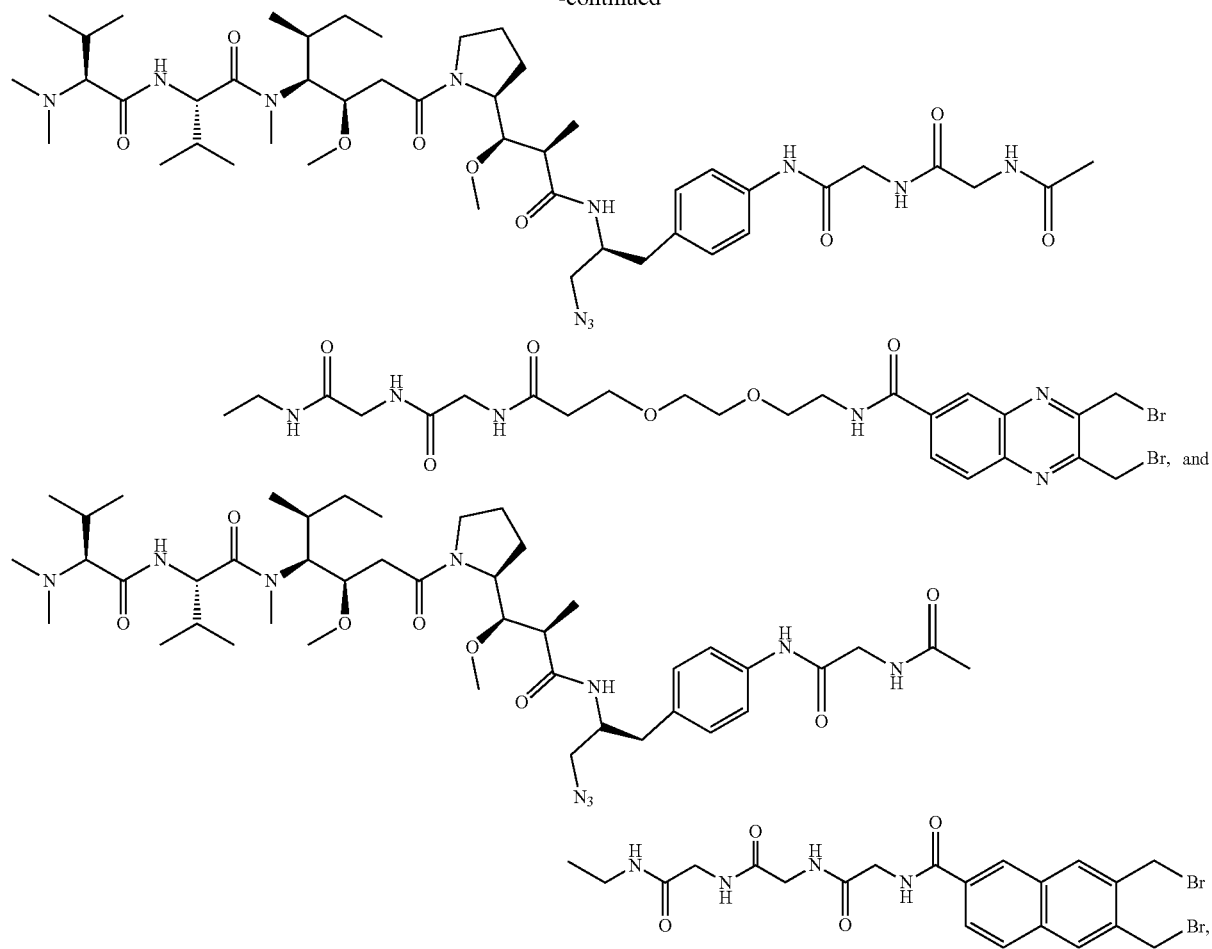
or a pharmaceutically acceptable salt thereof.
* * * * *

SEQUENCE LISTING

<160> NUMBER OF SEQ ID NOS: 3

<210> SEQ ID NO 1

```
<211> LENGTH: 118
<212> TYPE: PRT
<213> ORGANISM: Homo sapiens

<400> SEQUENCE: 1

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Asp
            20                  25                  30

Tyr Met Ser Trp Ile Arg Gln Ala Pro Gly Lys Gly Leu Glu Trp Val
        35                  40                  45

Ala Ser Val Ser Asn Gly Arg Pro Thr Thr Tyr Tyr Ala Asp Ser Val
    50                  55                  60

Arg Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Asp Trp Gly Gly Glu Phe Thr Asp Trp Gly Arg Gly Thr
            100                 105                 110

Leu Val Thr Val Ser Ser
            115

<210> SEQ ID NO 2
<211> LENGTH: 110
<212> TYPE: PRT
<213> ORGANISM: Homo sapiens

<400> SEQUENCE: 2

Gln Ala Gly Leu Thr Gln Pro Pro Ser Ala Ser Gly Thr Ser Gly Gln
1               5                   10                  15

Arg Val Thr Ile Ser Cys Ser Gly Ser Ser Ser Asn Ile Gly Ile Asn
            20                  25                  30

Phe Val Tyr Trp Tyr Gln His Leu Pro Gly Thr Ala Pro Lys Leu Leu
        35                  40                  45

Ile Tyr Lys Asn Asn Gln Arg Pro Ser Gly Val Pro Asp Arg Phe Ser
    50                  55                  60

Gly Ser Lys Ser Gly Asn Ser Ala Ser Leu Ala Ile Ser Gly Leu Arg
65                  70                  75                  80

Ser Glu Asp Glu Ala Asp Tyr Tyr Cys Ala Ala Trp Asp Asp Ser Leu
                85                  90                  95

Ser Gly Tyr Val Phe Gly Ser Gly Thr Lys Val Thr Val Leu
            100                 105                 110

<210> SEQ ID NO 3
<211> LENGTH: 110
<212> TYPE: PRT
<213> ORGANISM: Homo sapiens

<400> SEQUENCE: 3

Gln Ser Val Leu Thr Gln Pro Pro Ser Ala Ser Gly Thr Ser Gly Gln
1               5                   10                  15

Arg Val Thr Ile Ser Cys Ser Gly Ser Ser Ser Asn Ile Gly Ile Asn
            20                  25                  30

Phe Val Tyr Trp Tyr Gln His Leu Pro Gly Thr Ala Pro Lys Leu Leu
        35                  40                  45

Ile Tyr Lys Asn Asn Gln Arg Pro Ser Gly Val Pro Asp Arg Phe Ser
    50                  55                  60
```

| | | | | | | | | | | | | | | | |
|---|---|---|---|---|---|---|---|---|---|---|---|---|---|---|---|
| Gly | Ser | Lys | Ser | Gly | Asn | Ser | Ala | Ser | Leu | Ala | Ile | Ser | Gly | Leu | Arg |
| 65 | | | | 70 | | | | | 75 | | | | | | 80 |
| Ser | Glu | Asp | Glu | Ala | Asp | Tyr | Tyr | Cys | Ala | Ala | Trp | Asp | Asp | Ser | Leu |
| | | | | 85 | | | | | 90 | | | | | 95 | |
| Ser | Gly | Tyr | Val | Phe | Gly | Ser | Gly | Thr | Lys | Val | Thr | Val | Leu | | |
| | | | 100 | | | | | 105 | | | | | 110 | | |